United States Patent
Fu et al.

(10) Patent No.: US 11,357,752 B2
(45) Date of Patent: Jun. 14, 2022

(54) CAROLACTON AND DERIVATIVES THEREOF FOR USE IN THE TREATMENT OF CELL PROLIFERATION DISORDERS

(71) Applicant: Helmholtz-Zentrum für Infektionsforschung GmbH, Braunschweig (DE)

(72) Inventors: Chengzhang Fu, Saarbrucken (DE); Rolf Muller, Blieskastel (DE); Jannik Donner, Nienstadt (DE); Michael Reck, Gehrden (DE); Irene Wagner-Dobler, Evessen (DE); Andreas Kirschning, Celle (DE); Jonas Ammermann, Hannover (DE)

(73) Assignee: HELMHOLTZ-ZENTRUM FUR INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 16/618,157

(22) PCT Filed: Jun. 1, 2018

(86) PCT No.: PCT/EP2018/064462
§ 371 (c)(1),
(2) Date: Nov. 28, 2019

(87) PCT Pub. No.: WO2018/220176
PCT Pub. Date: Dec. 6, 2018

(65) Prior Publication Data
US 2021/0186926 A1 Jun. 24, 2021

(30) Foreign Application Priority Data
Jun. 1, 2017 (EP) .................................... 17174066

(51) Int. Cl.
*A61K 31/365* (2006.01)
*A61P 35/02* (2006.01)
*A61P 35/00* (2006.01)

(52) U.S. Cl.
CPC ............ *A61K 31/365* (2013.01); *A61P 35/00* (2018.01); *A61P 35/02* (2018.01)

(58) Field of Classification Search
CPC ..................................................... A61K 31/365
See application file for complete search history.

(56) References Cited

FOREIGN PATENT DOCUMENTS

| EP | 2033642 A1 | 3/2009 |
|---|---|---|
| WO | 02/099113 A1 | 12/2002 |

OTHER PUBLICATIONS

Liu. Digestive and L:iver Disease, 2016, 48, 953-960 (Year: 2016).*
Sheppard. Scientific Reports, 2015, 1-11 (Year: 2015).*
Murta. Molecular Microbiology, 2009, 71(6), 1386-1401 (Year: 2009).*
Kunze. BMC Microbiology, 2010, 10,: 199, pp. 1-13 (Year: 2010).*
Int'l. Search Report for PCT/EP2018/064462, dated Sep. 20, 2018.
Stumpp N., et al., "Synthesis of new carolacton derivatives and their activity against biofilms of oral bacteria." Organic & Biomolecular Chemistry May 28, 2015, vol. 13, No. 20, May 28, 2015 (May 28, 2015), pp. 5765-5774, XP002774969, ISSN: 1477-0539, the whole document.

* cited by examiner

*Primary Examiner* — Noble E Jarrell
(74) *Attorney, Agent, or Firm* — Blue Filament Law PLLC

(57) ABSTRACT

Chemical compounds are provided that are useful in the treatment of diseases associated with an activity of a 5,10-methylenyltetrahydrofolate cyclohydrolase/5,10-methylene tetrahydrofolate dehydrogenase enzyme in pathological eukaryotic cells. In particular, compounds that exhibit inhibitory activity upon 5,10-methylenyltetrahydrofolate cyclohydrolase/5,10-methylene tetrahydrofolate dehydrogenase enzymes and their use in the treatment of cancer and/or parasitic diseases are provided.

9 Claims, 23 Drawing Sheets

Figure 1:
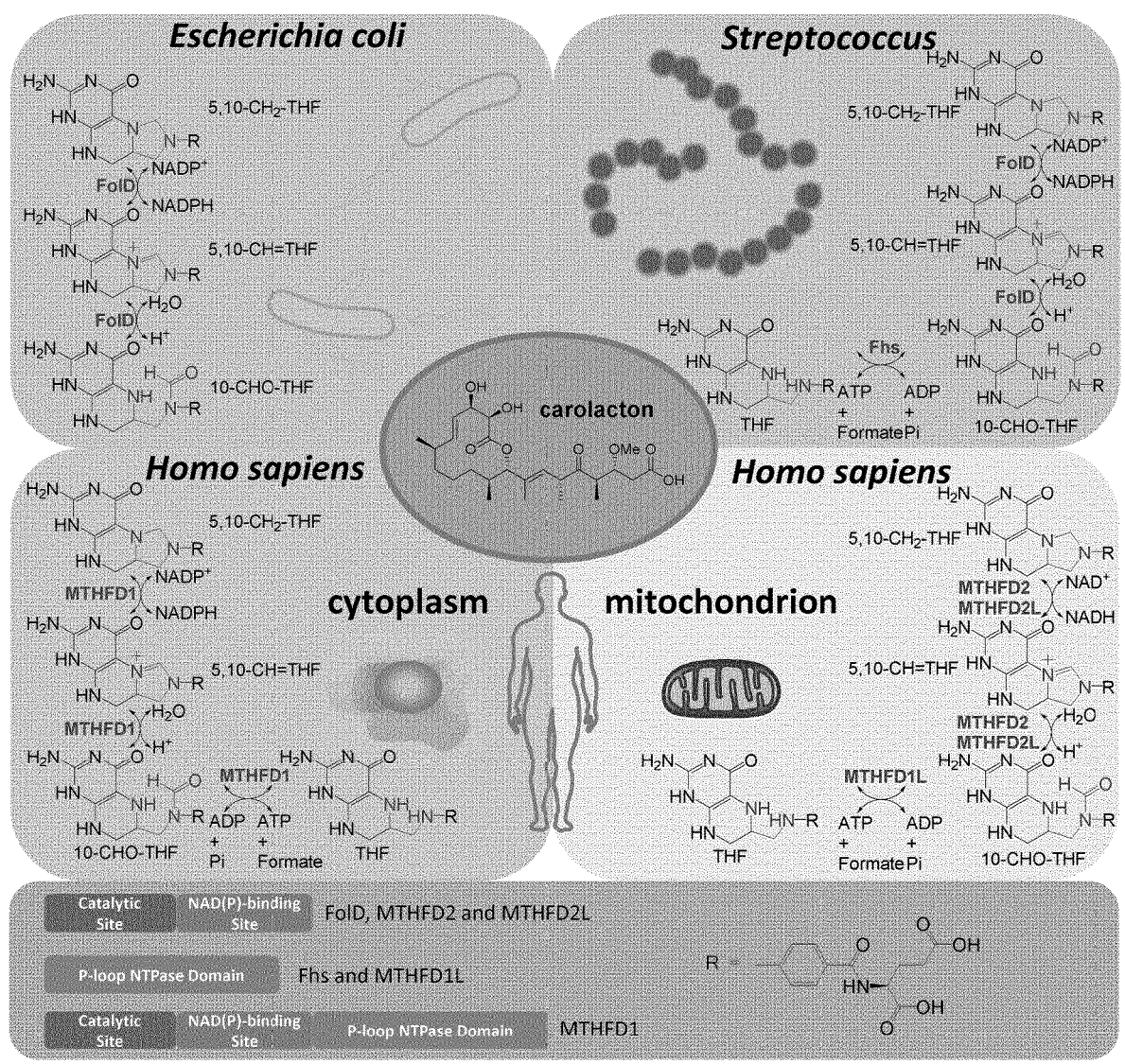

CAROLACTON AND DERIVATIVES THEREOF FOR USE IN THE TREATMENT OF CELL PROLIFERATION DISORDERS

The invention relates to chemical compounds that are useful in the treatment of diseases associated with an activity of a 5,10-methylenyltetrahydrofolate cyclohydrolase/5,10-methylene tetrahydrofolate dehydrogenase enzyme in pathological eukaryotic cells. In particular, the invention relates to compounds that exhibit inhibitory activity of 5,10-methylenyltetrahydrofolate cyclohydrolase/5,10-methylene tetrahydrofolate dehydrogenase enzymes and their use in the treatment of cancer and/or parasitic diseases.

BACKGROUND OF THE INVENTION

Folate (vitamin B9) is an essential cofactor in all cells, but it is synthesized only by bacteria and plants (Green et al., 2007). The folate-dependent C1 metabolism is highly conserved in all domains of life and it provides the key building blocks for growth, most importantly purines and pyrimidines for DNA and RNA synthesis, amino acids (serine, glycine, methionine, cysteine), provitamines (panthothenic acid) and formylated methionine tRNA for translation initiation (Ducker et al., 2017). A central position in the folate-dependent C1 metabolism is occupied by the dual function enzyme FoID: It catalyzes the reversible nicotinamide adenine dinucleotide phosphate ($NADP^+$)-dependent dehydrogenation step (5,10-methylenetetrahydrofolate (5,10-$CH_2$-THF) dehydrogenase (DH)) and the subsequent cyclohydrolysis step (5,10-methenyltetrahydrofolate (5,10-CH=THF) cyclohydrolase (CYH)) (FIG. 1) (Blakley et al., 1984).

The (bi-functional) enzyme 5,10-methylenyltetrahydrofolate cyclohydrolase/5,10-methylene tetrahydrofolate dehydrogenase is abbreviated FoID in bacteria, MTHFD in humans, and DHCH in protozoan parasites.

Potential of MTHFD as a Target in Cancer Therapy

In higher organisms such as humans, the cytosolic trifunctional protein MTHFDl, which has DH and CYH but also a formate tetrahydrofolate synthase (Fhs) domain, maintains the metabolism of methylene-, methenyl- and formyl-THF (10-CHO-THF) (Appling, 1991, Christensen et al., 2006, Christensen et al., 2008). In mitochondria, the DH and CYH activities are provided by FoID analogues MTHFD2 and MTHFD2L, while the Fhs activity is carried out by MTHFD1L (FIG. 1) Christensen et al., 2006, Christensen et al., 2008).

In cancer a rapid glycolysis as well as anabolic processes such as synthesis of amino acids, nucleotides and lipids is necessary in order to support rapid cell proliferation. In particular, cancer cells become dependent on one-carbon metabolism to support purine and thymidylate synthesis. The enzymes involved in folate-dependent C1 metabolism therefore represent powerful targets for the inhibition of fast growing cells and have been targeted by anticancer drugs. For example, clinically used methotrexate inhibits dihydrofolate reductase (Rajagopalan et al., 2002). MTHFD2 is one of the most highly upregulated enzymes during neoplastic transformation and upregulated across many cancers relative to normal tissues (Jain, et al., 2012). Furthermore genetic silencing of MTHFD2 and inhibition with small molecules slows proliferation across a number of cancer cell lines (Nilsson et al., 2014).

In addition, MTHFD2 is normally only expressed during embryonic development and not in adult tissues. MTHFD2 is therefore a promising tumor-selective therapeutic target.

Several studies have reported inhibitors of FoID analogues MTHFD1 or MTHFD2, some of which display in vivo activity against human cells (Schmidt et al., 2000, Tonkinson et al., 1998, Gustafsson et al., 2017). However, either poor activity was observed (e.g. LY345899, $IC_{50}$ 128 µM) or the compounds were unspecific (e.g. LY231514, which principally inhibits thymidylate synthase) (Tonkinson et al., 1998, McDonald et al., 1998, Shih et al., 1997). Moreover the known inhibitors exhibit an activity against purified enzymes, but are not cell permeable and thus not active in vivo. A further complication of the known inhibitor is that a stronger inhibition of the cytosolic MTHFD1 in comparison to mitochondrial MTHFD2 has been observed, which may increase undesired side effects (Schmidt et al., 2000).

The finding of new specific and more effective inhibitors of MTHFD2 could represent a powerful therapeutic strategy to reduce cancer cell growth and survival.

DHCH as Drug Target for Diseases Associated with Protozoan Parasites

*Leishmania* sp. and *Trypanosoma* sp. are eukaryotic protozoa that cause a number of tropical diseases, including sleeping sickness, Leishmaniasis, and Chagas disease (Stuart et al., 2008).

*Leishmania* is a genus of trypanosomes that cause the disease leishmaniasis. They are spread by sandflies. Their primary hosts are vertebrates; Leishmania commonly infects hyraxes, canids, rodents, and humans. Leishmaniasis currently affects 12 million people in 98 countries. About 2 million new cases occur each year, and 21 species are known to cause disease in humans. There are four main forms of Leishmaniasis. Cutaneous leishmaniasis is the most common form and visceral leishmaniasis is the most serious form in which the parasites migrate to the vital organs. Visceral leishmaniasis is primarily caused by the parasite *Leishmania donovani*, and is potentially fatal if untreated.

Previous studies have unraveled an essential role for the enzyme DHCH in *Leishmania major* (Murta et al., 2009). DHCH has therefore been assessed as a potential drug target, the tested synthetic inhibitors were however more toxic to the human cells than to the parasites, emphasizing the need for the development of novel inhibitors (Eadsforth et al., 2012c).

Chagas disease, also called American trypanosomiasis, is a tropical parasitic disease caused by the flagellate protozoan *Trypanosoma cruzi*. *T. cruzi* is commonly transmitted to humans and other mammals by the blood-sucking "kissing bugs" of the subfamily Triatominae (family Reduviidae). Chagas disease is contracted primarily in the Americas. It is endemic in twenty one Central and Latin American countries; particularly in poor, rural areas of Mexico, Central America, and South America. Each year, an estimated 10 to 15 million people across the world are infected with Chagas disease with an estimated 14,000 people dying as a consequence of the disease.

*Trypanosoma* is a genus of protozoa causing African trypanosomiasis, also known as sleeping sickness. It is an insect-borne parasitic disease of humans and other animals caused by protozoa of the species *Trypanosoma brucei*. There are two subspecies that infect humans, *T.b gambiense* and *T.b rhodesiense*, with the former accounting for over 95% of reported cases and the latter accounting for the remaining reported cases. The parasites are transmitted to humans by tsetse fly (Glossina genus) bites which have acquired their infection from human beings or from animals harboring the human pathogenic parasites.

The disease occurs regularly in some regions of sub-Saharan Africa with the population at risk being about 70 million in 36 countries. An estimated 11,000 people are currently infected with 2,800 new infections in 2015. In 2015 it caused around 3,500 deaths, down from 34,000 in 1990. More than 80% of these cases are in the Democratic Republic of the Congo. African trypanosomiasis symptoms occur in two stages. In the first stage, known as the haemolymphatic phase, the trypanosomes multiply in subcutaneous tissues, blood and lymph. The haemolymphatic phase is characterized by bouts of fever, headaches, joint pains and itching. In the second stage, the neurological phase, the parasites cross the blood-brain barrier to infect the central nervous system leading to a severe symptoms including confusion, sensory disturbances, poor coordination and sleeping disorder. Untreated, the disease is fatal with progressive mental deterioration leading to coma, systemic organ failure, and death.

Previously an essential function of the 5,10-methylenyltetrahydrofolate cyclohydrolase/5,10-methylene tetrahydrofolate dehydrogenase (DHCH) for growth in Trypanosomatidae has been reported. Inhibitors of the DHCH enzyme of *Trypanosoma brucei* have been tested and shown to be highly active against the purified enzyme, yet activity against the parasite in the bloodstream was modest (Eadsforth et al., 2015). The reduced therapeutic effect may be due to a lack of uptake by transporters. Also for the treatment of sleeping sickness and Chagas diseases a need for the development of improved inhibitors exists.

Known Roles of Carolacton

The secondary metabolite carolacton is a macrolide ketocarbonic acid, which is produced by the myxobacterium *Sorangium cellulosum* (Jansen et al., 2010). Carolacton was originally reported as a highly potent inhibitor of biofilm formation in the human pathogen *S. mutans* and the efflux pump mutant *Escherichia coli* ToIC (Jansen et al., 2010, Kunze et al., 2010). Later, growth inhibition of *S. pneumoniae* was also reported (Donner et al., 2016).

EP 2033642 A discloses the use of Carolacton as a medicament for the inhibition, reduction or prevention of bacterial biofilms. Stump et al. 2015 described the synthesis of derivatives of Carolacton and their activity in the treatment of biofilm associated infections. WO 02/099113 A1 disclosed an antifungal activity of Carolacton.

While the inhibitory function of Carolacton has been observed, the molecular target of carolacton remained elusive. Extensive time-resolved transcriptome analyses provided proteins essential for carolacton activity in *S. mutans*, e.g. the serine/threonine protein kinase PknB and the cysteine metabolism regulator CysR. However, none of these proteins could be verified as direct interaction partners of carolacton (Reck et al., 2011, Suhakar et al. 2014). Similarly, the molecular target was not found to be encoded by the genes strongly upregulated upon carolacton treatment in *S. pneumoniae* (Donner et al., 2016). Instead, the transcriptomic responses reflected defense reactions of the cells.

As described herein, the molecular target of carolacton has been identified by the inventors to be the bi-functional enzyme 5,10-methylenyltetrahydrofolate cyclohydrolase/5,10-methylene tetrahydrofolate dehydrogenase. Carolacton administration therefore represents an effective therapeutic approach for diseases associated with an expression and/or activity of bi-functional enzyme 5,10-methylenyltetrahydrofolate cyclohydrolase/5,10-methylene tetrahydrofolate dehydrogenase in pathological eukaryotic cells, in particular cancerous cells exhibiting an increased expression and/or activity of MTHDF2, or protozoan parasites for which DHCH is essential.

The therapeutic administration of carolacton for the treatment of these medical conditions has not been previously described.

SUMMARY OF THE INVENTION

In light of the prior art the technical problem underlying the present invention is to provide alternative and/or improved means for the treatment of diseases associated with activity of a 5,10-methylenyltetrahydrofolate cyclohydrolase/5,10-methylene tetrahydrofolate dehydrogenase enzyme in pathological eukaryotic cells, such as cancer, and tropical diseases caused by protozoan parasites, in particular sleeping sickness, Leishmaniasis, and Chagas disease.

This problem is solved by the features of the independent claims. Preferred embodiments of the present invention are provided by the dependent claims.

The invention relates to a compound according to Formula I for use as a medicament in the treatment of a disease associated with activity of a 5,10-methylenyltetrahydrofolate cyclohydrolase/5,10-methylene tetrahydrofolate dehydrogenase enzyme in pathological eukaryotic cells,

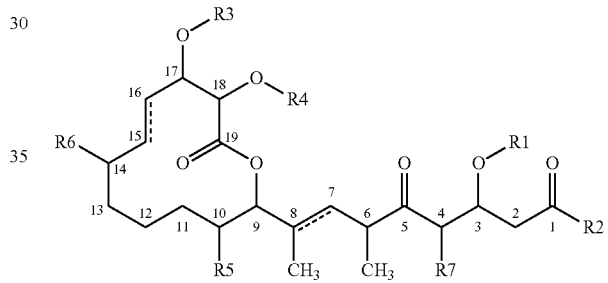

Formula I wherein
each of R1, R3 and R4 are independently selected from H, C1-C12 alkyl groups, including methyl, ethyl, n-propyl, isopropyl, n-butyl, isobutyl, n-heptyl, isoheptyl, n-pentyl- or isopentyl, n-hexyl, isohexyl, or C7-C12 linear, branched or cyclic, saturated, unsaturated or aromatic hydrocarbon radicals;

R2 is selected from H, C1-C12 alkyl groups, including methyl, ethyl, n-propyl, isopropyl, n-butyl, isobutyl, n-heptyl, isoheptyl, n-pentyl- or isopentyl, n-hexyl, isohexyl, C7-C12 linear, branched or cyclic, saturated, unsaturated or aromatic hydrocarbon radicals, or OR8, wherein R8 is selected from H, C1-C12 alkyl groups, including methyl, ethyl, n-propyl, isopropyl, n-butyl, isobutyl, n-heptyl, isoheptyl, n-pentyl- or isopentyl, n-hexyl, isohexyl, or C7-C12 linear, branched or cyclic, saturated, unsaturated or aromatic hydrocarbon radicals; and each of R5, R6 and R7 are independently selected from H or C1-C12 alkyl groups, including methyl, ethyl, n-propyl, isopropyl, n-butyl, isobutyl, n-heptyl, isoheptyl, n-pentyl- or isopentyl, n-hexyl, isohexyl.

It was previously unknown and entirely surprising that the compounds comprising a structure of formula I exhibit an inhibitory function against the bifunctional enzyme 5,10-methylenyltetrahydrofolate cyclohydrolase/5,10-methylene tetrahydrofolate dehydrogenase.

As unraveled by the inventors, and demonstrated in the examples herein, the compounds according to the formula I establish several hydrophobic interactions with the active site of the bifunctional enzyme 5,10-methylenyltetrahydrofolate cyclohydrolase/5,10-methylene tetrahydrofolate dehydrogenase. Whereas the binding of the compounds does not disrupt the overall structure of the bifunctional enzyme 5,10-methylenyltetrahydrofolate cyclohydrolase/5,10-methylene tetrahydrofolate dehydrogenase, it leads to a partial dissolution of a functional α-helix unit of the enzyme. Thereby the binding of compounds according to Formula I to the bifunctional enzyme 5,10-methylenyltetrahydrofolate cyclohydrolase/5,10-methylene tetrahydrofolate dehydrogenase appears to impede the interaction with the substrate 10-CH$_2$-THF as well as cofactors NADP$^+$ or NAD$^+$.

The bifunctional enzyme 5,10-methylenyltetrahydrofolate cyclohydrolase/5,10-methylene tetrahydrofolate dehydrogenase is a key catalytic factor in the folate-dependent one-carbon pathway and a potent target for therapy of multiple diseases.

In particular, MTHDF2 expression appears to be elevated in a variety of cancers (Nilsson et al., 2014). As detailed below, the compounds according to formula I inhibit cancer cell proliferation in various cancer cell types. Unlike previously described inhibitors for MTHDF2 the compounds according to formula I are further distinguished by an excellent cell permeability. Inhibition of the dual activity of the enzyme could not only be verified in in-vitro assays for purified proteins, but also importantly in cellulo assays for various cancer types. IC50 values in the lower nanomolar range support the therapeutically effective inhibition of the compounds according to formula I. Moreover the compounds are characterized by a low toxicity against non-cancerous cells, thus likely minimizing side effects at therapeutically effective doses.

In a preferred embodiment the invention relates to compounds as disclosed herein for use as a medicament, wherein the disease to be treated is a mammalian cell proliferation disorder, preferably cancer.

In a further preferred embodiment the invention relates to compounds as disclosed herein for use as a medicament, wherein the disease is a cancer and the eukaryotic pathological cells are cancerous cells in which the activity of enzyme 5,10-methylenyltetrahydrofolate cyclohydrolase/5,10-methylene tetrahydrofolate dehydrogenase is increased in comparison to a suitable control, for example non-cancerous control cells.

In a further preferred embodiment the invention relates to compounds as disclosed herein for use as a medicament, wherein the cancer is a lymphoma, a leukemia, a colon cancer, an ovary cancer or a gastric cancer.

Advantageously, the inhibitory activity of the compounds as disclosed herein, does not only allow for a treatment of cancerous diseases, but of a variety of diseases that are associated with an activity of the bifunctional enzyme 5,10-methylenyltetrahydrofolate cyclohydrolase/5,10-methylene tetrahydrofolate dehydrogenase in pathological eukaryotic cells. This includes in particular, parasitic diseases caused by protozoan parasites.

As proven in previous publications DHCH is essential for a number of protozoan parasites including *Trypanosoma brucei* and *Leishmania major* (Eadsforth et al. 2012c, Eadsforth et al. 2015) The inhibitory function of the compounds disclosed herein on DHCH therefore enables a use of the compounds as a medicament in the treatment of parasitic diseases. Due to a low toxicity and high specificity, the compounds may effectively reduce and/or reverse the progression of the parasitic diseases by inhibiting proliferation of the parasites without severely effecting human cells of the endogenous organism.

In a further preferred embodiment the invention relates to compounds as disclosed herein for use as a medicament, wherein the pathological eukaryotic cells are protozoan parasites and the disease is a parasitic disease preferably selected from the group consisting of sleeping sickness, Leishmaniasis, and Chagas disease.

In a further preferred embodiment the compound for use as a medicament according to any one of the formulae described herein is characterized in that the bond connecting C-15 and C-16 is hydrogenated to a single bond and C-15 and C-16 are saturated with hydrogen atoms and/or wherein the bond connecting C-7 and C-8 is hydrogenated to a single bond and C-7 and C-8 are saturated with hydrogen atoms.

In a preferred embodiment of the invention the compound for use as a medicament is according to Formula II

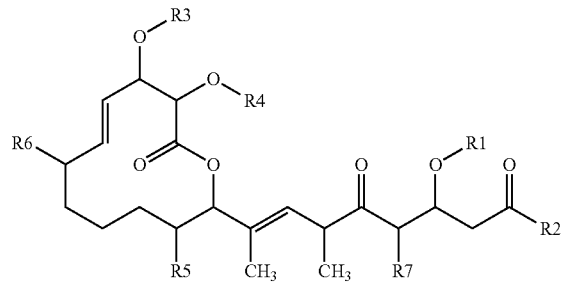

Formula II wherein R1-R7 are as for Formula I.

In a preferred embodiment of the invention the compound for use as a medicament is according to Formula III

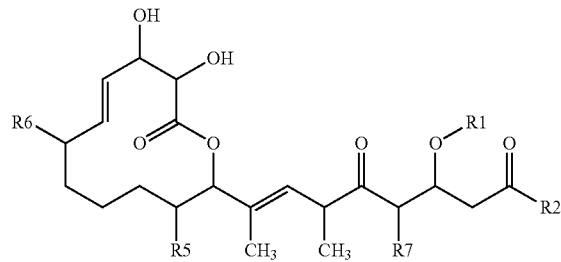

Formula III wherein

R1 is selected from H, C1-C12 alkyl groups, including methyl, ethyl, n-propyl, isopropyl, n-butyl, isobutyl, n-heptyl, isoheptyl, n-pentyl- or isopentyl, n-hexyl, isohexyl, or C7-C12 linear, branched or cyclic, saturated, unsaturated or aromatic hydrocarbon radicals;

R2 is selected from H, C1-C12 alkyl groups, including methyl, ethyl, n-propyl, isopropyl, n-butyl, isobutyl, n-heptyl, isoheptyl, n-pentyl- or isopentyl, n-hexyl, isohexyl, C7-C12 linear, branched or cyclic, saturated, unsaturated or aromatic hydrocarbon radicals, or OR8, wherein R8 is selected from H, C1-C12 alkyl groups, including methyl, ethyl, n-propyl, isopropyl, n-butyl, isobutyl, n-heptyl, isoheptyl, n-pentyl- or isopentyl, n-hexyl, isohexyl, or C7-C12 linear, branched or cyclic, saturated, unsaturated or aromatic hydrocarbon radicals; and each of R5, R6 and R7 are independently selected from H or C1-C12 alkyl groups, including methyl, ethyl, n-propyl, isopropyl, n-butyl, isobutyl, n-heptyl, isoheptyl, n-pentyl- or isopentyl, n-hexyl, isohexyl.

In a preferred embodiment of the invention the compound for use as a medicament is according to Formula IV Formula IV

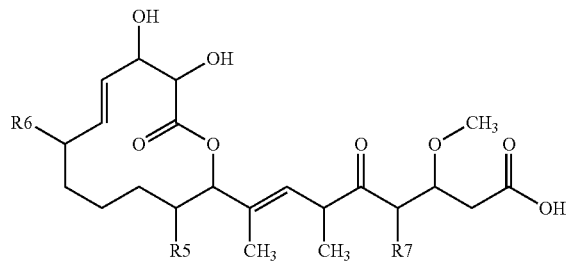

wherein each of R5, R6 and R7 are independently selected from H or C1-C12 alkyl groups, including methyl, ethyl, n-propyl, isopropyl, n-butyl, isobutyl, n-heptyl, isoheptyl, n-pentyl- or isopentyl, n-hexyl, isohexyl.

In a further preferred embodiment the compound for use as a medicament according to any one of the formulae described herein is characterized in that the carbonyl group of C-5 is reduced to a hydroxyl group.

In a preferred embodiment of the invention the compound for use as a medicament is carolacton according to Formula V Formula V

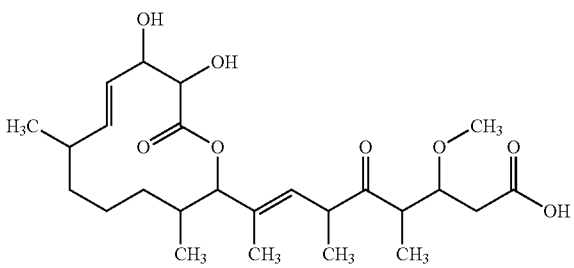

In a further preferred embodiment the invention relates to a compound for use as a medicament according to Formulae VI, VII, VIII, IX, X or XI Formula VI

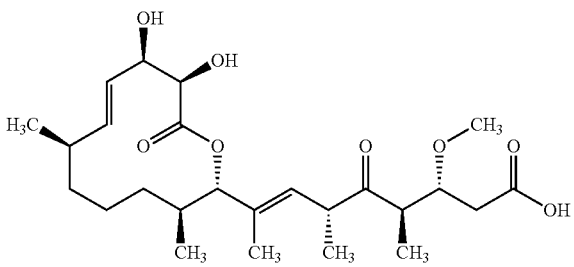

Formula VII

Formula VIII

Formula IX

Formula X

Formula XI

In a further aspect of the invention the compound for use as a medicament according to any one of the formulae described herein is provided in the form of a pharmaceutical composition for the treatment of a disease associated with an activity of 5,10-methylenyltetrahydrofolate cyclohydrolase/ 5,10-methylene tetrahydrofolate dehydrogenase enzyme in pathological eukaryotic cells, wherein the composition comprise a pharmaceutically acceptable carrier.

In a further preferred embodiment the invention relates to an in vitro use of a compound according to any of the formulae described herein in an assay for inhibition of the activity of 5,10-methylenyltetrahydrofolate cyclohydrolase/5,10-methylene tetrahydrofolate dehydrogenase, comprising bringing said compound into contact with said 5,10-methylenyltetrahydrofolate cyclohydrolase/5,10-methylene tetrahydrofolate dehydrogenase and subsequently assessing enzymatic activity.

In a further preferred embodiment the invention relates to an in vitro method comprising use of a compound according to any of the formulae described herein as a lead compound for the production of further derivatives that exhibit bifunctional enzyme 5,10-methylenyltetrahydrofolate cyclohydrolase/5,10-methylene tetrahydrofolate dehydrogenase inhibitory activity, said method comprising producing a structural derivative of one or more compounds according to any of the formulae described herein and subsequently assessing the inhibitory activity of said derivative on the bifunctional enzyme 5,10-methylenyltetrahydrofolate cyclohydrolase/5,10-methylene tetrahydrofolate.

Any one of the compounds disclosed herein may be produced by total or partial chemical synthesis or by derivatization of carolacton. Carolacton may be obtained by fermentation and isolation from a fermentation broth as known to the person skilled in the art (see e.g. WO 20091030773A1) or by a total synthesis for instance according to Schmidt et al., 2012. Derivatization reactions for producing derivatives of the compounds disclosed herein are known to a person skilled in the art. For conducting the derivatization reactions the person skilled in the art may also rely on standard literature such as the Handbook of Analytical Derivatization Reactions by D. Knapp, John Wiley & Sons, Ltd, 1979, 741 pp. The reviews of Zongru G. 2017 and Altmann 2011 provide further guidelines for the person skilled for derivatization or semisynsthesis of natural products. Note that Altmann 2011 illustrates semisynthesis and diversity with Epithilone as an example. Since Epothilone belongs to the same class of natural products, the polyketides, as Carolacton the article represents a particularly useful guideline for a person skilled in the art for a chemical synthesis or derivatization of Carolacton. Furthermore, the compounds disclosed herein can also be generated using chemical synthesis or derivatization methods as described in Stumpp et al. 2015, Jansen et al. 2010, Reck et al. 2011 or Ammermann et al. 2017.

The in vitro methods disclosed herein allow for an identification of further therapeutically effective compounds, wherein compounds that exhibit a particular inhibitory activity on the enzymatic activity of 5,10-methylenyltetrahydrofolate cyclohydrolase/5,10-methylene tetrahydrofolate dehydrogenase are selected. In the activity assay is preferred to use as the bifunctional enzyme any one of MTHFD2, MTHFD2L, MTHFD1, DHCH and/or FoID. Assays for assessing the inhibitory activity of a substance against 5,10-methylenyltetrahydrofolate cyclohydrolase/5,10-methylene tetrahydrofolate dehydrogenase activity are known in the art. To this end dehydrogenase and cyclohydrolase activities may be determined for the enzymes for different concentrations of the compounds. As detailed below (Materials and Methods used in the Examples: Enzyme assay conditions) the dehydrogenase activity of the enzyme may be assayed for its substrate 5,10-$CH_2$-THF and cofactors NADP (e.g. for FoID) and NAD (e.g. for MTHFD2) by monitoring the formation of 5,10-CH=THF. Cyclohydrolase activity of the enzyme for its substrate 5,10-CH=THF may be assayed by monitoring the hydrolysis of 5,10-$CH_2$-THF.

DETAILED DESCRIPTION OF THE INVENTION

All cited documents of the patent and non-patent literature are hereby incorporated by reference in their entirety.

The present invention is directed to the treatment of a subject afflicted by disease(s) associated with an enzymatic activity of 5,10-methylenyltetrahydrofolate cyclohydrolase/5,10-methylene tetrahydrofolate dehydrogenase in eukaryotic pathological cells by administering the compounds disclosed herein. The term "subject" includes both human and veterinary subjects. The term "treatment" refers to a therapeutic intervention that ameliorates a sign or symptom of a disease or pathological condition after it has begun to develop. As used herein, the term "ameliorating", with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease The present invention encompasses both treatment and prophylactic treatment of a subject. A "prophylactic" treatment is a treatment administered to a subject who does not exhibit signs of a disease or exhibits only early signs for the purpose of decreasing the risk of developing pathology.

The present invention relates further to pharmaceutically acceptable salts of the compounds described herein. The term "pharmaceutically acceptable salt" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. Any chemical compound recited in this specification may alternatively be administered as a pharmaceutically acceptable salt thereof.

"Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The term "alkyl" refers to a branched or unbranched saturated hydrocarbon group of preferably 1 to 24 carbon atoms, such as methyl, ethyl, n-propyl, isopropyl, w-butyl, isobutyl, f-butyl, pentyl, hexyl, heptyl, octyl, decyl, tetradecyl, hexadecyl, eicosyl, tetracosyl and the like. Preferred alkyl groups have 1 to 12 carbon atoms, 1 to 6 carbon atoms, more preferably 1 to 4 carbon atoms. Any one or more of the alkyl groups described herein may be "substituted alkyls", wherein one or more hydrogen atoms are substituted with a substituent such as halogen, cycloalkyl, alkoxy, amino, hydroxyl, aryl, or carboxyl.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment (such as O-alkyl). An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cclopropoxy, cyclohexyloxy, and the like.

"Carbonyl" refers to a radical of the formula —C(O)—. Carbonyl-containing groups include any substituent containing a carbon-oxygen double bond (C=O), including acyl groups, amides, carboxyl groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carboxyl" refers to a —COON radical. Substituted carboxyl refers to —COOR where R is aliphatic, heteroaliphatic, alkyl, heteroalkyl, or a carboxylic acid or ester.

The term "hydroxyl" is represented by the formula —OH.

A dotted line in the position of a double bond represents an optional double bond, which may be present or absent.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999. In general, protecting groups are removed under conditions which will not affect the remaining portion of the molecule. These methods are well known in the art and include acid hydrolysis, hydrogenolysis and the like.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention.

Disclosed herein are compounds that are antagonists of bifunctional enzyme 5,10-methylenyltetrahydrofolate cyclohydrolase/5,10-methylene tetrahydrofolate dehydrogenase in that they inhibit the enzymatic catalysis of the $NADP^+$- or $NAD^+$-dependent dehydrogenation step on 5,10-$CH_2$-THF and/or of the subsequent cyclohydrolysis step on 5,10-CH=THF. By inhibiting the cyclohydrolase and/or the dehydrogenase activity of the enzyme, the compound interferes with essential steps of the folate-dependent one-carbon pathway. In cancer cell proliferation as well as in the proliferation of protozoan parasites the de novo biosynthesis of nucleotides is mediated through said pathway. Therefore the interference of the compounds described herein with the cyclohydrolase and/or dehydrogenase enzymatic activity allows for an effective treatment of these diseases.

The bifunctional 5,10-methylenyltetrahydrofolate cyclohydrolase/5,10-methylene tetrahydrofolate dehydrogenase enzyme is highly conserved between different species in particular in respect to the domains mediating cyclohydrolase and dehydrogenase activity.

In humans, MTHFD2 is a bifunctional enzyme, localized to the mitochondria, that catalyzes both the dehydrogenase and cyclohydrolase reactions. Cofactors for MTHFD2 include NAD+, Mg2+, and inorganic phosphate. MTHFD2 is expressed in embryonic growth and in the transformed state (Mejia et al., 1985). The sequence of human MTHFD2 is available in GenBank at Accession Nos. NM 006636.3 (nucleic acid) and NP 006627.2 (protein).

MTHFD1 is a trifunctional enzyme, localized to the cytosol, that exhibits the bifunctional activity to catalyzes the dehydrogenase, cyclohydrolase as well as the formyl-THF synthetase reactions. Cofactors for MTHFD1 include NADP+. The sequence of human is available in GenBank at Accession Nos. MTHFD1 NM 005956.3 (nucleic acid) and NP 005947.3 (protein).

MTHFD2L is a bifunctional enzyme, localized to the mitochondria, that catalyzes both the dehydrogenase and cyclohydrolase reactions. Cofactors for MTHFD2L include NADP+. The sequence of human MTHFD2L is available in GenBank at Accession Nos. NM 001144978.1 (nucleic acid) and NP 001138450.1 (protein).

In protozoan parasites the 5,10-methylenyltetrahydrofolate cyclohydrolase/5,10-methylene tetrahydrofolate dehydrogenase enzyme is abbreviated as DHCH.

*Leishmania major* possess a single DHCH1 gene encoding for the enzyme that is essential for the catalysis of 5,10-$CH_2$-THF to 10-CHO-THF in the one-carbon metabolism. The sequence of DHCH in *Leishmania major* strain Friedlin is available in GenBank at Accession Nos. XM_001683987.1 (nucleic acid) and XP_001684039.1 (protein).

In Trypanosomatidae the gene encoding for 5,10-methylenyltetrahydrofolate cyclohydrolase/5,10-methylene tetrahydrofolate dehydrogenase (DHCH) is essential for growth. The sequence can be accessed in Genedb (http://www-.genedb.org, accession number Tb927.7.1600). In a functional study of 5,10-methylenyltetrahydrofolate cyclohydrolase/5,10-methylene tetrahydrofolate dehydrogenase in *Trypanosoma brucei* the enzyme has also been abbreviated TbFolD (Eadsforth et al., 2015).

Due to the conserved structure of the 5,10-methylenyltetrahydrofolate cyclohydrolase/5,10-methylene tetrahydrofolate dehydrogenase enzyme the compounds described herein advantageously target MTHFD2, MTHFD1, MTHFD2L, FoID and DHCH.

The compounds described herein are used in the treatment of subjects afflicted by a disease associated with enzymatic activity of 5,10-methylenyltetrahydrofolate cyclohydrolase/5,10-methylene tetrahydrofolate dehydrogenase in pathological eukaryotic cells.

As used herein the term "pathological eukaryotic cells" refers to eukaryotic cells that due a pathological presence and/or proliferation cause diseases in afflicted subjects. In a preferred embodiment the invention relates to inhibition of proliferation of pathological eukaryotic cells in which 5,10-methylenyltetrahydrofolate cyclohydrolase/5,10-methylene tetrahydrofolate dehydrogenase activity is evident. The pathological eukaryotic cells may be endogenous cells of the subject that have undergone a transformation to a cell proliferation disorder, as may be the case for cancerous cells. However the pathological eukaryotic cells may also refer to cells exogenous to the subject, as is the case for protozoan parasites. In the latter case, proliferation of the parasites as such are considered the cause of the disease, such that the parasites are the pathological eukaryotic cells to be targeted.

A "disease associated with the activity of 5,10-methylenyltetrahydrofolate cyclohydrolase/5,10-methylene tetrahydrofolate dehydrogenase activity in pathological eukaryotic cells" refers in a preferred embodiment to a medical condition in which pathological eukaryotic cells cause a disease within an afflicted subject and wherein the pathological eukaryotic cells exhibit a 5,10-methylenyltetrahydrofolate cyclohydrolase/5,10-methylene tetrahydrofolate dehydrogenase activity.

The diseases treatable by the compounds described herein preferably refer to diseases wherein the proliferation and/or the metabolism of the pathological eukaryotic cells depends on the activity of 5,10-methylenyltetrahydrofolate cyclohydrolase/5,10-methylene tetrahydrofolate dehydrogenase activity.

A number of methods known in the art can be used to assess whether the pathological eukaryotic cells exhibit 5,10-methylenyltetrahydrofolate cyclohydrolase/5,10-methylene tetrahydrofolate dehydrogenase activity. This may include the detection of levels of a protein, mRNA, or enzyme activity for the purposes of the present invention. For example, in some of the methods described herein, the level, presence or absence of protein, mRNA, or activity of the bifunctional enzyme 5,10-methylenyltetrahydrofolate cyclohydrolase/5,10-methylene tetrahydrofolate dehydrogenase, such as MTHFD2, is determined in a sample from a subject afflicted by the disease.

In some embodiments, the level of mRNA (transcript) can be evaluated using methods known in the art, e.g., Northern blot, RNA in situ hybridization (RNA-ISH), RNA expression assays, e.g., microarray analysis, RT-PCR, RNA sequencing (e.g., using random primers or oligoT primers), deep sequencing, cloning, Northern blot, and amplifying the transcript, e.g., using quantitative real time polymerase chain reaction (qRT-PCR). Analytical techniques to determine RNA expression are known. See, e.g., Sambrook et al, Molecular Cloning: A Laboratory Manual, 3rd Ed., Cold Spring Harbor Press, Cold Spring Harbor, N.Y. (2001).

Any method known in the art can be used for detecting the presence of proteins (e.g., using one or more antibodies that specifically to the bifunctional enzyme 5,10-methylenyltetrahydrofolate cyclohydrolase/5,10-methylene tetrahydrofolate dehydrogenase). For example, a sample can be contacted with one or more antibodies or antigenic portions thereof that specifically bind to the 5,10-methylenyltetrahydrofolate cyclohydrolase/5,10-methylene tetrahydrofolate dehydrogenase, such as MTHFD2; the binding of the one or more antibodies to proteins present in the sample can be detected using methods known in the art. Antibodies that bind specifically to 5,10-methylenyltetrahydrofolate cyclohydrolase/5,10-methylene tetrahydrofolate dehydrogenase, such as MTHFD2, are known in the art and commercially available, e.g., from AbD Serotec; Thermo Fisher Scientific, Inc.; Proteintech Group; Biorbyt; NovaTeinBio; Aviva Systems Biology; United States Biological; Creative Biomart; Fitzgerald; Novus Biologicals; R&D Systems; and Abeam.

Where desired, any protein isolation methods described herein or known in the art can be used before the sample is contacted with the antibody or antigenic portion thereof.

Methods for detecting binding of the antibodies to target proteins are known in the art, and can include the use of secondary antibodies. The secondary antibodies are generally modified to be detectable, e.g., labeled. The term "labeled" is intended to encompass direct labeling by coupling (i.e., physically linking) a detectable substance to the secondary antibody, as well as indirect labeling of the multimeric antigen by reactivity with a detectable substance. Examples of detectable substances include various enzymes, prosthetic groups, fluorescent materials, luminescent materials, bio luminescent materials, and radioactive materials. Examples of suitable enzymes include horseradish peroxidase (HRP), alkaline phosphatase, P-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, and quantum dots, dichlorotriazinylamine fluorescein, dansyl chloride, and phycoerythrin; an example of a luminescent material includes luminol; examples of bio luminescent materials include green fluorescent protein and variants thereof, luciferase, luciferin, 125 131 35 and aequorin; and examples of suitable radioactive material include I, I, S, or $^3$H. Methods for producing such labeled antibodies are known in the art, and many are commercially available.

Any method of detecting proteins present in a sample can be used, including but not limited to radioimmunoassays (RIA), enzyme-linked immunosorbent assays (ELISA), Western blotting, surface plasmon resonance, micro fluidic devices, protein array, protein purification (e.g., chromatography, such as affinity chromatography), mass spectrometry, two-dimensional gel electrophoresis, or other assays as known in the art.

In some embodiments of the methods described herein, an assay comprises providing one or more antibodies that specifically bind to the bifunctional enzyme 5,10-methylenyltetrahydrofolate cyclohydrolase/5,10-methylene tetrahydrofolate dehydrogenase such as MTHFD2, contacting the antibodies with a sample comprising proteins from a cancerous cell from the subject, and the binding of the antibodies to the bifunctional enzyme 5,10-methylenyltetrahydrofolate cyclohydrolase/5,10-methylene tetrahydrofolate dehydrogenase proteins present in the sample can be detected.

Alternatively, an assay can comprise providing one or more nucleic acid probes that specifically bind to the bifunctional enzyme 5,10-methylenyltetrahydrofolate cyclohydrolase/5,10-methylene tetrahydrofolate dehydrogenase mRNA, contacting the nucleic acid probes with the sample comprising nucleic acids from a cancerous cell from the subject, and the binding of the probes to any bifunctional enzyme 5,10-methylenyltetrahydrofolate cyclohydrolase/5,10-methylene tetrahydrofolate dehydrogenase mRNA present in the sample can be detected.

In some embodiments, high throughput methods, e.g., protein or gene chips as are known in the art (see, e.g., Ch. 12, "Genomics," in Griffiths et al, Eds. Modern genetic Analysis, 1999,W. H. Freeman and Company; Ekins and Chu, Trends in Biotechnology, 1999;17:217-218; MacBeath and Schreiber, Science 2000, 289(5485): 1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of satellites or SCG.

In some embodiments, assays that detect bifunctional enzyme 5,10-methylenyltetrahydrofolate cyclohydrolase/5,10-methylene tetrahydrofolate dehydrogenase activity, e.g., in tumor samples, can be used. Any assay known in the art or described herein can be used. For example, to measure MTHFD2 activity in vitro, enzyme immunohistochemistry, e.g., an assay of NAD-dependent methylenetetrahydrofolate dehydrogenase activity as known in the art can be used. Enzymatic activity can also be deduced from the mRNA expression levels in the pathological eukaryotic cells, for instance in comparison to control cells.

In particular MTHDF2 shows a marked elevation of the mRNA expression across a variety of cancer types (Nilsson et al., 2014). Inhibition of the MTHDF2 by an administration of the compounds described herein may allow for reduction, inhibition or reversion of tumor growth.

In a preferred embodiment the disease associate with a 5,10-methylenyltetrahydrofolate cyclohydrolase/5,10-methylene tetrahydrofolate dehydrogenase activity of pathological eukaryotic cells refers to a cancer associated with a 5,10-methylenyltetrahydrofolate cyclohydrolase/5,10-methylene tetrahydrofolate dehydrogenase activity, preferably MTHDF2 activity, of the cancerous cells. MTHDF2 activity may be detected by the methods as described. In particular MTHDF2 activity of cancerous cells can determine by measuring mRNA expression or protein expression within the cells types as disclosed in Nilsson et al., 2014. Using protein expression as reference for MTHDF2 activity Nilsson et al., 2014 showed that bladder cancer, breast cancer, cervix cancer, colon cancer, uterine cancer, liver cancer, lung cancer, melanoma, ovarian cancer, renal cancer, testicular cancer or stomach cancer exhibited strong or moderate MTHFD2 activity. These type of cancers are thus preferred examples of diseases associate with a 5,10-methylenyltetrahydrofolate cyclohydrolase/5,10-methylene tetrahydrofolate dehydrogenase activity of pathological eukaryotic cells.

In a preferred embodiment the invention relates to the use of the compounds disclosed herein as a medicament in the treatment and/or prevention of a cancer.

In a preferred embodiment the cancer or tumor being treated or prevented is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lympharigioma, lymphangiomyoma, lymphangiosarcoma; pinealoma; cystosarcoma phylloides; hemangiosarcoma; lymphangiosarcoma; myxosarcoma, ovarial carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

A particularly preferred group of tumor treatable by the compounds disclosed herein comprise malignant lymphoma, lymphoma, leukemia, colon cancer, ovary cancer and gastric cancer. These cancer types are characterized by a 5,10-methylenyltetrahydrofolate cyclohydrolase/5,10-methylene tetrahydrofolate dehydrogenase activity of the cancerous cells such that the administration of the compounds disclosed inhibits or reduces cancer cell proliferation (see also e.g. Table 6).

invention relates to the use of the compounds disclosed herein as a medicament in the treatment and/or prevention of a cancer.

A used herein the term "parasitic disease" preferably refers to an infectious disease caused or transmitted by a (eukaryotic) protozoan parasite. In preferred embodiments the parasites are kinetoplastids, wherein kinetoplastids are a group of flagellated protozoans that are distinguished by the presence of a DNA-containing region, known as a "kinetoplast," in their single large mitochondrion (Stuart et al., 2008).

In one embodiment the parasitic disease is Leishmaniasis caused by the parasites *Leishmania donovani, Leishmania infantum, Leishmania braziliensis, Leishmania panamensis, Leishmania guayanensis, Leishmania amazonensis, Leish-*

*mania mexicana, Leishmania tropica, Leishmania major*. In one variation of the above embodiment, the disease being treated is Visceral leishmaniasis, caused by the parasite *Leishmania donovani*.

In a further embodiment the parasitic disease is Human African Trypanosomiasis (HAT, sleeping sickness) caused by a protozoa belonging to the species *Trypanosoma brucei*. In one embodiment, the protozoa is *Trypanosoma brucei gambiense*. In another embodiment, the protozoa is Trypanosoma brucei rhodesiense.

In yet another embodiment the parasitic disease is Chagas disease (American Trypanosomiasis) caused by protozoa *Trypanosoma cruzi*.

As used herein, the term "inhibitor" is defined as a compound that binds to and/or inhibits bifunctional enzyme 5,10-methylenyltetrahydrofolate cyclohydrolase/5,10-methylene tetrahydrofolate dehydrogenase with measurable affinity. In certain embodiments, an inhibitor has an IC50 and/or binding constant of less than about 100 µM, less than about 50 µM, less than about 1 µM, less than about 500 nM, less than about 100 nM, less than about 10 nM, or less than about 1 nM.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The pharmaceutical compositions can be administered to subjects by a variety of administration modes, either mucosal or non-mucosal, including by oral, rectal, intraocular, intranasal, intrapulmonary, or transdermal delivery, or by topical delivery to other surfaces. Optionally, the compositions can be administered by intramuscular, intraocular, subcutaneous, intravenous, intra-arterial, intra-articular, intraperitoneal, intrathecal, intracerebroventricular, or parenteral routes.

The compositions of the disclosure can alternatively contain as pharmaceutically acceptable carrier substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g. tablets).

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The present invention also relates to a method of treatment of subjects suffering from the various medical conditions disclosed herein. The method of treatment comprises preferably the administration of a therapeutically effective amount of a compound disclosed herein to a subject in need thereof.

A "therapeutically effective amount" refers to a quantity of a specified agent sufficient to achieve a desired effect in a subject being treated with that agent. For example, this may be the amount of a compound disclosed herein useful in treating a disease of the thyroid in a subject. The therapeutically effective amount or diagnostically effective amount of an agent will be dependent on the subject being treated, the severity of the affliction, and the manner of administration of the therapeutic composition. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.001 mg/kg body weight to 50 mg/kg body weight, 0.01 mg/kg body weight to about 20 mg/kg body weight, such as about 0.05 mg kg to about 5 mg/kg body weight, or about 0.2 mg/kg to about 2 mg/kg body weight.

The instant disclosure also includes kits, packages and multi-container units containing the herein described pharmaceutical compositions, active ingredients, and/or means for administering the same for use in the prevention and treatment of diseases and other conditions in mammalian subjects.

FIGURES

The following figures are presented in order to describe particular embodiments of the invention, by demonstrating a practical implementation of the invention, without being limiting to the scope of the invention or the concepts described herein.

Short description of the figures:

FIG. 1: The enzymatic routes to synthesize 10-CHO-THF in different organisms and the chemical structure of the FoID inhibitor carolacton.

Figure 2:
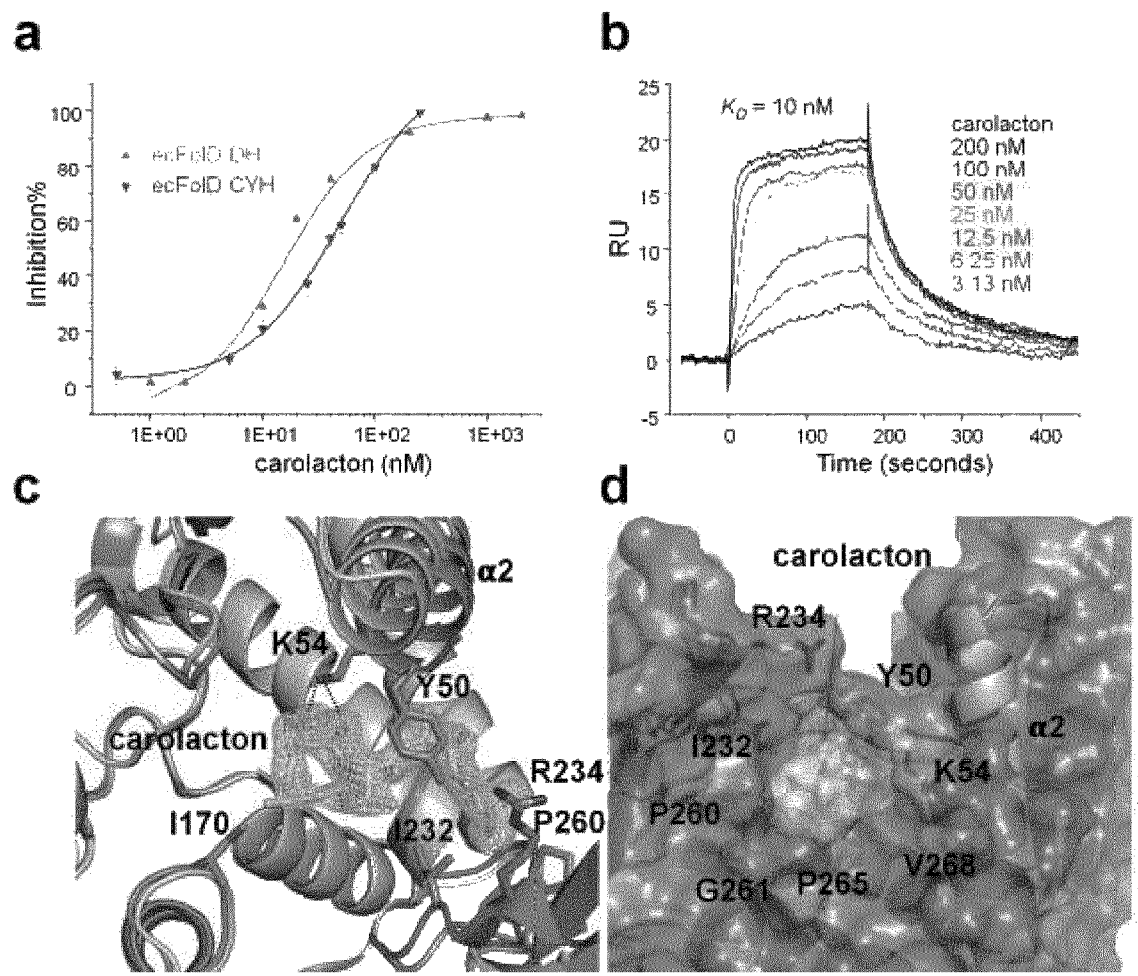

FIG. 2: Carolacton is a potent and tightly binding inhibitor of FoID.

Figure 3:
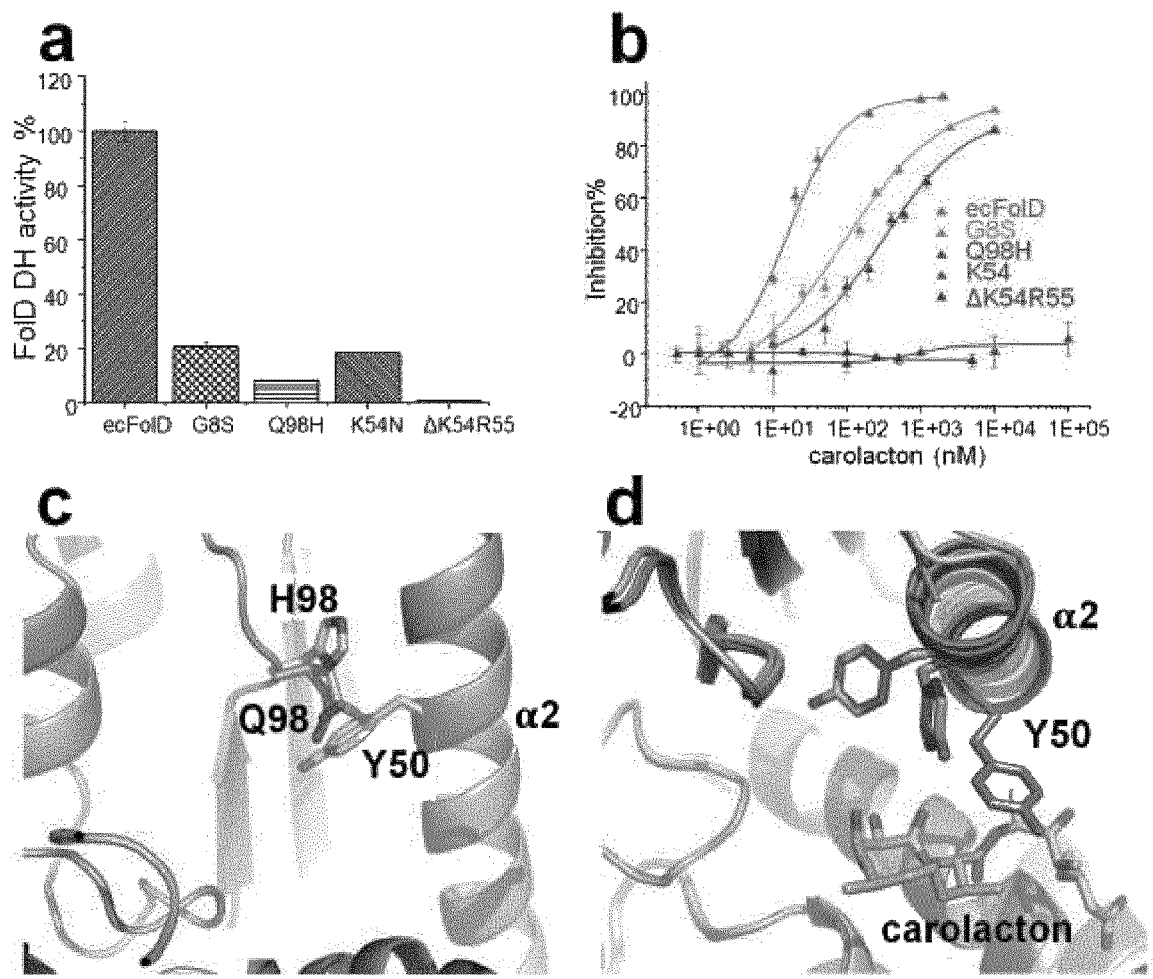

FIG. 3: The inhibition of carolacton to FoID dehydrogenase activity is either attenuated or abolished upon mutations which cause the attenuation of DH activity.

Figure 4:
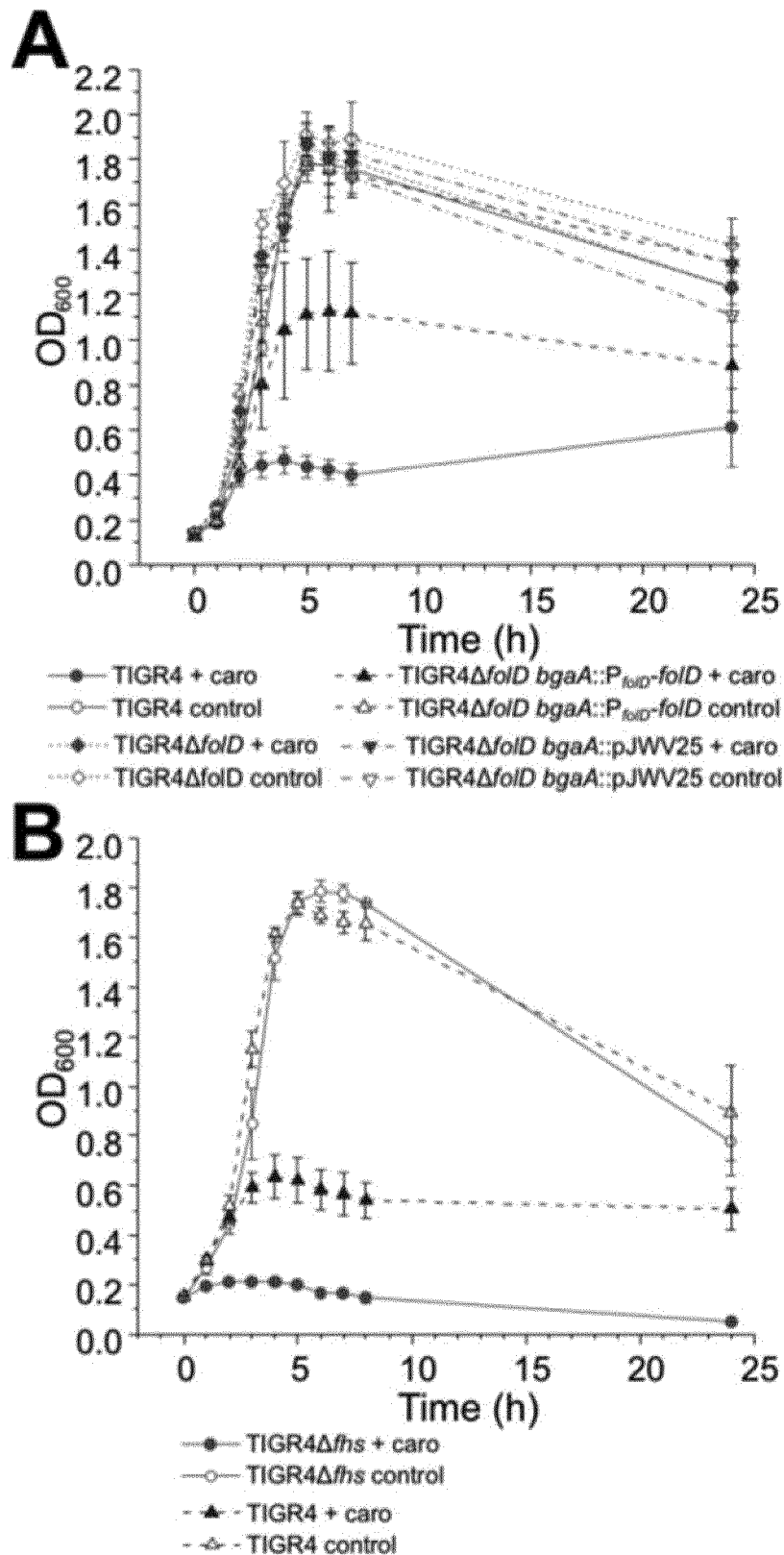

FIG. 4: Carolacton effects on S. pneumoniae TIGR4 and foID deletion, complementation and fhs deletion mutants.

Figure 5:
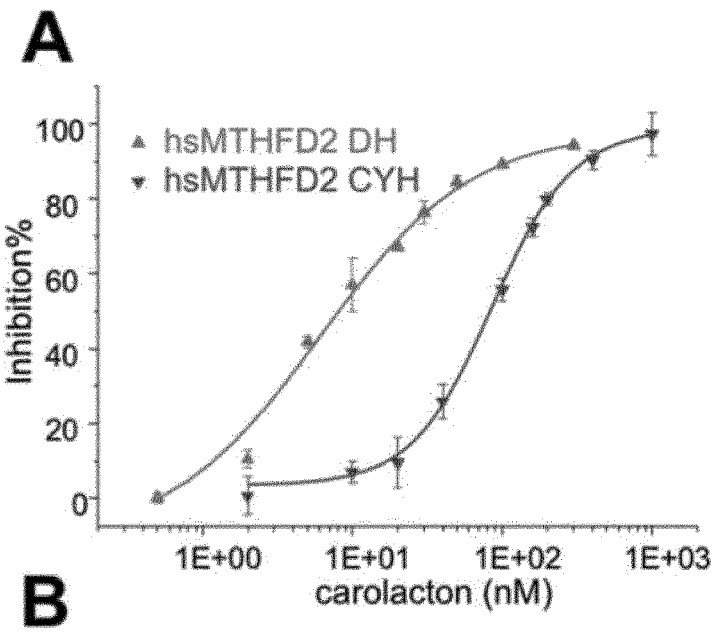

FIG. 5: Carolacton effects on hsMTHFD2

Figure 6:
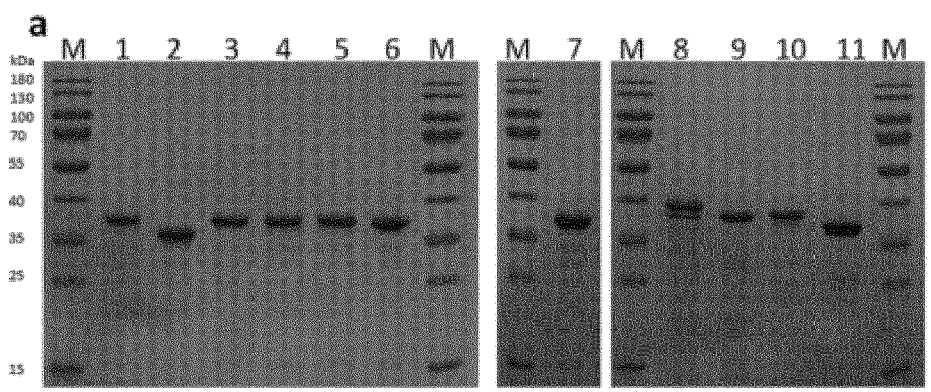
Figure 6:
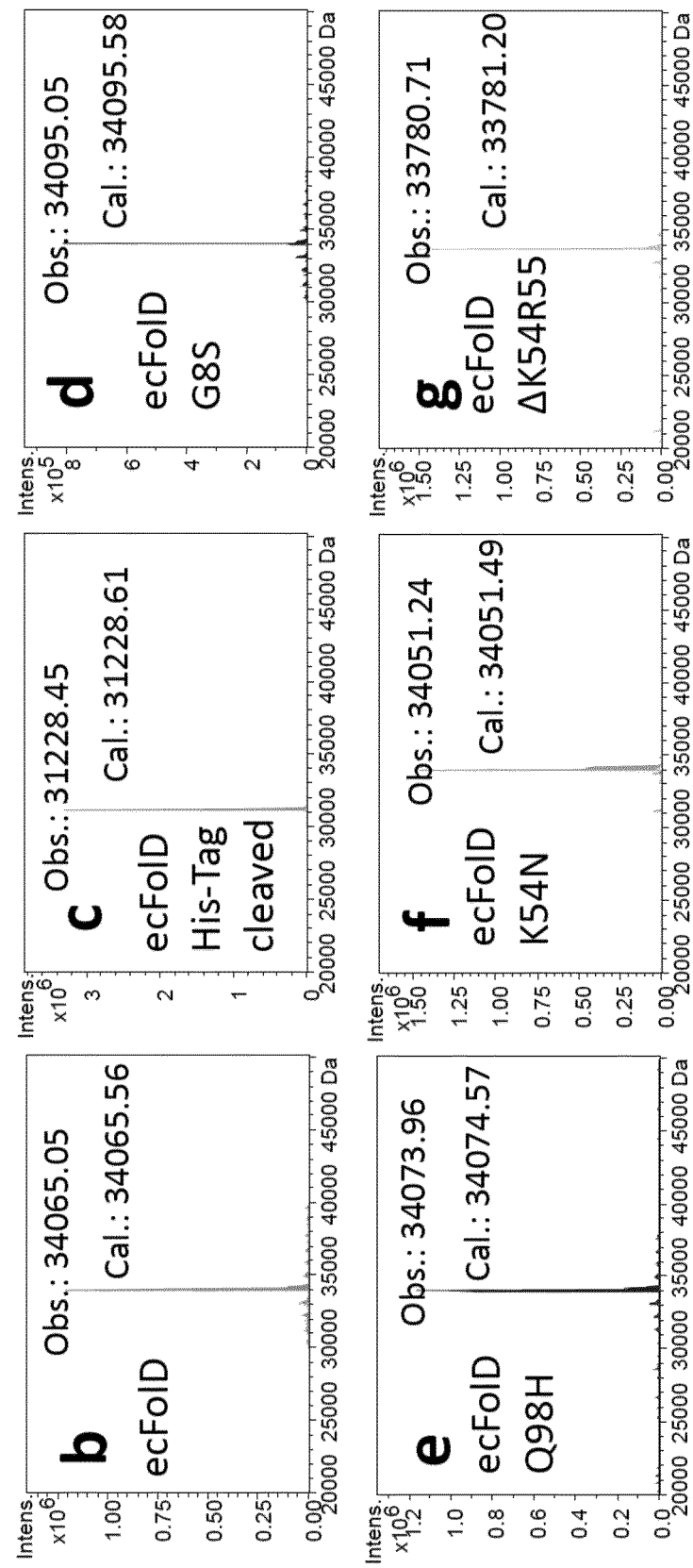
Figure 6:
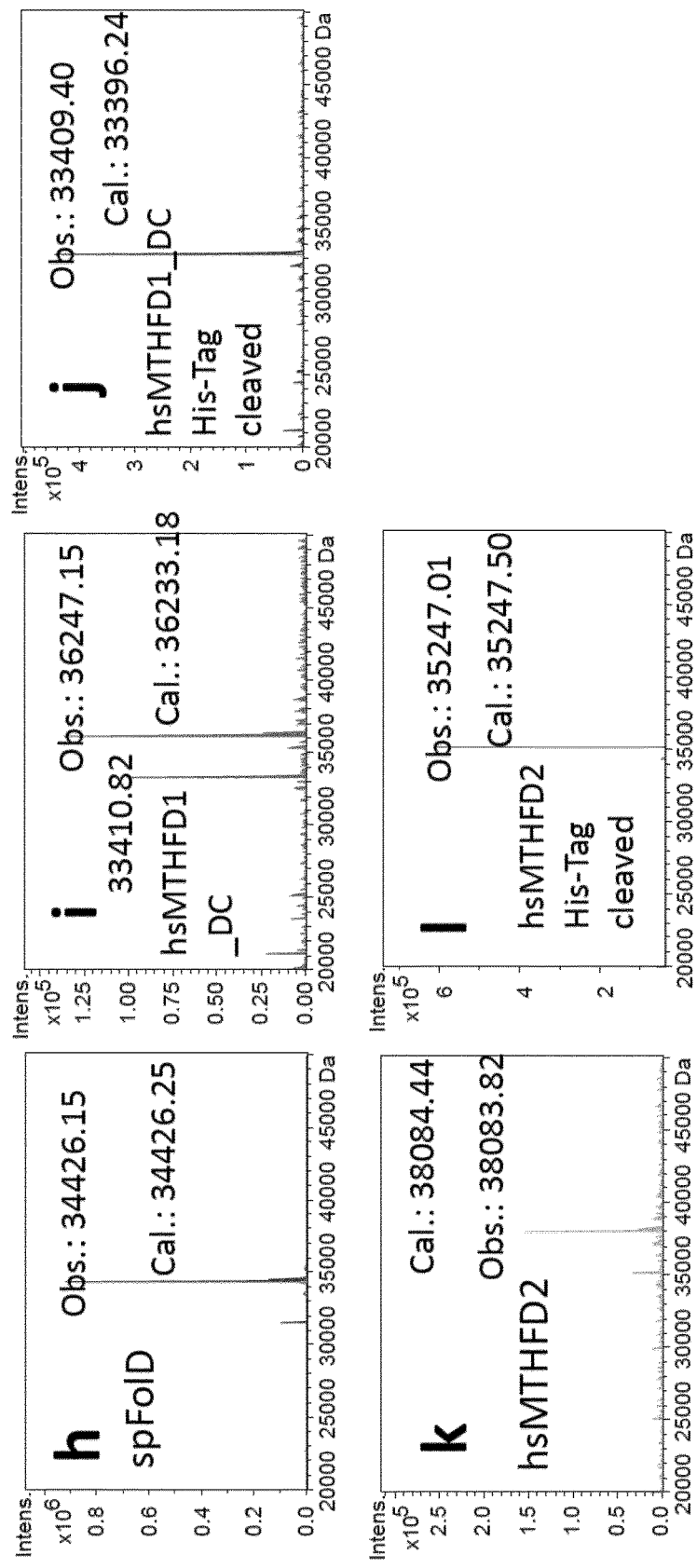

FIG. 6: Verification of purified by SDS-PAGE and LC-MS.

Figure 7:
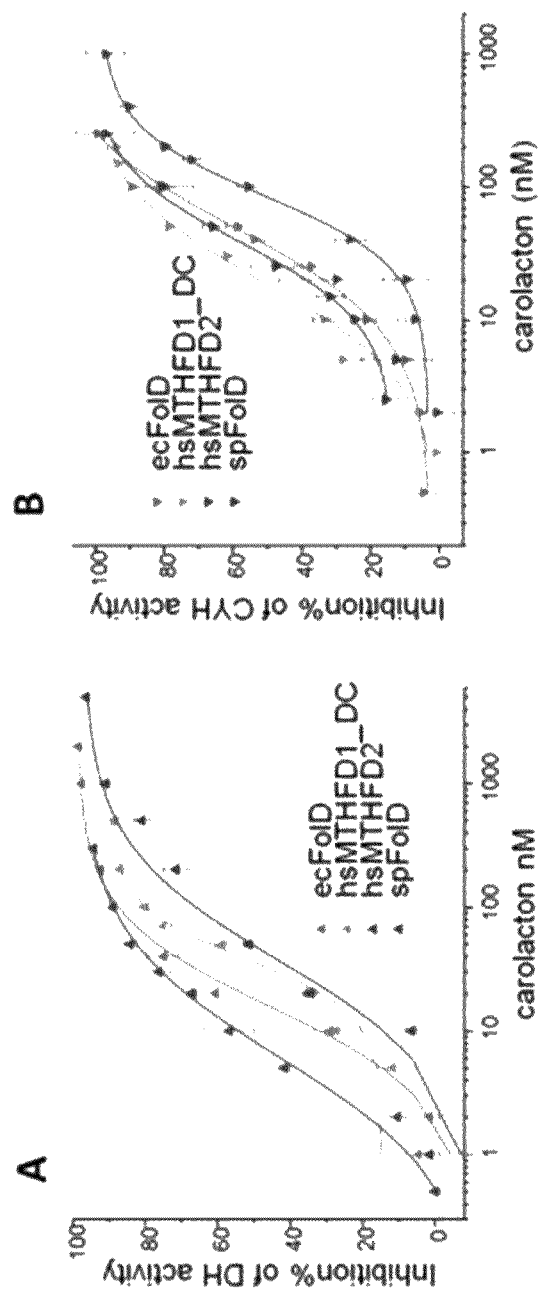

FIG. 7: Determination of IC50 for carolacton inhibition against wt FoID.

Figure 8:
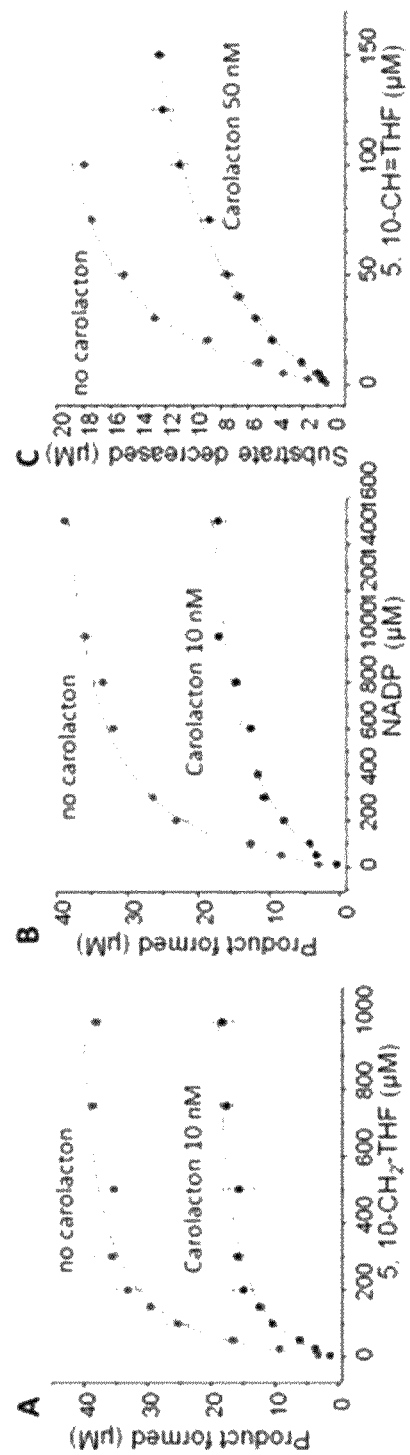

FIG. 8: Enzyme kinetics measurement of ecFoID.

Figure 9:
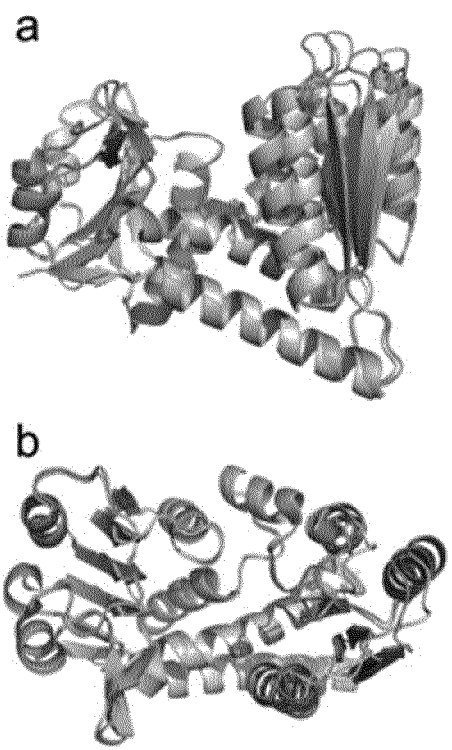

FIG. 9: Superposition of crystallized E.coli FoID.

Figure 10:
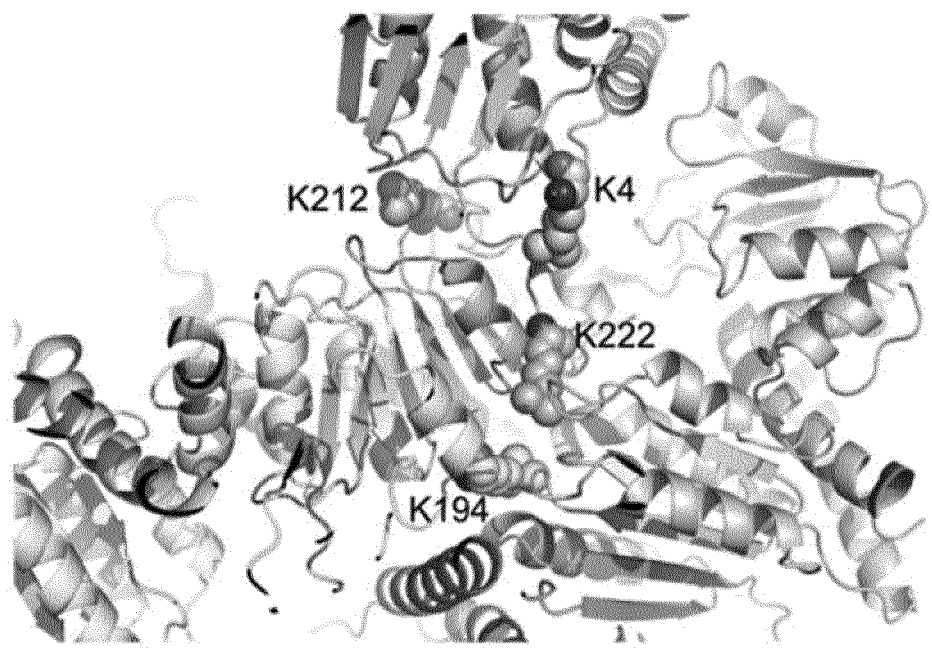

FIG. 10: Lysine methylation is essential for the ecFoID crystal structures reported herein.

Figure 11:
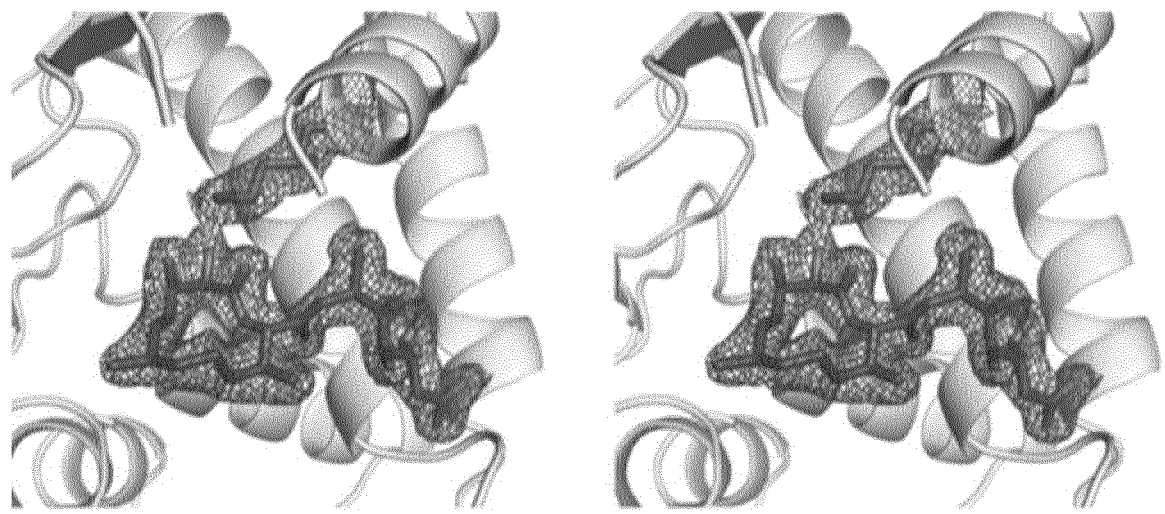

FIG. 11: Stereo view of the 2Fo-Fc electron density map for carolacton and K54.

Figure 12:
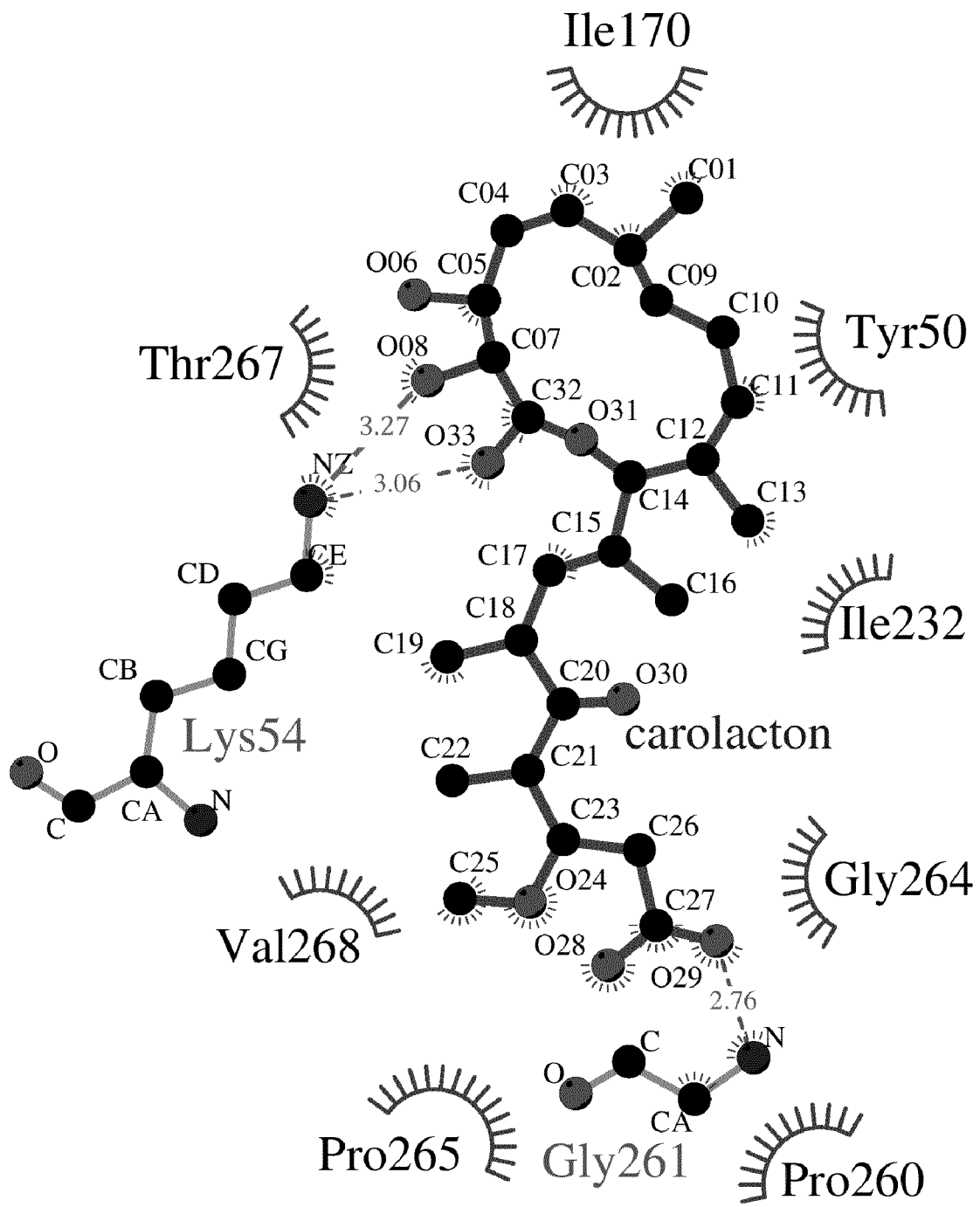

FIG. 12: Ligplot diagram showing the detailed interactions of carolacton with ecFoID.

Figure 13:
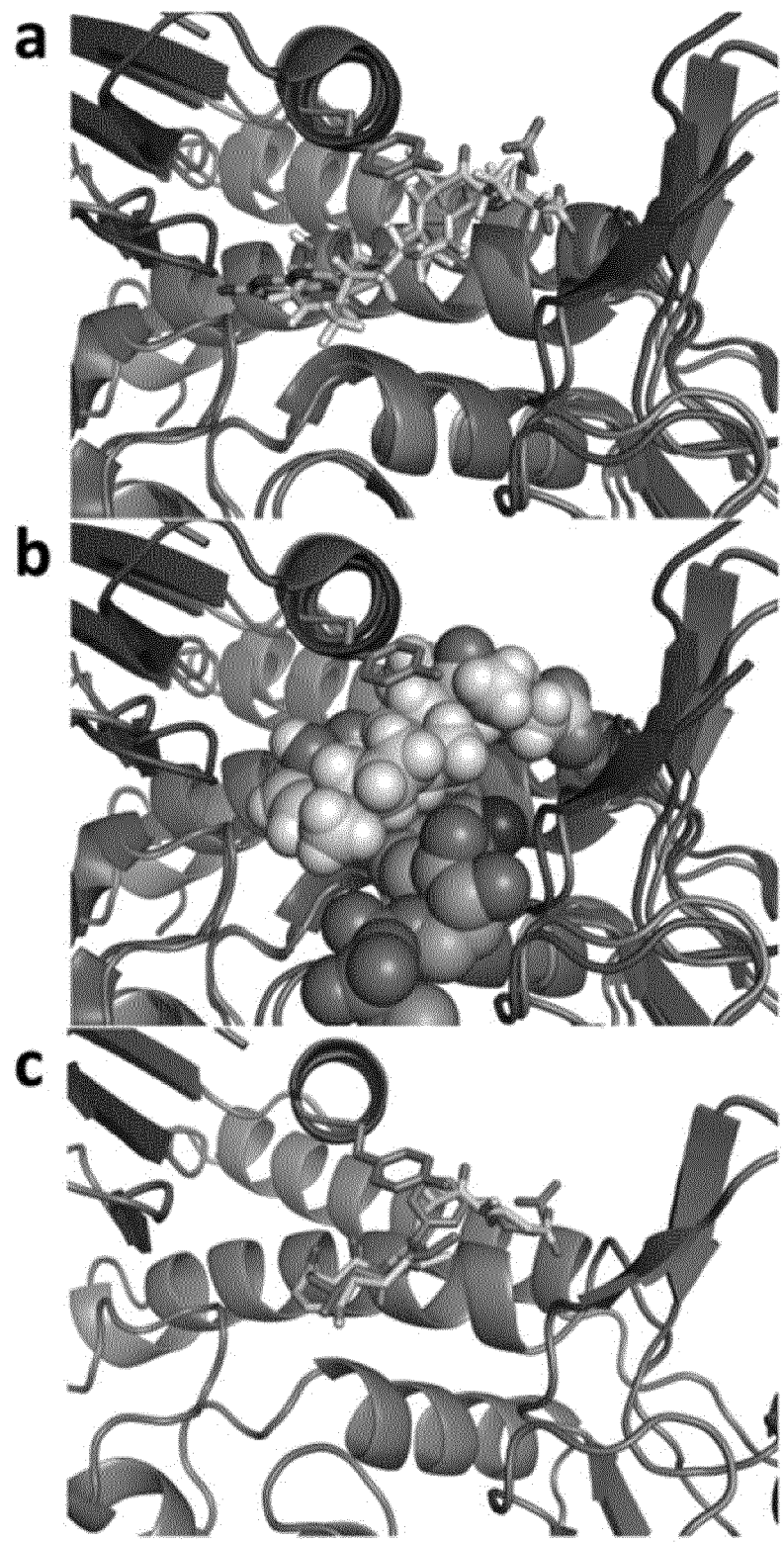

FIG. 13: Superposition of ecFoID (blue) with hsMTHFD2 (magenta).

Figure 14:
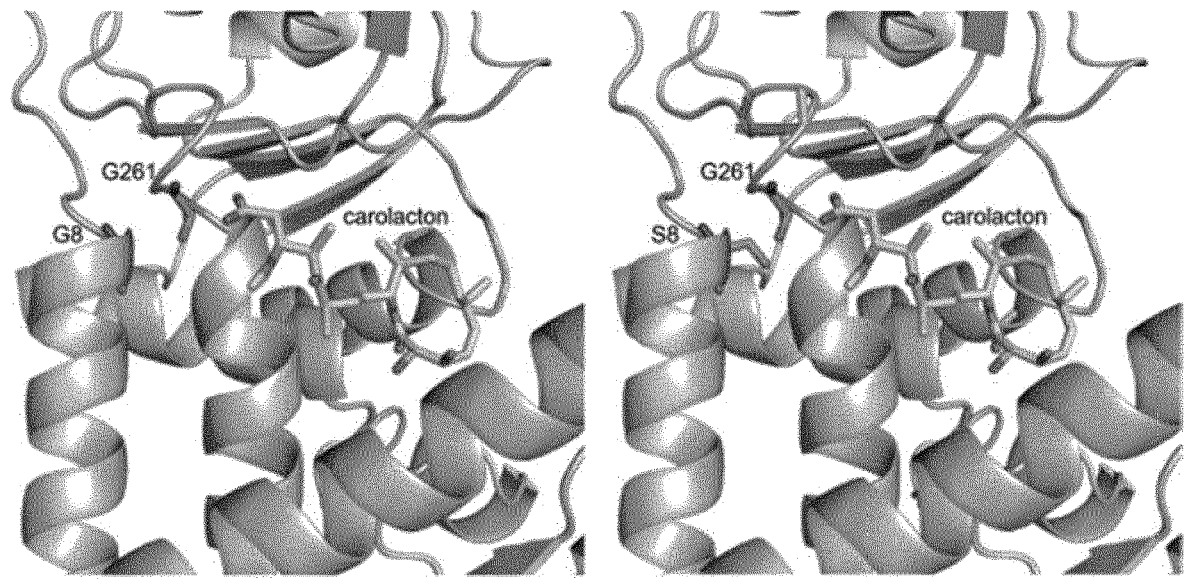

FIG. 14: Effect of mutation G8S on carolacton binding of ecFoID.

Figure 15:
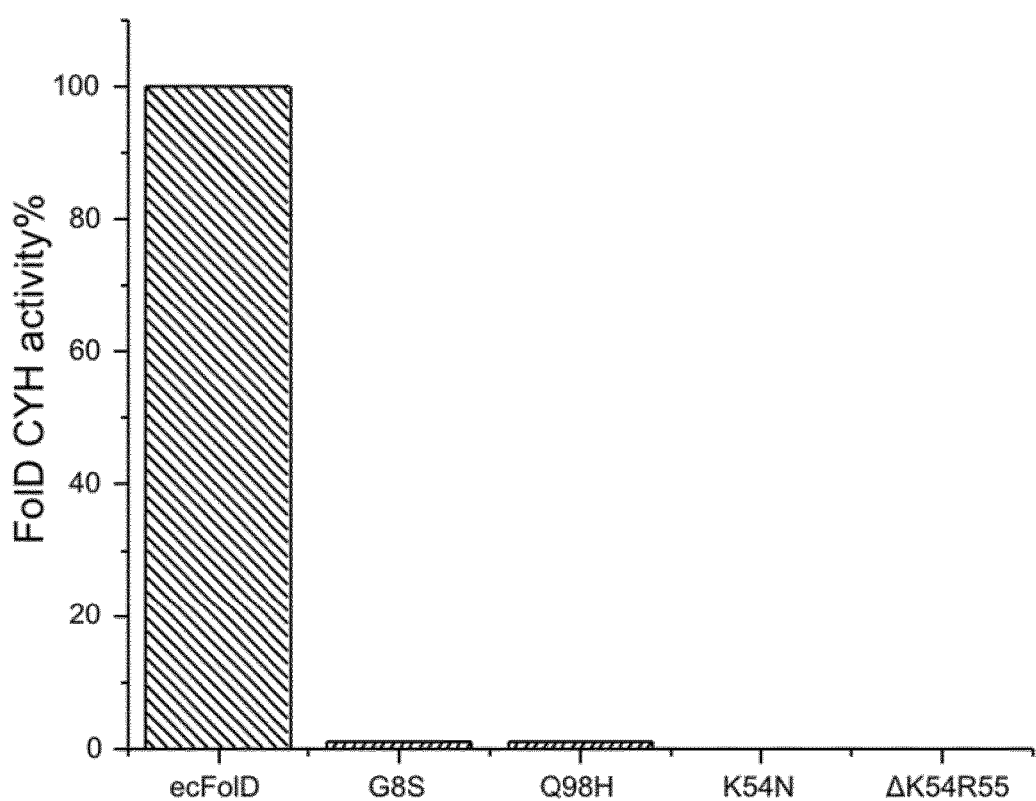

FIG. 15: Comparison of ecFoID CYH activity between wt and the carolacton-resistant mutants.

Figure 16:
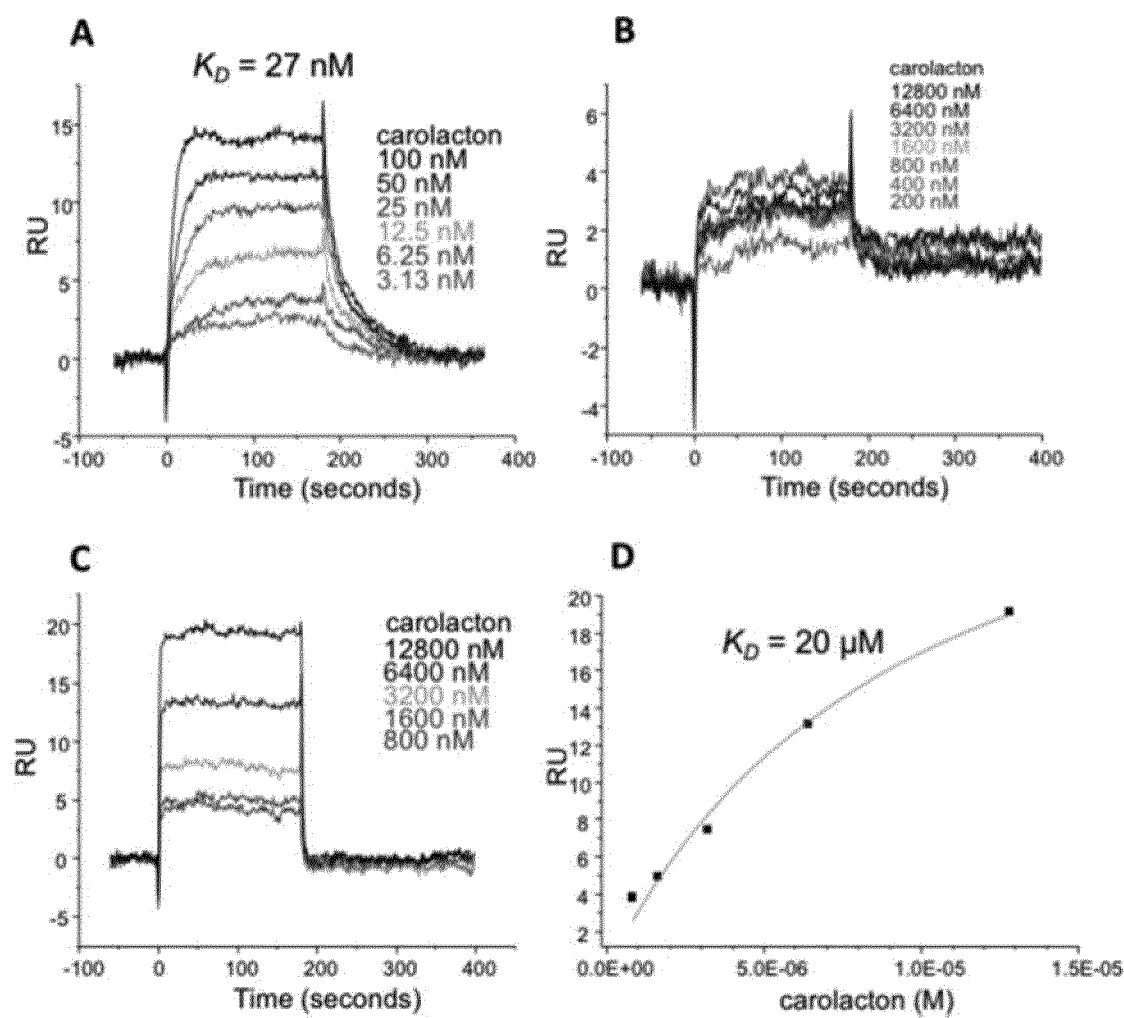

FIG. 16: SPR assay of ecFoID mutants.

Figure 17:
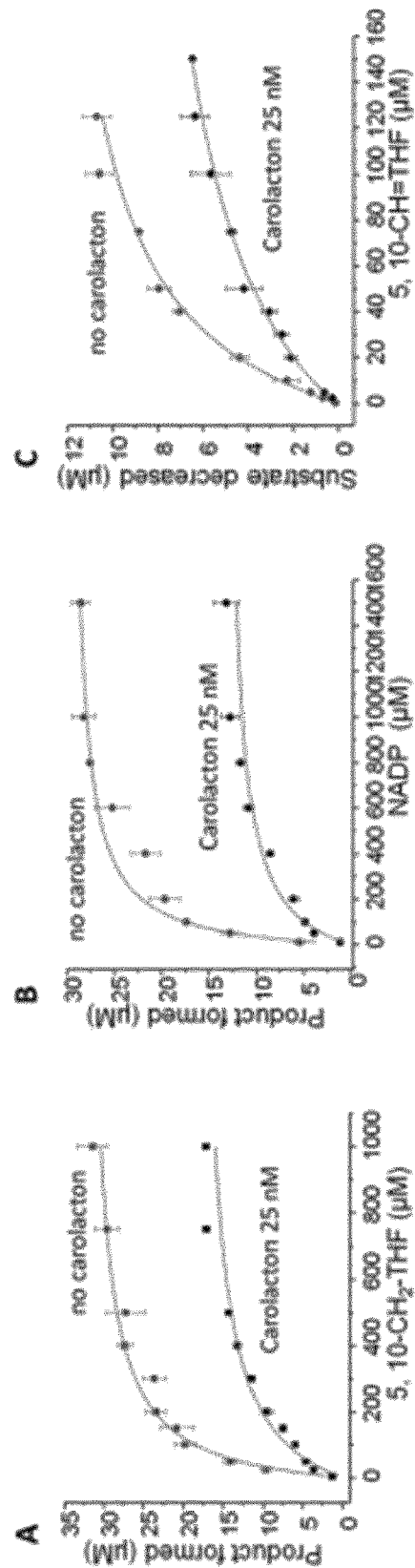

FIG. 17: Enzyme kinetics measurement of spFoID.

Figure 18:
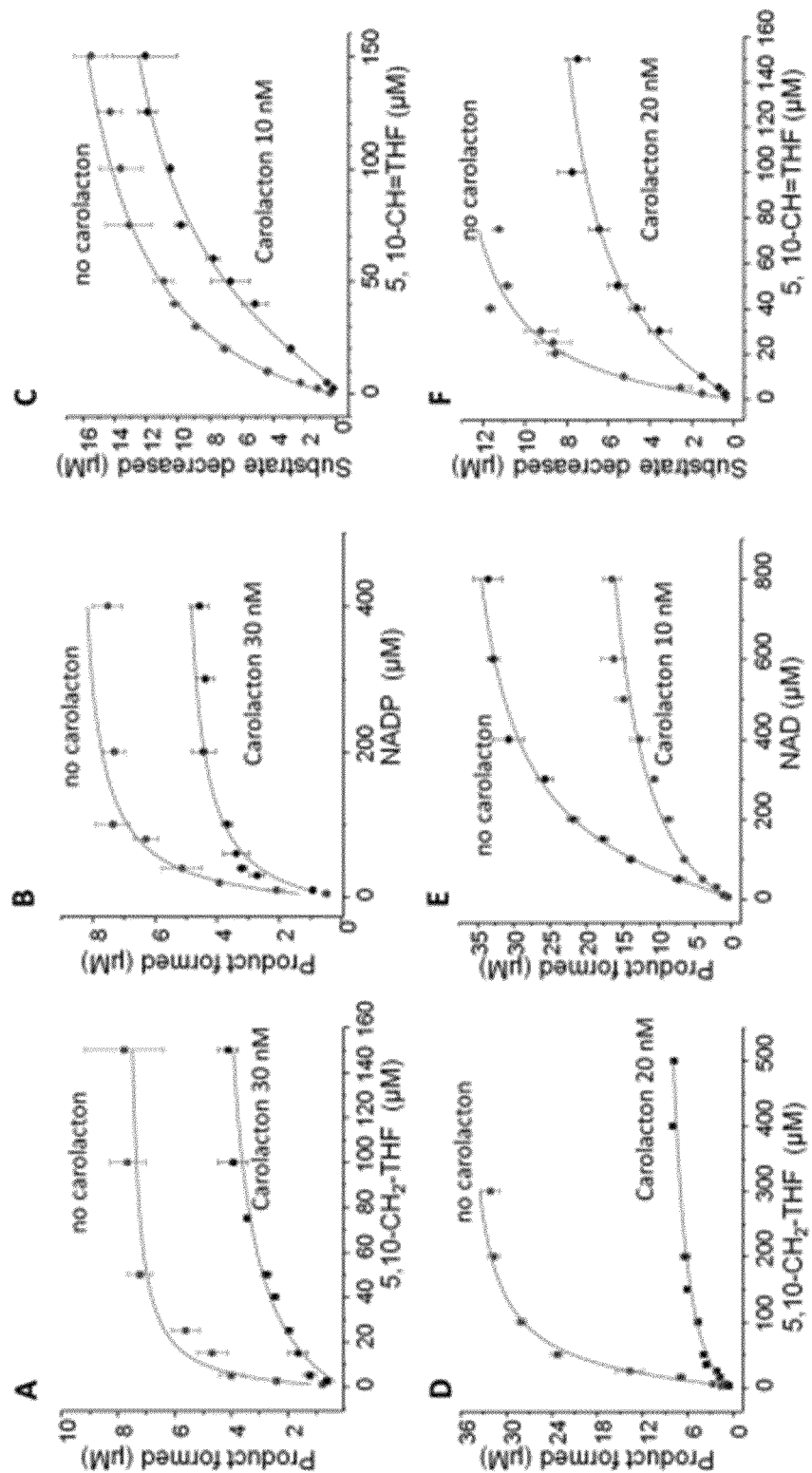

FIG. 18: The enzyme kinetics measurement of hsMTHFD1_DC and hsMTHFD2.

Figure 19:
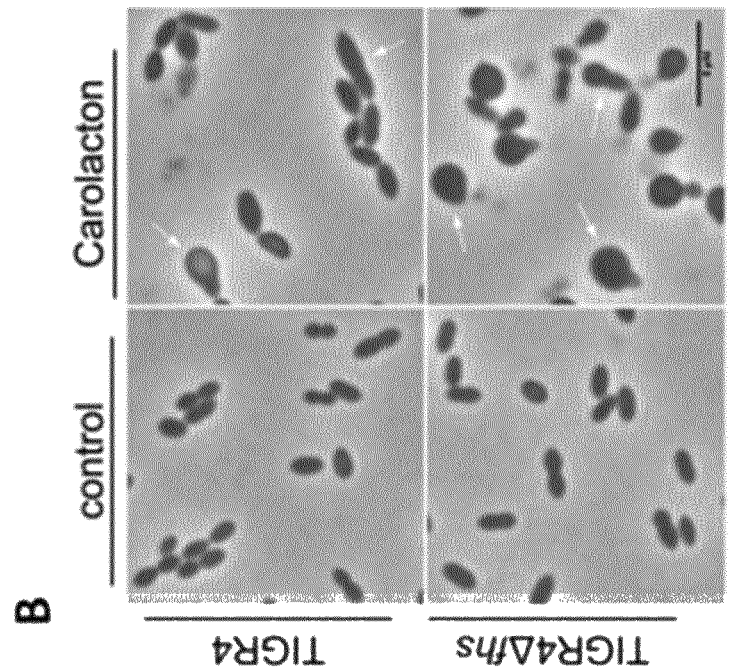
Figure 19:
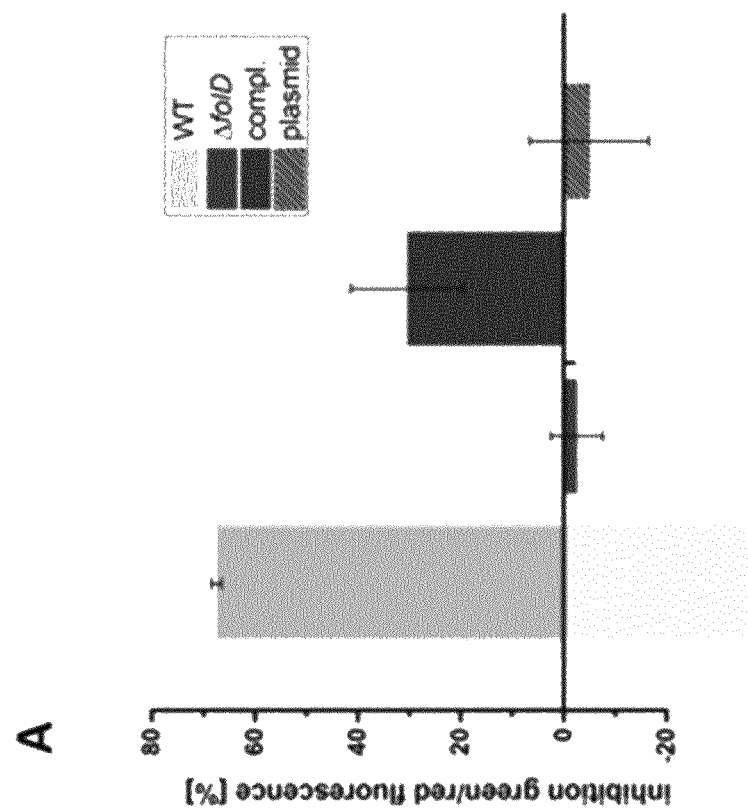

FIG. 19: Carolacton insensitivity of foID deletion mutants in S. mutans UA159 and S. pneumoniae TIGR4 and hypersensitivity to carolacton of S. pneumoniae TIGR4Δfhs.

Figure 20:
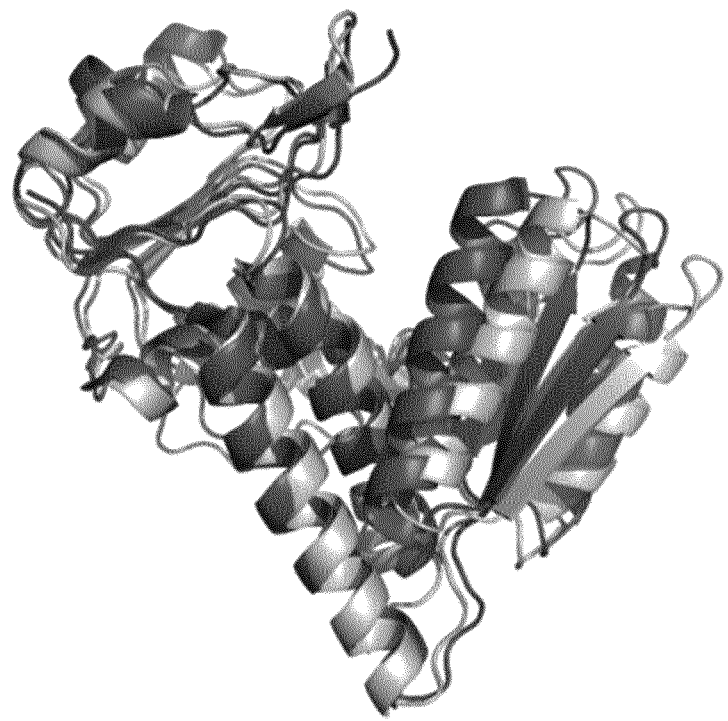

FIG. 20: Superposition of ecFoID (gray) with mitochondrial hsMTHFD2 (PDB ID 5tc4, magenta).

Figure 21:
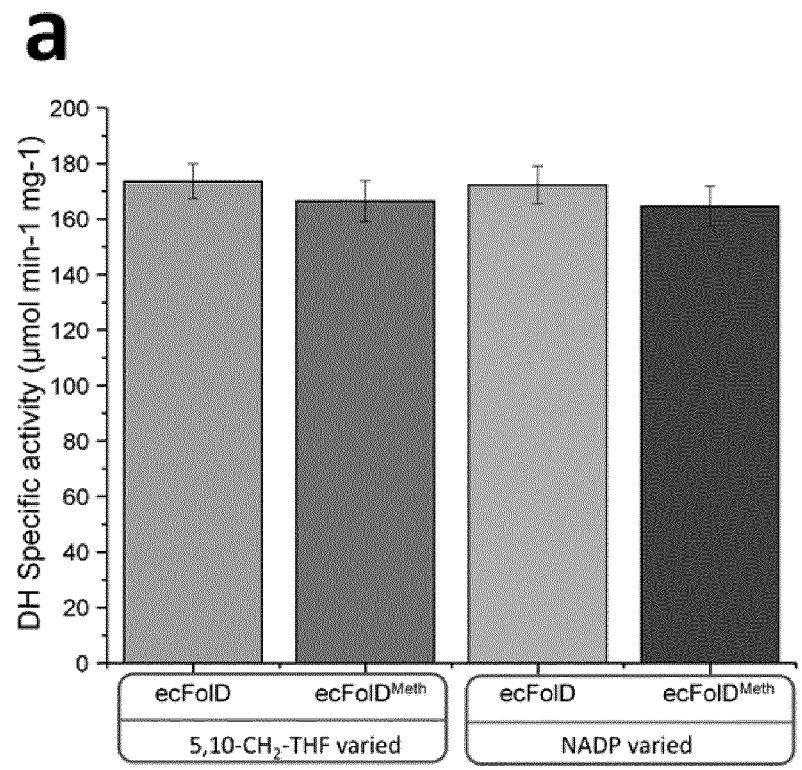
Figure 21:
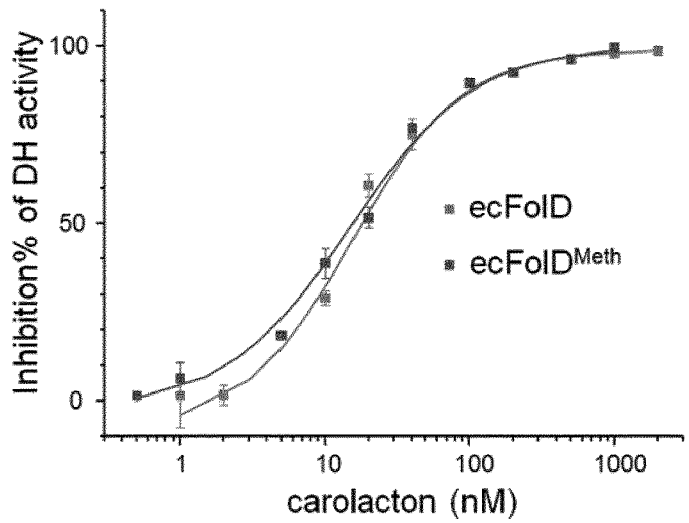

FIG. 21. Comparison between ecFoID and ecFoID$^{meth}$

Figure 22:
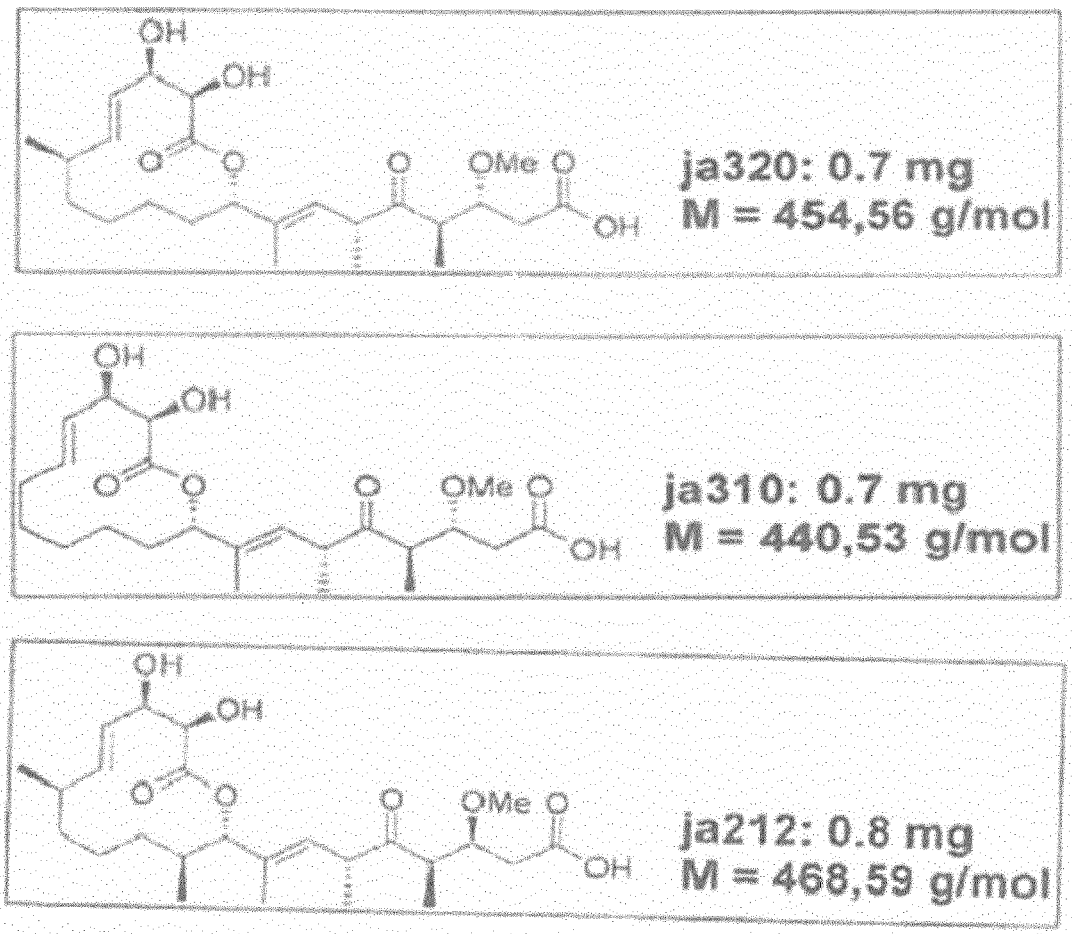

FIG. 22: Structures of synthetic derivatives of Carolacton

Figure 23:
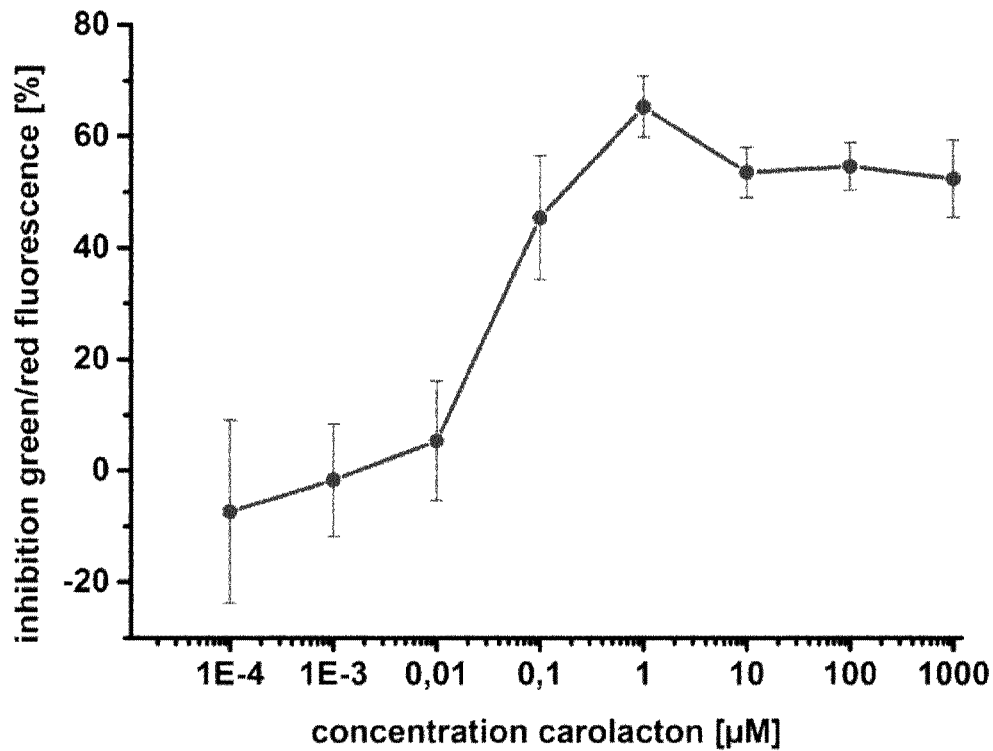
Figure 23:
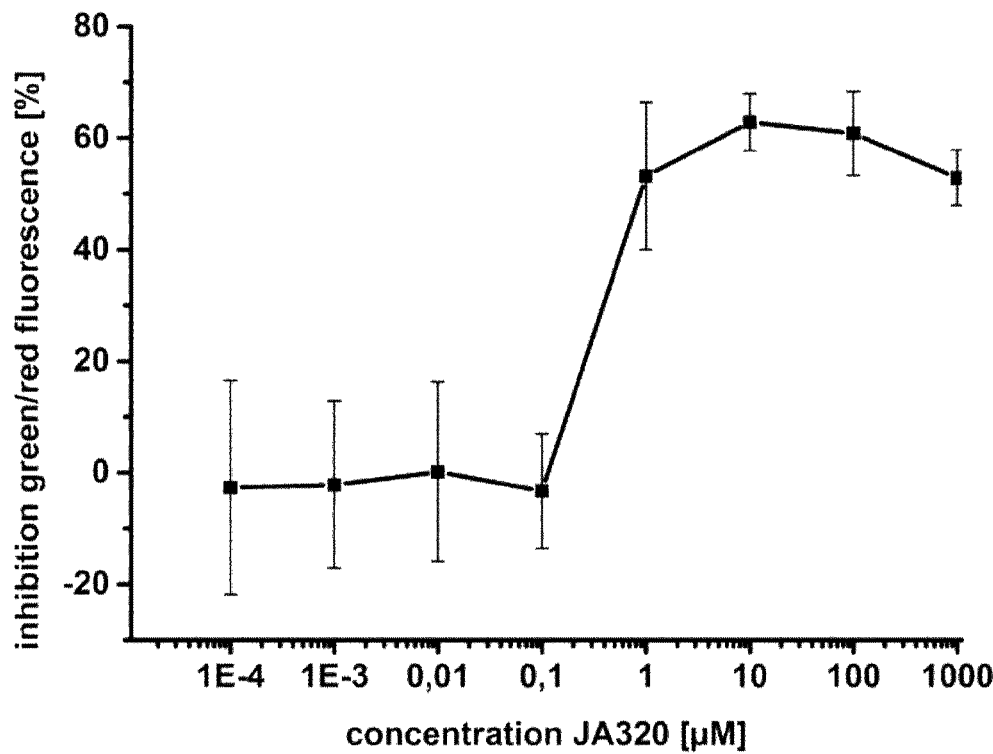

FIG. 23: Inhibition of S. mutans biofilm viability by Carolacton (left) and the derivative FIG. 24: Inhibition of planktonic growth of E. coli ToIC by synthetic Carolacton derivatives.

Figure 25:
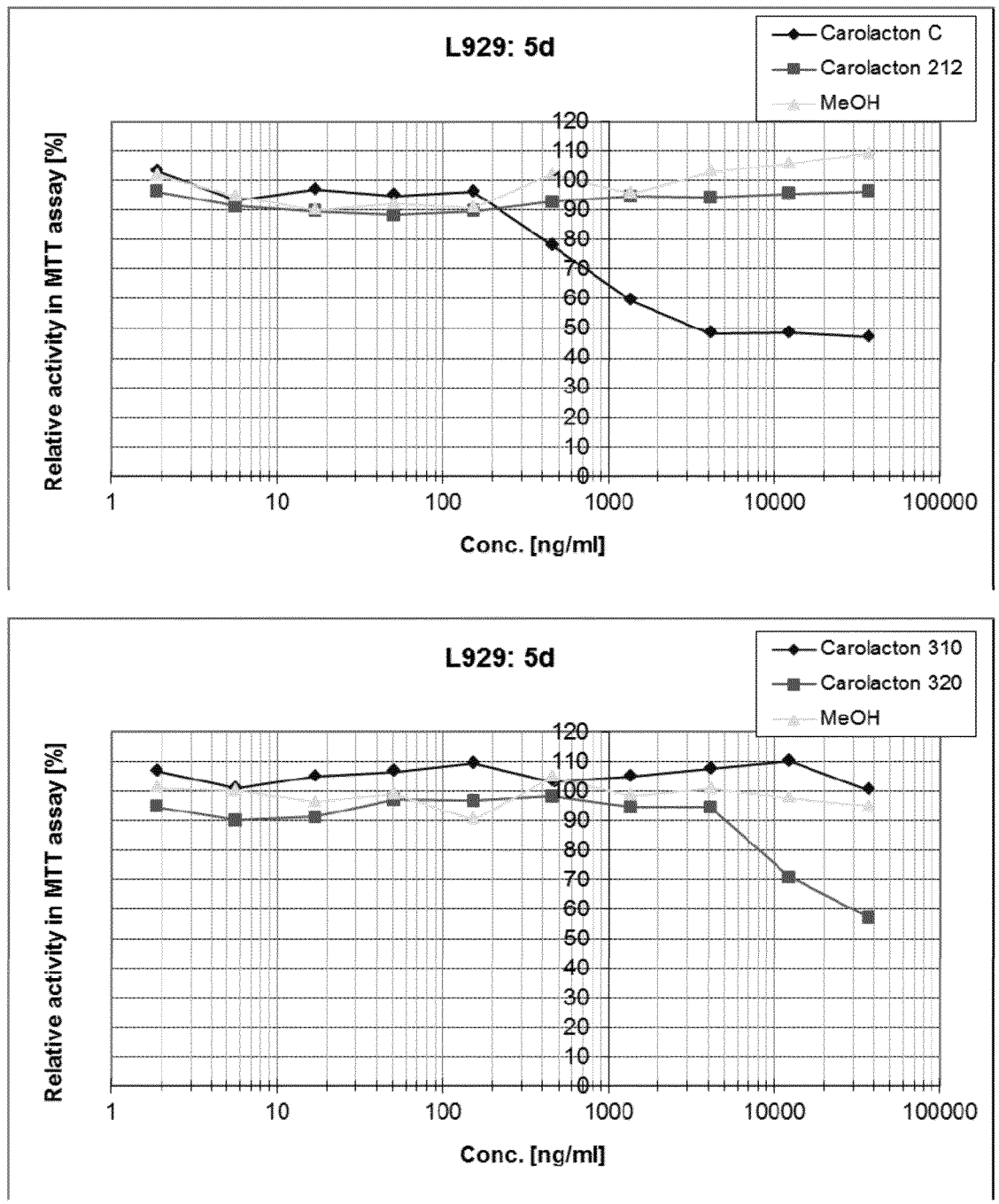

FIG. 25: Inhibition of mouse fibroblast proliferation by Carolacton and the synthetic derivatives Ja212, Ja310 and Ja320.

Detailed description of the figures:

FIG. 1. Enzymatic routes to synthesize 10-CHO-THF in different organisms and the chemical structure of the FoID inhibitor carolacton.

FIG. 2. Carolacton is a potent and tightly binding inhibitor of FoID. (A) SPR analysis of carolacton binding to ecFoID, RU means resonance units; (B) IC$_{50}$ determination for carolacton against DH and CYH activity of ecFoID; (C) Top view of the FoID-carolacton complex structure. Cartoon representations of apo-FoID (gold) and FoID in complex with carolacton (blue, lime) are superposed to show the movement and partial dissolution of helix α2. Residues involved in carolacton binding are shown as sticks. (D) Surface representation of FoID bound to carolacton, side-view. Colors correspond to (C). Partial dissolution of helix α2 as a result of the interaction of Y50, which forms a lid on carolacton that is further stabilized by R234, can be seen.

FIG. 3. The inhibition of carolacton to FoID dehydrogenase activity is either attenuated or abolished upon mutations which cause the attenuation of DH activity. (A) The residue DH activity of ecFoID mutants comparing with wt ecFoID DH activity; (B) IC$_{50}$ determination for carolacton against DH activity of ecFoID and mutants; (C) Position of Y50 in ecFoIDQ98H (gold). The position of Q98 in the apo (gray) and complex (blue) structures prevents the side-chain of Y50 from rotating out of position. (D) Position of Y50 in the apo (gray), complex (blue) and Q98H (gold) structures. The 90° rotation in Q98H prevents Y50 from forming the hydrophobic lid on carolacton (lime sticks).

FIG. 4. Carolacton effects on S. pneumoniae TIGR4 and foID deletion, complementation and fhs deletion mutants. (A) Growth inhibition of planktonic cultures of S. pneumoniae TIGR4 wild type, ΔfoID deletion mutant and controls in THBY. Carolacton (caro) (0.25 µg/ml) was added at an optical density of 600 nm (OD$_{600}$) of 0.15. (B) Planktonic growth of the S. pneumoniae TIGR4 wild type and the TIGR4Δfhs mutant in THBY. Cultures were treated with 0.25 µg/ml carolacton (OD$_{600}$ 0.15).

FIG. 5. Carolacton effects on hsMTHFD2. (A) SPR analysis of carolacton binding to hsMTHFD2. (B) IC$_{50}$ determination for carolacton against DH and CYH activity of hsMTHFD2.

FIG. 6. All purified FoID proteins checked by SDS-PAGE and LC-MS. (A) The SDS-PAGE gel of all purified FoID. M: PageRuler prestained protein ladder; 1: His-Tag fusion FoID of E. coli ToIC; 2: FoID of E. coli ToIC (His-tag cleaved off) 3: His-Tag fusion FoID of E. coli ToIC G8S; 4: His-Tag fusion FoID of E. coli ToIC Q98H; 5: His-Tag fusion FoID of E. coli ToIC K54N; 6: His-Tag fusion FoID of E. coli ToIC ΔK54R55; 7: His-Tag fusion FoID of S. pneumoniae TIGR4; 8: His-Tag fusion hsMTHFD1_DC; 9: His-Tag cleaved hsMTHFD1_DC; 10: His-Tag fusion hsMTHFD2; 11: His-Tag cleaved hsMTHFD2. (B-L) Deconvoluted mass spectra of all FoID proteins. Cal. stands for calculated average neutral mass according to the protein sequence; Obs. indicates the average neutral mass observed by LC-MS measurement. The mass of hsMTHFD1_DC is 14 Da heavier than its calculated mass which is possibly by a methylation on one residue.

FIG. 7. The determination of IC$_{50}$ for carolacton inhibition against all wt FoID described herein. (A) IC$_{50}$ determination for carolacton against dehydrogenase activity of FoID from different organisms. (B) IC$_{50}$ determination for carolacton against cyclohydrolase activity of FoID from different organisms.

FIG. 8. The enzyme kinetics measurement of ecFoID. (A) The determination of 5,10-CH$_2$-THF K$_M$ in the presence of 1 mM NADP and 5,10-CH$_2$-THF apparent K$_M$ in the presence of 1 mM NADP and 10 nM carolacton. (B) The determination of NADP K$_M$ in the presence of 1 mM 5,10-CH$_2$-THF and NADP apparent K$_M$ in the presence of 1 mM 5,10-CH$_2$-THF and 10 nM carolacton. (C) The determination of 5,10-CH=THF K$_M$ and the determination of 5,10-CH=THF apparent K$_M$ in the presence of 50 nM carolacton.

FIG. 9. Superposition of E.coli FoID crystallized in this study (gray) with the published structure (PDB ID 1B0A, cyan). A Side view. B Structures rotated by 90° around the horizontal axis towards the viewer.

FIG. 10. Lysine methylation is essential for the ecFoID crystal structures described herein. ecFoID protomers are shown as cartoon representations in individual colours. Dimethylated lysine residues are shown as spheres with their colour corresponding to the protomer they belong to.

FIG. 11. Stereo view of the 2Fo-Fc electron density map for carolacton and K54. ecFoID is shown as a yellow cartoon, carolacton and K54 as sticks and the electron density as a blue isomesh.

FIG. 12. Ligplot diagram showing the detailed interactions of carolacton with ecFoID.

FIG. 13. Superposition of ecFoID (blue) with hsMTHFD2 (magenta). (a) Carolacton (lime) clashes with the bound substrate analog L345899 (cyan). (b) carolacton clashes with co-factor NAD+(green). (c) New carolacton analog "carylacton" can engage with Y50 but has a tail which is too long to hydrogen-bond with G261.

FIG. 14. Effect of mutation G8S on carolacton binding of ecFoID. Left: In wt ecFoID (gray) G8 is hydrogen-bonded to G261 (both orange), which in turn forms hydrogen bonds with carolacton (lime). Right: In the mutant G8S, the side-chain of the serine clashes with G261 in all conformations. Therefore, the loop containing G261 needs to move to accommodate S8, which results in a clash with carolacton.

FIG. 15. Comparison of ecFoID CYH activity between wt and the carolacton-resistant mutants.

FIG. 16. The SPR assay of ecFoID mutants. (A) SPR analysis shows carolacton has no binding to ecFoID K54N. (B) SPR analysis shows carolacton has weak binding to ecFoID Q98H, but the $K_D$ value cannot be determined uniquely by SPR kinetics calculation. (C) The affinity calculation based on SPR analysis of carolacton binding to ecFoID Q98H gives a $K_D$ value which is 20 µM.

FIG. 17. The enzyme kinetics measurement of spFoID. (A) The determination of 5,10-CH$_2$-THF $K_M$ in the presence of 1 mM NADP and 5,10-CH$_2$-THF apparent $K_M$ in the presence of 1 mM NADP and 25 nM carolacton. (B) The determination of NADP $K_M$ in the presence of 1 mM 5,10-CH$_2$-THF and NADP apparent $K_M$ in the presence of 1 mM 5,10-CH$_2$-THF and 25 nM carolacton. (C) The determination of 5,10-CH=THF $K_M$ and the determination of 5,10-CH=THF apparent $K_M$ in the presence of 25 nM carolacton.

FIG. 18. The enzyme kinetics measurement of hsMTHFD1_DC and hsMTHFD2. (A) The determination of 5,10-CH$_2$-THF $K_M$ for hsMTHFD1_DC in the presence of 0.4 mM NADP and 5,10-CH$_2$-THF apparent $K_M$ for hsMTHFD1_DC in the presence of 0.4 mM NADP and 30 nM carolacton. (B) The determination of NADP $K_M$ for hsMTHFD1_DC in the presence of 0.4 mM 5,10-CH$_2$-THF and NADP apparent $K_M$ for hsMTHFD1_DC in the presence of 0.4 mM 5,10-CH$_2$-THF and 25 nM carolacton. (C) The determination of 5,10-CH=THF $K_M$ for hsMTHFD1_DC and the determination of 5,10-CH=THF apparent $K_M$ for hsMTHFD1_DC in the presence of 25 nM carolacton. (D) The determination of 5,10-CH$_2$-THF $K_M$ for hsMTHFD2 in the presence of 0.6 mM NADP and 5,10-CH$_2$-THF apparent $K_M$ for hsMTHFD2 in the presence of 0.6 mM NADP and 20 nM carolacton. (E) The determination of NADP $K_M$ for hsMTHFD2 in the presence of 0.6 mM 5,10-CH$_2$-THF and NADP apparent $K_M$ for hsMTHFD2 in the presence of 0.6 mM 5,10-CH$_2$-THF and 10 nM carolacton. (F) The determination of 5,10-CH=THF $K_M$ for hsMTHFD2 and the determination of 5,10-CH=THF apparent $K_M$ for hsMTHFD2 in the presence of 20 nM carolacton.

FIG. 19. Carolacton insensitivity of foID deletion mutants in S. mutans UA159 and S. pneumoniae TIGR4 and hypersensitivity to carolacton of S. pneumoniae TIGR4Δfhs. (A) Inhibition of S. mutans biofilm viability of the UA159 wild type, the ΔfoID mutant and controls in the presence of 2.5 µg/ml carolacton, as determined by LIVE/DEAD viability staining. (B) Phase-contrast microscopy of the S. pneumoniae TIGR4 wild type and the TIGR4Δfhs strain. Individual carolacton-treated cells of the TIGR4 wild type exhibited aberrant cell morphologies (elongation and swelling; white arrows). Deletion of fhs strongly increased the number of cells with carolacton-related abnormal cell morphologies. All results show the average of three independent biological replicates including their standard deviation. Scale bar: 5 µm.

FIG. 20. Superposition of ecFoID (gray) with mitochondrial hsMTHFD2 (PDB ID 5tc4, magenta).

FIG. 21. The comparison between ecFoID and ecFoID$^{meth}$ (The lysine methylation processed ecFoID). (a) The column plot for the comparison of DH activity of ecFoID and ecFoID$^{Meth}$, the specific activity calculated based on varied 5,10-CH$_2$-THF and NADP$^+$ both showed. Data are presented as means ±s.e.m of 3 independent replicates. DH specific activity values were calculated based on the $V_{max}$ values obtained via Michaelis-Menten fitting. The one-way ANOVA test was used for statistical analysis, P<0.01. (b) The determination of IC$_{50}$ for carolacton inhibition against ecFoID and ecFoID$^{Meth}$. Data are presented as means ±s.e.m of 3 independent replicates. IC$_{50}$ values were obtained via logistic dose-response fitting. The one-way ANOVA test was used for statistical analysis, P<0.01.

FIG. 22. Depiction of structures of four synthetic derivatives of Carolacton.

FIG. 23. Inhibition of S. mutans biofilm viability by Carolacton (left) and the derivative Ja320. (right).

Figure 24:
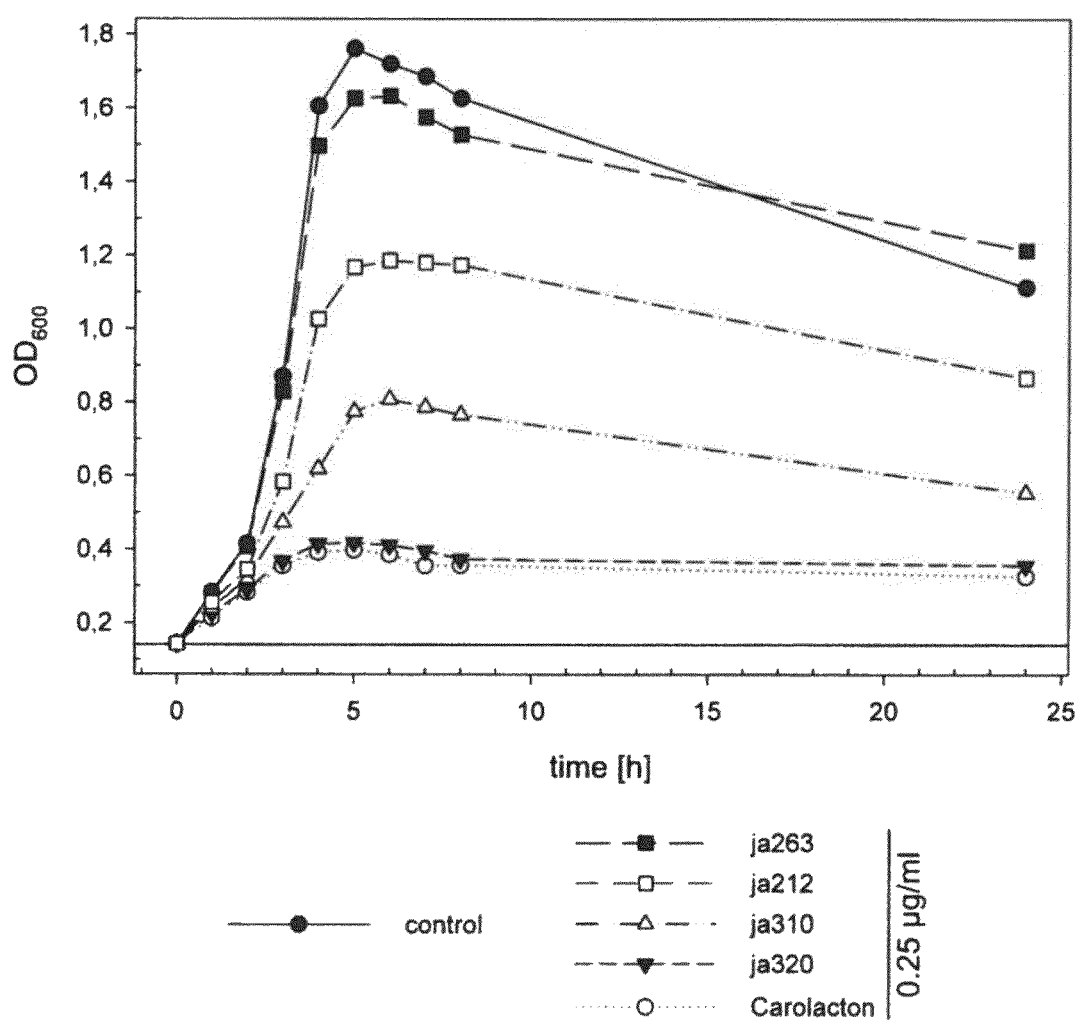

FIG. 24. Inhibition of planktonic growth of Streptococcus pneumoniae TIGR4 by synthetic Carolacton derivatives.

FIG. 25. Inhibition of mouse fibroblast proliferation by Carolacton and the synthetic derivatives Ja212, Ja320 and Ja310.

EXAMPLES

The examples show that the molecular target of carolacton is the bifunctional enzyme 5,10-methylenyltetrahydrofolate cyclohydrolase/5,10-methylene tetrahydrofolate dehydrogenase, which is abbreviated to FoID in bacteria, MTHFD in humans, and DHCH in protozoan parasites. The examples more show that the administration of carolacton allows for inhibition of unwanted cell proliferation of a pathological eukaryotic cell, in particular for the treatment of cancer.

Materials and Methods used in the Examples:

Strains, Plasmids and Medium

The Streptococcus mutans and Streptococcus pneumoniae strains used herein are UA159 and TIGR4, respectively. S. pneumoniae TIGR4 was routinely grown on Columbia blood agar plates (BD Biosciences) as described previously (Donner et. al, 2016). Streptococci were grown in Todd-Hewitt-Broth +1% (w/v) yeast extract (THBY, BD Biosciences)) at 37° C. and 5% CO$_2$. The E. coli ToIC strain used in carolacton-resistant mutant development is an antibiotic-sensitive E. coli strain without its outer membrane channel protein ToIC. E. coli DH1OB or DH5α strain was used for gene cloning and E. coli BL21 (DE3) was used for protein expression. The protein expression plasmid pHis-TEV (Liu et al., 2009) was used for cloning and expression of all different foID gene orthologues studied herein.

Carolacton-resistant Mutant Development

First, the minimum inhibition concentration (MIC) of carolacton on *E. coli* ToIC strain has been determined. We started to develop the resistant mutants on CASO agar plates supplemented with 4× the MIC concentration of carolacton as selection pressure. Different numbers of *E. coli* ToIC cells from $1\times10^7$ to $10^9$ were spread on caso agar plate with carolacton, respectively. After 7 days, *E. coli* ToIC colonies, which were resistant to carolacton, started to form on the agar plates. The mutants picked were inoculated in liquid MHB medium supplemented with carolacton. The genomic DNA of WT *E. coli* ToIC and carolacton resistant mutants were extracted and sent for genome sequencing.

Gene Cloning, Protein Expression and Purification

All foID gene orthologues described herein were cloned into the pHis-TEV protein expression vector. The foID genes of *E. coli* ToIC and its carolacton-resistant mutants were amplified from the genomic DNA of the corresponding strains. The foID gene of *S. pneumoniae* was amplified from the genomic DNA of the TIGR4 strain. The cDNA encoding MTHFD1 and MTHFD2 was synthesized based on human genomic DNA deposited (gene ID 4522 and 10197, respectively). All primers and restriction sites are listed in Tables S6. The resulting protein expression plasmids were verified by enzyme restriction digestion and DNA sequencing before being transformed into *E. coli* BL21 (DE3) for protein overexpression and purification. For optimal protein purification, a systematic buffer test including ten different buffers was conducted for each protein by using the King Fisher mL (ThermoFisher scientific) magnetic beads purification system. For large-scale protein purification, a single colony was picked into LB liquid medium containing 50 µg/ml kanamycin to make an overnight culture. The overnight culture was inoculated 1 to 100 into fresh LB medium supplemented with 50 µg/ml kanamycin and was grown at 37° C. until $OD_{600}$ reached 0.6. Then, the culture was transferred to 16° C. for half an hour to cool the culture before 0.1 mM IPTG was added to induce protein expression. The cells were harvested and lysed by sonication after 16 h shaking. The proteins were purified by immobilized metal ion affinity chromatography (IMAC) on a 5 mL Histrap HP column (GE healthcare). The HiPrep 26/10 desalting column (GE healthcare) was used to remove imidazole. When removal of the N-terminal 6× His-tag was required, TEV protease was added to the imidazole free protein solution to incubate at 4° C. overnight and followed by another hour at room temperature. The digestion mixture was loaded on a HisTrap HP column for the second time to bind the undigested protein, His-tag and TEV protease. The flow-through, which contains the protein was collected, concentrated and loaded onto a gel filtration column HiLoad 16/600 Superdex 200 pg (GE healthcare) to further remove impurities. Finally, all purified proteins used were checked by sodium dodecyl sulfate polyacrylamide gel electrophoresis (SDS-PAGE) and subjected to liquid chromatography-mass spectrometry (LC-MS) to check purity and assess protein molecular weights.

Enzyme Assay Conditions (6R,S)-5,10-Methylene-5,6,7,8-tetrahydrofolic acid ((6R,S)-5,10-$CH_2$-THF), calcium salt and (6R,S)-5,10-Methenyl-5,6,7,8-tetrahydrofolic acid ((6R,S)-5,10-CH=THF) chloride were purchased from Schircks Laboratories (Bauma, Switzerland) and were used as substrates for FoID dehydrogenase and cyclohydrolase enzyme assays, respectively. Only the R-isomer, which accounts for 50% of (6R,S)-5,10-$CH_2$-THF and (6R,S)-5,10-CH=THF, respectively, is used by the enzyme. (6R,S)-5,10-$CH_2$-THF was dissolved in $N_2$-spargeled basic buffer (50 mM Tris-HCl (pH 8.0), 100 mM β-mercaptoethanol) as described by Sah and Varshney, 2015a (6R,S)-5,10-CH=THF was first dissolved in DMSO as a 100 mM stock solution.

Because FoID is a bifunctional enzyme, dehydrogenase and cyclohydrolase activities were determined for FoID enzyme kinetics, respectively. The dehydrogenase activity of FoID was assayed for its substrate 5,10-CH2-THF and cofactor NADP+ (in the case of MTHFD2, NAD+ was used as cofactor) based on monitoring the formation of 5,10-CH=THF while the cyclohydrolase activity of FoID was determined for its substrate 5,10-CH=THF by monitoring the hydrolysis of 5,10-CH2-THF. The enzyme kinetics for the dehydrogenase activity of all FoIDs except hsMTHFD1_DC were determined at 30° C. in 50 mM Tris-HCl (pH 7.5), 30 mM β-mercaptoethanol. The hsMTHFD1_DC dehydrogenase activity was measured in 25 mM MOPS (pH 7.3), 30 mM β-mercaptoethanol at 30° C. To measure the enzyme kinetics constants for 5,10-CH2-THF, for example in the case of ecFoID, the NADP concentration was fixed at 1 mM and the concentration of 5,10-CH2-THF varied from 5 µM to 1,500 µM (R-isomer). Similarly, to measure the kinetic constants of ecFoID for NADP+, the concentration of 5,10-CH2-THF (R-isomer) was fixed at 1 mM and the concentration of NADP+ varied from 10 µM to 1,500 µM. For different FoIDs, the varied concentration range of substrates could be different. The 50 µL reactions of dehydrogenase assays were initiated by adding appropriate amounts enzyme (4 nM ecFoID, 4 nM spFoID, 15 nM hsMTHFD1_DC, 20 nM hsMTHFD2, 20 nM G8S, 20 nM Q98H, 10 nM K54N, 200 nM ΔK54R55 in the corresponding assays) and terminated with 50 µL 1 M HCl after 2 min incubation at 30° C. To monitor the formation of 5,10-CH=THF, the absorbance of the reaction mixture was monitored at 350 nm in micro UV cuvettes (BRAND, Essex, Connecticut, USA). The concentration of 5,10-CH=THF produced in the reaction was determined using an extinction co-efficient of 0.0249 µM-1 cm-1. Cyclohydrolase activity for each FoID was assayed in the same buffer as dehydrogenase activity at 30° C. but for 30 s. The concentration of FoID used in each assay was 5 nM of ecFoID, spFoID and hsMTHFD1_DC, respectively, and 2 nM of hsMTHFD2. The consumption of 5,10-CH=THF was measured by recording the absorbance of the reactions at 355 nm using the TECAN Infinite 200 PRO equipped with a monochromator. To measure the enzyme kinetic constants, different concentrations of 5,10-CH=THF (varied from 0.5 pM to 100 pM) were used in 100 pL reaction mixtures. The inhibition constants (Ki) of carolacton on FoID were determined by measuring the apparent Km values when adding certain amounts of carolacton to the enzyme reactions. For ecFoID, 10 nM carolacton was added in the dehydrogenase assay and 50 nM carolacton was used in the cyclohydrolase assay. For spFoID, 25 nM carolacton was added in both dehydrogenase assay and cyclohydrolase assay. For hsMTHFD1_DC, 30 nM carolacton was added in the dehydrogenase assay and 10 nM in the cyclohydrolase assay. For hsMTHFD2, 20 nM carolacton was used to determine the apparent Km for 5,10-CH2-THF and 5,10-CH2-THF while 10 nM carolacton was used to determine the apparent Km for NADP. To compare the inhibition effects of carolacton between the different FoIDs, the half maximal inhibitory concentration (IC50) of carolacton on the same amount of enzyme was determined for FoIDs involved in this study. The enzyme concentration used to determine dehydrogenase activity IC50 was 10 nM, and the enzyme used for cyclohydrolase IC50 measurements was 5 nM. All enzyme kinetics measurements were performed as independent triplicates. Data processing and fitting of curves was done using OriginPro 2016 (OriginLab, Northampton, Mass., US). Analysis of variance (ANOVA) in OriginPro 2016 software gave statistical test reports after fitting curves.

Surface Plasmon Resonance Assay

All surface plasmon resonance (SPR) experiments described in this study were performed on a Biacore X100 system. Different FoIDs with or without His-tag were coupled on CM5 sensor chips (GE Healthcare) by the amine coupling method using a kit from GE Healthcare Life Sciences (Freiburg, Germany). A pH scouting process was performed before protein immobilization to test the most appropriate buffer and the protein concentration for protein coupling. Finally, 20 µg/mL of ecFoID in 10 mM maleate buffer (pH 6.8), 30 µg/mL of ecFoID Q98H in 10 mM maleate buffer (pH 6.3), 40 µg/mL of ecFoID K54N in 10 mM maleate buffer (pH 5.8), 20 µg/mL of spFoID in 10 mM maleate buffer (pH 6.0) and 15 µg/mL of MTHFD2 (His-tag cleaved) in 10 mM maleate buffer (pH 6.8) were used for coupling. In the protein immobilization procedure, the contact time was calculated based on the pH scouting results to achieve ~3000-5000 relative resonance units (RU). The buffer used in the SPR assays was 1×HBS-P buffer (10 mM HEPES pH 7.4, 150 mM NaCl, 0.05% Tween 20). The 1 mM stock solution of carolacton was prepared in 1×HBS-P buffer and diluted to different concentration ranges by two-fold serial dilution. In the SPR assay, the association time was 180 s and the dissociation time was 600 s. Data analysis was performed using the Biacore evaluation software. The SPR curves were exported to be re-plotted in OriginPro 2016 (OriginLab, Northampton, Mass., US).

Construction of Gene Deletion Mutants in Streptococci

Construction of gene deletion strains of S. pneumoniae TIGR4 and S. mutans UA159 was carried out by the PCR ligation mutagenesis method, replacing the gene of interest (GOI) with an antibiotic resistance cassette, via double homologous recombination, as previously described by Lau et al., 2002 and in more detail in the supplemental methods.

Transformation of S. pneumoniae TIGR4

Transformation of S. pneumoniae was performed by inducting competence through addition of competence stimulating peptide 2 (CSP-2) (Donner et al., 2016, Lau et al., 2002). THBY (pH 6.8) containing 1 mM $CaCl_2$ and 0.2% (w/v) bovine serum albumin (BSA) was inoculated with exponentially growing cells ($OD_{600}$~0.5) to an $OD_{600}$ of 0.005. When reaching an early log phase ($OD_{600}$~0.15), a cell aliquot (1 ml) harvested and the cells resuspended in 1 ml THBY (pH 8.0) supplemented with 1 mM $CaCl_2$, 0.2% (w/v) BSA and 400 ng/ml CSP-2. Transformation was realized by adding 10 µl of a ligation mix or 50 ng of a purified PCR product capable of chromosomal integration via double homologous recombination and static incubation at 37° C. for 2 h. Transformants were selected on THBY agar plates containing 0.5 µg/ml erythromycin and/or 2.5 µg/ml tetracycline. Correct integration was checked by PCR, Sanger DNA sequencing and RT-PCR.

Transformation of S. mutans UA159

Transformation of S. mutans UA159 was carried out according to Reck et al., 2011 An o/n culture of S. mutans was diluted to an $OD_{600}$ of 0.01 in THBY. The cells were grown to an $OD_{600}$ of approximately 0.25 and 400 ng/ml CSP supplemented. After 30 min of static incubation at 37° C. and 5% $CO_2$ 500 ng of plasmid DNA or 10 µl of a ligation mix were added. The transformation mix was incubated for another 3 h (37° C., 5% CO2) and plated onto THBY agar plates containing the appropriate antibiotics. Transformants were selected on in the presence of 10 µg/ml erythromycin, 12.5 µg/ml tetracycline and/or 10 µg/ml chloramphenicol. Correct integration was checked by PCR, Sanger DNA sequencing and RT-PCR.

S. mutans Biofilm Viability Assay

According to Reck et al., 2011, S. mutans biofilms were grown in THBY+0.5% (w/v) sucrose in the presence of 2.5 µg/ml carolacton (cf. SI Methods). Cell viability was determined by staining of 20 h-old S. mutans biofilms with the LIVE/DEAD Viability Kit (Invitrogen) and by measuring fluorescence with a Victor[3] multilabel counter (Perkin-Elmer). Subsequently, the green/red fluorescence ratio was calculated and the relative inhibition of the treated biofilms determined in comparison to the untreated control.

Reductive Methylation of Surface Lysine Residues

To protect active site lysine K54 a 6-fold molar excess of carolacton was added to the protein and the complex incubated on ice for 16 h before the reaction. Surface lysine residues were then methylated using the JBS Methylation Kit (Jena Bioscience) according to the manufacturer's instructions. Methylated ecFoID (ecFoID$^{Meth}$) and ecFoID$^{meth}$Q98H were applied to a Superdex 200 gel filtration column (GE Healthcare) pre-equilibrated with gel filtration buffer (150 mM NaCl, 10 mM HEPES (pH 7.4), 1 mM TCEP), and then concentrated to 5 mg/mL.

X-ray Crystallography

Crystals of ecFoID$^{meth}$ were obtained at 18° C. by using the sitting drop vapor diffusion method. 300 nL protein at 5 mg/mL were added to 150 nL reservoir solution: 0.2 M sodium acetate, 0.1 M sodium cacodylate pH 6.5 and 30% (w/v) PEG 8000. To solve the ecFoID-carolacton complex structure, ecFoID$^{Meth}$ crystals were soaked overnight in the presence 2 mM carolacton. Optimized crystals of apo-ecFoID$^{Meth}$Q98H were grown under conditions of 0.2 ammonium sulfate, Bis-Tris pH 6.0 and 25% PEG 3350. Diffraction data for all proteins was collected from single crystals at 100 K. Data for ecFoID$^{Meth}$ was obtained at Beamline X06DA at a wavelength of 1 Å (Swiss Light Source) while data for the ecFoID$^{Meth}$-carolacton complex and ecFold$^{Meth}$Q98H crystals were collected at beamline ID30-A3 (ESRF) at a wavelength of 0.967 Å. Data was processed using Xia2 (Winter et al., 2010) or XDS (Kabsch et al., 2010) and the structures solved using PHASER (McCoy et al., 2010) Molecular Replacement with ecFoID (PDB ID 1DIA) as a search model. The models were manually rebuilt with COOT (Emsley et al., 2010) and refined using PHENIX(Adams et al., 2010) and Refmac5 (Skubak et al., 2004). The structure was validated using MolProbity and all images were presented using PyMOL (The PyMOL Molecular Graphics System, Version 1.8 Schrödinger, LLC). Interaction diagrams were created using Ligplot (Laskowski et al. 2011).

Construction of Gene Deletion Mutants in Streptococci

The up- and downstream regions flanking the gene of interest (GOI) were amplified by PCR, thereby adding an FseI and an AscI restriction site into the PCR products. An erythromycin (erm$^R$) resistance cassette was amplified by PCR from pALN122 (Marcrina et al., 1983). After purification (QIAquick PCR Purification Kit, Qiagen), all PCR products were digested with the appropriate restriction enzymes. 50-100 ng of DNA fragments was ligated with T4 DNA ligase at 16° C. o/n and subsequently used for transformation of S. pneumoniae or S. mutans. All enzymes were purchased from New England Biolabs (NEB).

Deletion of the foID Gene in S. pneumoniae

For deletion of foID in S. pneumoniae, the foID gene was cloned into pJWV25. For this, pJWV25 was linearized with primers pJWV25_fwd/ pJWV25_rev and foID of S. pneumoniae TIGR4 was amplified with foID_pJWV25_fwd/foID_pJWV25_rev. This resulted in plasmid pJAD35, containing a copy of the foID gene under control of a zinc-inducible promoter ($P_{czc}$-foID). The construct was amplified from pJAD35 with primers trafo_spn_fwd/trafo_spn_rev, including sequences necessary for integration into the *S. pneumoniae* chromosome. The resulting strain (TIGR4 bgaA::$P_{czcD}$-foID) was subsequently used for deletion of foID, using the previously unsuccessful PCR ligation mutagenesis approach. This was done in the presence of 0.15 mM ZnCl2 for induction of expression of FoID. This gave rise to strain TIGR4foID bgaA::$P_{czcD}$-foID, which was used for PCR amplification of the foID locus, now containing an erythromycin resistance cassette within foID (foID_up_fwd/foID_up_rev). 500 ng of purified PCR product were then successfully used for deletion of foID in the *S. pneumoniae* TIGR4 wild type (TIGR4ΔfoID).

Complementation of foID Mutants of *S. pneumoniae* and *S. mutans*

For complementation of the *S. pneumoniae* ΔfoID strain, a native copy of foID under control of the original promoter was integrated into the non-essential beta-galactosidase gene bgaA, using a derivative of pJWV25 (Eberhardt et al., 2009). First, pJWV25 was linearized (pJWV25_fwd/pJWV25_rev) and the amplificate of the *S. pneumoniae* TIGR4 foID locus (primers foID_pJWV25_fwd and foID_pJWV25_rev) cloned into the linearized vector by using the CloneEZ PCR Cloning Kit (GenScript). A fragment of the recombinant plasmid pJAD36 (containing the $Pf_{foID}$-foID construct, flanked by the spr_0564 and bgaA fragments required for double homologous recombination) was amplified via PCR using primers trafo_spn_fwd and trafo_spn_rev, purified and used for transformation of *S. pneumoniae* TIGR4.

*S. mutans* ΔfoID was complemented with a plasmid-borne copy of FoID by first amplifying pIB166 (pIB166_fwd/pIB166_rev) and foID$_{Smu}$ (foIDplB_fwd/foIDplB_rev) by PCR. The PCR product containing the *S. mutans* foID locus was then blunt-end cloned into the linearized pIB166 using T4 ligase (NEB) at 16° C. o/n. The ligation mix was then used for transformation of *E. coli* DH5α (see below). The resulting plasmid, pIB166-foID, was finally used for transformation of *S. mutans* UA159.

Isolation of RNA from *S. pneumoniae* and *S. mutans*

RNA of streptococci was isolated from exponentially growing cells in planktonic culture (THBY). 5 ml cell culture was mixed with 5 ml RNA Protect solution, incubated at RT for 5 min, the cells harvested by centrifugation and frozen at −80° C.

For homogenization, the cell pellet was resuspend the pellet in 700 µl QIAzol lysis reagent, transferred to a 15 ml Falcon reaction tube and the cells lysed by vortexing (3 min) after addition of 50 mg of acid-washed glass beads (100 microns D, Karl Roth GmbH). Subsequently, isolation RNA was accomplished using the miRNeasy Mini Kit (Qiagen), following the protocol for isolation of total cellular RNA according to the kits manual. Before elution of total RNA from the column, an optional DNaseI digestion was performed. An additional DNaseI digestion step was included after the elution of RNA to ensure complete absence of contaminating DNA. Furthermore, 2 µl of total RNA extract was used in a PCR reaction (30 cycles, NEB Phusion-Polymerase) to confirm absence of any remaining chromosomal DNA.

Verification of foID Deletion Mutants by Reverse-transcription PCR (RT-PCR)

Reverse transcription of isolated RNA was carried out with the QuantiTect Reverse Transcription Kit (Qiagen) according to the manufacturer's instructions. Subsequently, 1 µl of the reverse transcription reaction was used in a regular PCR reaction, using the primer pairs for foID (foID_RT_fwd/foID_RT_rev) and the constitutively expressed D-alanine:D-alanine ligase A gene ddlA (ddlA_RT_fwd/ddlA_RT_rev), as a positive control, for *S. pneumoniae*. Primers foIDSmu_RT_fwd/foIDSmu_RT_rev were used specific for *S. mutans* foID. PCR products were visualized using 1.5% (w/v) TAE agarose gel electrophoresis.

Biofilm Experiments of *S. mutans*

For determination of Carolacton-induced cell death of *S. mutans* biofilms, o/n cultures of *S. mutans* were diluted to an $OD_{600}$ of 0.01 in THBY+0.5% (w/v) sucrose. 10 µl of a Carolacton solution (2.5 µg/ml and 0.25 µg/ml in methanol) was pipetted into the wells of black a 96-well polystyrene Nunc MicroWell plates with transparent bottoms (ThermoFisher); control wells contained 10 µl of methanol. The methanol was evaporated and 200 µl of the *S. mutans* cell dilutions ($OD_{600}$ 0.01) added to each well. For each treatment and strain, at least six technical replicates per plate and three biological replicates were prepared. Plates were incubates statically at 37° C. and 5% $CO_2$ for 20 h and then used in Live/Dead staining experiments.

Live/Dead Staining of *S. mutans* Biofilms

The viability of *S. mutans* biofilm cells was assayed by staining with the commercially available Live/Dead staining kit (Invitrogen). The supernatants were removed and the biofilms washed twice with a 0.85% (w/v) NaCl solution. For staining, 100 µl of a dilution of propidium iodide (PI)/Syto 9 (15 pl of each in 10 ml 0.85% NaCl) was pipetted into the wells and the cells stained for 30 min in the dark. Green and red fluorescence values of stained cells were measured using a Victor$^3$ fluorescence plate reader (PerkinElmer). The green/red ratio of treated and untreated cells was calculated and the relative cell death within Carolacton-treated biofilms determined relative to the untreated controls (Reck et al., 2011).

Microscopy of *S. pneumoniae* Cells

*S. pneumoniae* cells growing in THBY or *S. mutans* biofilm cells were washed with 0.85% (w/v) NaCl solution and pipetted onto a microscope slide coated with a thin layer of 1% (w/v) agarose. Phase-contrast microscopic analysis of cells was performed using an Olympus BX60 microscope equipped with an Olympus DP50 color camera (5 Mpixel) color view II camera and a 100× magnification oil immersion objective. Pictures and measurements were taken with the Olympus cellSens (v1.6) microscopy software.

Cell Proliferation Assay with Mouse Fibroblasts

L-929 mouse fibroblasts from DSMZ cultivated at 37° C. and 10% $CO_2$ in DME medium (high glucose) supplemented with 10% fetal calf serum. Cell culture reagents came from Life Technologies Inc. (GIBCO BRL). 60 pL of serial dilutions of the test compound were given to 120 pL of suspended cells (50,000/mL) in wells of 96-well plates. After 5 days of incubation growth inhibition (IC50) was determined using an MTT assay (Mosman et al., 1983).

Toxicity Assay

L-929 mouse fibroblasts from DSMZ cultivated at 37° C. and 10$CO_2$ in DME medium (high glucose) supplemented with 10% fetal calf serum. Cell culture reagents came from Life Technologies Inc. (GIBCO BRL). 120 pL of sus-pended cells (100,000/mL) were seeded into wells of 96-well plate. After 4 days when the cells had formed a confluent layer, 60 pL of serial dilutions of the test compound were added to the cells. After 18 hours of incubation metabolic activity of the cells was determined using an MTT assay (Mosman et al., 1983).

Testing of Tumor Cell Lines

To evaluate the effects of one compound on 7 cell lines with a CellTiter-Glo Luminescent Cell Viability Assay. Cells were treated with compounds for 72 hours at 37° C./5% CO2 incubator. Compound stock concentration was 20 mM, concentrations to be assayed 100\50\15\10.5\0.1\0.05\0.01\0.005 pM.

i) Materials and Reagents
a) IMDM Medium, Gibco, Cat #12440-053
b) RPMI 1640 Medium, Gibco, Cat #22400-098
c) FBS, Gibco, Cat #10099-141
d) 0.25% Trypsin-EDTA, Gibco, Cat #GB25200-072
e) CellTiter-Glo® Luminescent Kit, Promega, Cat #G7571
f) 6-well plate, Coring, Cat #3516 g) 10-cm cell culture dish, Corning, Cat #430167
h) 50 ml centrifuge tube, Corning, Cat #430828
i) 384-well flat clear bottom white, Corning, Cat #3707 ii) Assay procedures
a) Cells in log-phase are collected and counted. Cell suspensions are added to each well of 384-w plate at a suitable density. The margin wells are filled with PBS.
b) Test compound at various concentrations are added in duplicates
c) The cells were incubated for 72 h in 370/5% CO 2 incubator.
d) After incubation, CellTiter-Glo® Reagent is added to each test well and shack for 2 minutes on an orbital shaker.
e) The plates are shortly centrifuged at 90×g for 30 s and incubated at room temperature for additional 10 minutes to stabilize the luminescent signal.
f) Luminescence signals are detected on PHERAstar Plus.
g) Data is collected in Microsoft excel forms and analyzed with GraphPad Prism v.6 software.

iii) Data analysis

The potential effect of the testing compounds an cell proliferation was calculated by the formula below: Inhibition %=[(1−RLU$_{compound}$)/(RLU$_{1\% \ DMSO}$)]×100%

Results of the Examples

FoID is the Carolacton Target

To facilitate the identification of the molecular target of carolacton, E. coli ToIC (E. coli without efflux pump ToIC) was chosen to develop carolacton-resistant mutants. This strain is easy-to-handle, non-pathogenic and susceptible to carolacton. After one week, carolacton-resistant mutants arose spontaneously on agar plates supplemented with 4 times the carolacton minimum inhibition concentration (MIC=0.125 μg/ml). Genome sequencing of independent mutants unveiled that only the gene that encodes FoID was mutated. Four different mutations conferring resistance were identified: G8S (observed in two mutants), K54N, Q98H and ΔK54R55. To validate FoID as the carolacton target and to understand the potential mechanism of action (MoA), E. coli ToIC FoID (ecFoID) was overexpressed and purified from E. coli BL21 (DE3). A SDS-PAGE of all proteins used, as well as their LC-MS analysis, can be found in FIG. 6. The purified FoID showed DH and CYH activity comparable to previously reported bacterial FoIDs (Eadsforth et al., 2012b, Clark et al., 1982, Wohlfarth et al., 1991), including the DH activity of E. coli FoID (D'Ari et al., 1991). DH and CYH activity was found to be much stronger than reported for ecFoID in two other studies (Table 5). This discrepancy has been noted previously and possible reasons include impurities (D'Ari et al., 1991, Dev et al., 1978) and excessive enzyme concentrations used for enzyme kinetics (Sah et al., 2015a). When carolacton is added to the reaction, we observe strong inhibition of both steps catalyzed by ecFoID (DH and CYH) in a carolacton concentration-dependent manner (FIG. 2A). In addition, carolacton showed competitive inhibition with both substrates and the cofactor involved in DH and CYH catalytic steps, which are 5,10-$CH_2$-THF ($K_i$=21 nM), $NADP^+$ ($K_i$=11 nM) and 5,10-CH=THF ($K_i$=32 nM) (Table 1), as the apparent Michaelis constant ($K_M$) increased when carolacton was added (FIG. 8). This finding indicated that wild-type (wt) ecFoID is indeed the target of carolacton. To confirm that both molecules interact, we then tested wt ecFoID for its ability to bind carolacton using surface plasmon resonance (SPR). The interaction we observed between wt ecFoID and carolacton was very strong ($K_D$=10 nM), further confirming ecFoID as the carolacton target (FIG. 2B).

The Structure of the ecFoID—Carolacton Complex

To understand how carolacton binds to ecFoID and thus rationalize the mutations giving rise to carolacton resistance, we determined the crystal structure of ecFoID in complex with carolacton. The originally reported crystallization conditions for ecFoID (Shen et al., 1999) yielded only poorly diffracting crystals in our hands. Reductive lysine methylation ecFoID$^{meth}$ gave a new crystal form that diffracted well. Since a key active-site residue of ecFoID is a lysine (K54) (Schmidt 2000), and we found that mutations at this position conferred carolacton resistance (see resistant mutants above), we thought that K54 could be involved in carolacton binding and thus we sought to protect this residue from methylation. To this end we incubated ecFoID with an excess of carolacton before lysine methylation. After the reaction, carolacton was removed via size exclusion chromatography and the resultant ecFoID$^{Meth}$ tested for activity. We observed only a slight decrease in enzyme activity and no significant change of carolacton's ability to inhibit ecFoID DH activity (FIG. 21). To further analyze whether we had methylated active-site K54, we first determined the apo-structure of ecFoID$^{Meth}$. The protein crystallized in space group $P2_1$ and crystals diffracted to 1.9 Å resolution (PDB ID 5o28). Full data collection and refinement statistics for all structures can be found in Table 2. ecFoID$^{Meth}$ showed the canonical dimeric arrangement observed in the structures of ecFoID (PDB ID 1B0A) (Shen et al., 1999) and its orthologs (Gustafsson et al., 2017, Allaire et al., 1998) and the overall structure was virtually unchanged when compared to unmethylated protein (FIG. 9). We observed unambiguous electron density for methylated lysines at positions K4, 22, 194, 212 and 222. With the exception of K22, all of them can be found at crystal contacts (FIG. 10). We observed density for unmethylated active-site K54, supporting our biochemical data that indicated this lysine was not methylated (FIGS. 10 and 11). We soaked the apo crystals of ecFoID$^{Meth}$ with 2 mM carolacton and harvested them after 16 h. The soaked crystals diffracted to 2.1 Å (PDB ID 5o22) and showed strong additional density at the protein's active site in three of the four monomers of the asymmetric unit (protomers A, B and D, the picture in protomer C is skewed due to a crystal contact). Carolacton can be fitted into the additional density (FIG. 2c) and refines well (FIG. 10). Binding of carolacton to FoID has a minimal impact on FoID's overall structure (Cα rmsd 0.27 Å) and is facilitated by 3 hydrogen bonds (K54 ε-amino group with carolacton O8 and O33 and G261 main chain N with carolacton O29) and several hydrophobic interactions (Y50, I170, I232, P260, P265 and V268) (FIGS. 2c, 2d and 12). The hydrophobic interaction between carolacton and Y50 causes a partial disruption of helix α2 (Residues 45-56) and allows the Y50 hydroxyl group to form a hydrogen bond with the side-chain of R234 (FIG. 2d). When carolacton is bound, the N-terminal residues of α2 and a part of the loop connecting β1 with α2 (Residues 41-44) become disordered (Residues 44-49). It has been noted by others that this part of FoID is unstable (Schmidt et al., 2000, Gustafsson et al., 2017), and we observe only poor density for residues 44-56 in the ecFoID$^{Meth}$ apo structure (protomers A, B, and D; protomer C behaves differently due to a crystal contact). We believe that this reflects a catalytic mechanism, in which a meta-stable helix (α2) harbors a residue essential for catalysis. Upon substrate (or carolacton) binding, Y50 engages in hydrophobic contact which completely destabilizes residues 44-49, while the other half of the helix is stabilized (residues 50-56) (FIG. 2d).

When the FoID—carolacton complex structure is superposed onto the human ortholog of FoID (PDB ID 1DIA), which was co-crystallized with NADP$^+$, and substrate analog LY249543, it can be seen that carolacton is likely to prevent binding of both co-factor and substrates (FIG. 13a, b).

Effects of ecFoID Mutations on Enzyme Activity and Carolacton Binding

The effects of mutations K54N and G8S on carolacton binding can easily be explained by the complex crystal structure. K54 provides two hydrogen bonds to anchor carolacton in the active site of ecFoID (FIG. 2c) and its mutation to N will severely affect binding of carolacton to ecFoID. G8 is not in direct contact with carolacton, but its position and orientation in FoID implies that the addition of any side-chain will cause a clash with C-terminal helix α11 (FIG. 14). G261, which forms a hydrogen bond with carolacton, is part of this helix and we assume that the resulting movement of helix α11 leads to a clash with the carboxyl group of carolacton. Due to the very tight fit of carolacton in this area, the clash cannot be remedied but instead leads to severely reduced binding of carolacton to ecFoID. Helix α2 is vital for binding of carolacton to FoID, since it contains both K54 and Y50. It was therefore not unexpected that the deletion of two residues from this helix (mutant ecFoIDΔK54R55) severely affected binding of carolacton to FoID. The final mutation, Q98H, could not be rationalized using the complex structure and we wondered if this mutation does in fact affect binding of carolacton to ecFoID or is an experimental artifact.

To test experimentally the effects of the mutations that we discovered in carolacton resistant E.coli ΔtolC, we expressed and purified all 4 mutant proteins: ecFoIDG8S, ecFoIDK54N, ecFoIDΔK54R55 and ecFoIDQ98H. When we tested the mutants for DH activity, we found that all of them were attenuated, but with varying severity. The mutant K54N still retains ~19% of the wild-type (wt) DH activity but ΔK54R55 has only ~1% DH activity left. The two-residue deletion might severely change the NADP$^+$ binding, which can be deduced from the dramatically increased $K_M$ of NADP$^+$. The DH activity of G8S and Q98H is about 21% and 8% of the wt, respectively (FIG. 3a and Table 3).

Mutants K54N and ΔK54R55 showed no detectable CYH activity, suggesting that K54 is essential for this reaction. The kinetic properties of the CYH activity of mutants G8S and Q98H were not investigated since only very low CYH activity was detected. We estimate residual activity of ~1% based on the requirement to increase the enzyme concentration ~100-fold to achieve wt turnover (FIG. 15). The mutant E. coli ΔtolC strains likely survive without CYH activity because the turnover of 5,10-CH=THF to 10-CHO-THF can occur spontaneously (Maden et al., 2000).

The mutants G8S and Q98H could still be inhibited by carolacton but with much higher IC$_{50}$ compared to the wt (FIG. 3b and Table 4). The central role of K54 is highlighted by the fact that the residual DH activity of K54N and ΔK54R55 is completely insensitive to carolacton (FIG. 3b), in accordance with the SPR data that indicated that carolacton does not bind to K54N (FIG. 16b). It appears that, under selection pressure, viable mutants had sacrificed CYH activity (reaction can be spontaneous) but required retention of FoID's DH activity since no alternative pathway exists in E. coli (Sah et al., 2015).

The binding of carolacton to ecFoID Q98H was seriously attenuated as reflected by the SPR data (FIG. 16c, d). To understand how the mutation Q98H affects the binding of carolacton we determined the crystal structure of this mutant (PDB ID 5o2a). After lysine methylation, this protein crystallized in the same space group as the wt protein and crystals diffracted to 1.9 Å. The overall structure of ecFoID$^{Meth}$Q98H is not altered when compared to wt as a result of the mutation (Cα rmsd 0.11 Å) and the effect of the Q98H mutation was unexpected. The presence of H98 allows the side-chain of Y50 to rotate 90° compared to the apo wt ecFoID structure. It appears that in the wt protein, Q98 helps to position the side-chain of Y50 such that it can easily rotate to engage in hydrophobic interactions with carolacton upon binding. In Q98H the side-chain of Y50 is able to rotate farther from the active site and packs against residues V38, L40, L96, and H98. The result is a fully ordered helix α2 with good density for all residues, which we believe reflects a stabilization of the protein. The absence of the hydrophobic interaction between carolacton and Y50 leads to significantly weakened binding, which we believe to be reflected by the much faster association and dissociation of carolacton in SPR experiments with ecFoIDQ98H (FIG. 3c,d, FIG. 16c).

Effects of Carolacton on Streptococci

Carolacton was originally discovered as an anti-streptococci compound (Jansen et al., 2010, Kunze et al., 2010) and the FoID ortholog from S. penumoniae (spFoID) shares 49% sequence identity with ecFoID. The key residues involved in carolacton binding are conserved and carolacton binds tightly to spFoID ($K_D$=27 nM) (FIG. 16A). Carolacton also showed competitive inhibition on spFoID with slightly higher inhibition constants than ecFoID, which were still in the low nM range (FIG. 17 and Table 1 and 4).

The in vivo situation in streptococci is complicated by the fact that these bacteria possess the enzyme Fhs and thus a FoID-independent route to 10-CHO-THF (FIG. 1, Crowley et al. 1997, Sah et al., 2015b). It has been reported that heterologous expression of Fhs in E. coli can compensate for a deletion of foID, although the mutants are auxotrophic for purines and glycine Sah et al., 2015b). To investigate the in vivo effect of carolacton on streptococci, a series of gene deletions and complementations were conducted. Upon deletion of foID, biofilms of the caries-associated pathogen S. mutans become fully insensitive to carolacton treatment (FIG. 19A) and S. pneumoniae becomes carolacton resistant (FIG. 4A). The effects of the foID deletion on the overall fitness of the bacteria were similar: the density of S. mutans biofilms and growth of planktonic cells of S. pneumoniae were not affected in the foID mutants. However, mature and acidic biofilms of S. mutansΔfoID showed an overall reduced proportion of live cells similar to carolacton-treated biofilms of the wt. This is likely due to loss of the protective function of S. mutans FoID at low pH, through deletion and inhibition in the mutant and wt, respectively. When foID was complemented, the susceptibility of streptococci to carolacton was only partially restored, which may be the result of positional effects (FIG. 4A and 19A). To test whether Fhs served as the alternative route to 10-CHO-THF we generated a *S. pneumoniae* mutant in which fhs was inactivated. We observed complete inhibition of this mutant by carolacton, indicating that Fhs provides the backup path to 10-CHO-THF (FIG. 4B and 19B), which is sufficient to render streptococci partially resistant to carolacton.

Effects of Carolacton on the Human FoID Orthologs MTHFD1 and MTHFD2

As mentioned above, FoID analogues are also present in higher organisms such as humans. The human enzymes hsMTHFD1_DC and hsMTHFD2 both share 42% sequence identity to ecFoID. The key residues involved in carolacton binding are fully conserved and the structures of hsMTHFD1_DC and hsMTHFD2 are well conserved when compared to ecFoID (pairwise Cα rmsds of 1.09 Å and 0.84 Å, respectively, FIG. 20). Carolacton could therefore also serve as an inhibitor of the human enzymes. Since the mitochondrial hsMTHFD2 is overexpressed in many tumor cells its inhibition may cause a selective effect on tumor growth (Nilsson et al., 2014). We therefore expressed and purified hsMTHFD2 and hsMTHFD1_DC to test them biochemically. The inhibition of hsMTHFD2 and hsMTHFD1_DC by carolacton is similar to those observed for ecFoID (FIG. 5A).

The $K_i$ of carolacton against all three substrates and the cofactor were also determined and are in the same range as those for ecFoID (FIG. 18 and Tables 1 and 4). When the binding of carolacton to hsMTHFD2 was analyzed by SPR, we found strong binding on par with the bacterial proteins ($K_D$=19 nM) (FIG. 5B).

Inhibition of Cell Proliferation of Tumor Cells by Carolacton

Since hsMTHFD2 is expressed in human mitochondria and overexpressed in many tumor cells we next aimed to evaluate its potential as an anticancer compound. To this end IC50 values for carolacton were determined for six different cancer cell lines as well as HUVEC cells as primary non-tumor cells. The CellTiter-Glo luminescent cell viability assay (Promega) was used on triplicate cultures grown for three days. Each cell line was tested in three independent experiments (performed at different times and by different experimentators): First, using natural carolacton purified from culture supernatants of *Sorangium cellulosum* and solved in methanol; second, using carolacton synthesized de novo according to Schmidt et al. 2012 and solved in DMSO; and third, using synthetic carolacton synthesized de novo according to Schmidt et al. 2012 and solved in methanol.

Table 6 shows that carolacton inhibits proliferation of malignant NK-92 cells with IC50 values as low as 37-39 nM. Lymphoma cells (U-937) are inhibited at IC50 values between 6.8 nM and 44.7 nMol. Similar results, although with higher IC50 values, were obtained for leukemia, colon cancer and ovary cancer cells. Gastric cancer cells could also be inhibited albeit less pronounced. HUVEC cells were significantly less sensitive to Carolacton, with IC50 values of 46.4 and 48.3 pMol respectively. There was no significant difference between natural and synthetic Carolacton, proving that the activity observed here cannot be due to contamination by Epothilon, a potent cancer drug which is synthesized by the same strain of *S. celluolosum*. DMSO affects the viability of NK-92 cells which were killed by it and also of HUVEC cells, which required twice the amount of carolacton to get inhibited when carolacton was applied solved in DMSO compared to methanol.

The data thus further shows the potency of Carolacton as an inhibitor of cancer proliferation in numerous cancer types including malignant lymphoma, lymphoma, leukemia, colon cancer, ovary cancer or gastric cancer.

Activities of Carolacton Derivatives

Furthermore three synthetic carolacton derivates Ja 212, Ja320, Ja310 (FIG. 22) were generated and tested for their activity. The derivatives were prepared based on the established procedure reported by Schmidt et al. 2012 which was modified accordingly.

First the impact of the derivatives on biofilm formation of *Streptococcus mutans* was accessed. To this end natural carolacton and the three derivatives Ja320, Ja310, Ja212 were tested for their ability to damage biofilms in the concentration range 1 mM-100 pM according to Kunze et al., 2010. As shown in FIG. 23 Ja320 exhibits a similar inhibition potential as the natural carolacton.

Next the impact of the derivatives planktonic growth of *S. pneumoniae* was determined. Natural Carolacton, the three derivatives Ja212, Ja310 and Ja320 were tested at 0.25 pg/ml for inhibition of planktonic growth of *S. pneumoniae* TIGR according to Donner et al., 2016. Ja263 served as a control. FIG. 24 depict the results, which indicate an identical activity of Ja320 with carolacton.

In order to access the toxicity of the synthesized compounds in comparison to natural carolacton the inhibition of proliferation of mouse fibroblast cell line L929 was determined.

Toxicity of carolacton was determined after 18 h and the data show that Carolacton had no acute toxicity as shown previously (Kunze et al., 2010)

Natural Carolacton and the synthetic derivatives Ja212, Ja320 and Ja310 were tested for their ability to inhibit proliferation of mouse fibrobast cells cultivated for 5 days. Carolacton inhibited growth of L929 cells but without reaching more than 50% inhibition. Therefore an adapted IC50 was determined to be 3,5 pg/ml. Ja212 and Ja310 were inactive, while Ja320 showed weak inhibition of mouse fibroblasts with an adapted IC50 of >37 pg/ml (FIG. 24).

The data show that it is possible to tune the specificity of carolacton derivatives to the intended application. Ja320 has the same activity as natural Carolacton against *S. pneumoniae*, but weaker activity against *S. mutans* biofilms and mouse fibroblast cells.

TABLE 1

The inhibition constants of carolacton against wt FoID.

| enzyme | carolacton inhibition on DH activity | | carolacton inhibition on CYH activity |
|---|---|---|---|
| | Ki (nM) (5,10-CH2—THF) | Ki (nM) (NADP+)[a] | Ki (nM) (5,10-CH=THF) |
| ecFoID | 21.31 | 10.91 | 31.60 |
| spFoID | 42.18 | 34.21 | 38.07 |
| hsMTHFD1 DC301 | 5.93 | 58.69 | 20.59 |
| hsMTHFD2 | 6.42 | 16.69 | 12.67 |

[a]it is nicotinamide adenine dinucleotide (NAD) in the case of hsMTHFD2

TABLE 2

| Data collection and refinement statistics | | | |
|---|---|---|---|
| | Apo-FolD$^{Meth}$ | FolD$^{Meth}$-caro | FolD$^{Meth}$Q98H |
| Data collection | | | |
| Space group | P1 2$_1$ 1 | P1 2$_1$ 1 | P1 2$_1$ 1 |
| Cell dimensions | | | |
| a, b, c (Å) | 99.6, 79.8, 101.4 | 99.7, 81.1, 101.0 | 100.1, 79.4, 101.8 |
| α, β, γ (°) | 90.0, 113.3, 90.0 | 90.0, 112.9, 90.0 | 90.0, 113.8, 90.0 |
| Resolution (Å) | 1.89 (1.94-1.89) | 2.10 (2.21-2.10) | 1.90 (2.00-1.90) |
| R$_{merge}$ | 8.4 (79.80) | 9.1 (60.6) | 6.1 (54.1) |
| I/σI | 17.9 (2.4) | 10.4 (2.5) | 22.1 (4.4) |
| Completeness (%) | 99.8 (98.9) | 98.9 (99.8) | 98.9 (99.2) |
| Redundancy | 6.7 (6.5) | 4.4 (4.5) | 9.7 (9.9) |
| Refinement | | | |
| Resolution (Å) | 36.59-1.89 | 45.88-2.10 | 46.56-1.90 |
| No. reflections | 116,659 | 85,476 | 113,624 |
| R$_{work}$/R$_{free}$ | 0.190/0.216 | 0.175/0.206 | 0.186/0.198 |
| No. atoms | | | |
| Protein | 8640 | 8441 | 8658 |
| Ligand/ion | | 132 | |
| Water | 1014 | 588 | 876 |
| B-factors | 36.22 | 42.23 | 34.75 |
| Protein | 35.90 | 41.65 | 33.97 |
| Ligand/ion | | 69.76 | |
| Water | 38.92 | 44.16 | 42.51 |
| R.m.s. deviations | | | |
| Bond lengths (Å) | 0.003 | 0.005 | 0.013 |
| Bond angles (°) | 0.65 | 0.70 | 1.11 |

TABLE 3

Enzyme kinetic parameters for FolD enzymes.

Dehydrogenase

| enzyme | substrate | K$_m$ (μM) | k$_{cat}$ (s$^{-1}$) | k$_{cat}$/K$_m$ (s$^{-1}$ μM$^{-1}$) | Specific activity (μmol min$^{-1}$ mg$^{-1}$) |
|---|---|---|---|---|---|
| ecFolD | 5,10-CH$_2$—THF | 76.47 ± 8.27 | 90.34 ± 3.29 | 1.18 | 173.57 ± 6.32 |
| | NADP | 186.51 ± 21.02 | 89.64 ± 3.54 | 0.48 | 172.22 ± 6.81 |
| ecFolD G8S | 5,10-CH$_2$—THF | 179.44 ± 26.56 | 20.27 ± 1.75 | 0.11 | 35.67 ± 3.08 |
| | NADP | 510.80 ± 35.67 | 20.74 ± 0.71 | 0.04 | 36.50 ± 1.25 |
| ecFolD K54N | 5,10-CH$_2$—THF | 27.03 ± 1.85 | 18.19 ± 0.39 | 0.67 | 32.06 ± 0.39 |
| | NADP | 173.31 ± 21.66 | 16.00 ± 0.40 | 0.09 | 28.20 ± 0.68 |
| ecFolD ΔK54R55 | 5,10-CH$_2$—THF | 61.75 ± 7.29 | 0.81 ± 0.03 | 0.01 | 1.44 ± 0.06 |
| | NADP | 675.63 ± 86.00 | 1.16 ± 0.06 | 0.0017 | 2.06 ± 0.11 |
| ecFolD Q98H | 5,10-CH$_2$—THF | 160.57 ± 15.87 | 8.28 ± 0.34 | 0.05 | 14.58 ± 0.59 |
| | NADP | 311.53 ± 55.44 | 6.67 ± 0.45 | 0.02 | 11.75 ± 0.79 |
| spFolD | 5,10-CH$_2$—THF | 76.52 ± 9.25 | 68.10 ± 3.11 | 0.89 | 118.69 ± 5.42 |
| | NADP | 70.33 ± 5.53 | 62.30 ± 1.02 | 0.89 | 108.59 ± 1.77 |
| hsMTHFD1 DC301 | 5,10-CH$_2$—THF | 5.54 ± 0.66 | 4.32 ± 0.35 | 0.78 | 7.15 ± 0.59 |
| | NADP | 27.13 ± 6.55 | 4.85 ± 0.58 | 0.18 | 8.04 ± 0.96 |
| hsMTHFD2 | 5,10-CH$_2$—THF | 37.29 ± 8.05 | 15.04 ± 1.14 | 0.40 | 25.70 ± 1.95 |
| | NADP | 171.67 ± 9.28 | 33.12 ± 0.43 | 0.19 | 28.29 ± 0.74 |

Cyclohydrolase

| enzyme | substrate | K$_m$ (μM) | k$_{cat}$ (s$^{-1}$) | k$_{cat}$/K$_m$ (s$^{-1}$ μM$^{-1}$) | Specific activity (μmol min$^{-1}$ mg$^{-1}$) |
|---|---|---|---|---|---|
| ecFolD | 5,10-CH=THF | 26.63 ± 6.77 | 155.53 ± 19.71 | 5.84 | 298.81 ± 37.87 |
| spFolD | 5,10-CH=THF | 41.08 ± 8.38 | 91.33 ± 7.97 | 2.22 | 159.17 ± 13.88 |
| hsMTHFD1 DC301 | 5,10-CH=THF | 42.61 ± 9.39 | 137.56 ± 13.93 | 3.23 | 227.79 ± 23.07 |
| hsMTHFD2 | 5,10-CH=THF | 16.14 ± 3.69 | 242.44 ± 22.41 | 15.02 | 414.23 ± 38.29 |

TABLE 4

The IC50 and IC80 values determined for carolacton inhibition on different FoID enzymes.

| enzyme | carolacton inhibition on DH activity | | carolacton inhibition on CYH activity | |
|---|---|---|---|---|
| | $IC_{50}$ (nM) | $IC_{80}$ (nM) | $IC_{50}$ (nM) | $IC_{80}$ (nM) |
| ecFoID | 15.49 | 52.22 | 49.83 | 180.01 |
| ecFoID G8S | 86.49 | 736.59 | ND | ND |
| ecFoID K54N | ND[a] | ND | ND | ND |
| ecFoID ΔK54R55 | ND | ND | ND | ND |
| ecFoID Q98H | 313.21 | 1931.66 | ND | ND |
| spFoID | 36.80 | 168.90 | 38.09 | 101.34 |
| hsMTHFD1 DC301 | 38.05 | 77.58 | 19.45 | 67.54 |
| hsMTHFD2 | 6.50 | 31.71 | 85.73 | 201.78 |

[a]ND means not determined because either the enzymatic activity is totally abolished or too low or the enzymatic activity is not affected.

TABLE 5

The specific activity of dehydrogenase and cyclohydrolase of bacterial FoID reported herein and previous studies.

| Bacteria | FoID | DH activity (specific activity μmol min−1 mg−1) | CYH activity (specific activity μmol min−1 mg−1) | Reference |
|---|---|---|---|---|
| E. coli | ecFoID | 173.57 ± 6.32 | 298.81 ± 37.87 | This study |
| Acinetobacter baumannii | abFoID | 161.4 ± 5.7 | 350.2 ± 4.4 | Eadsforth et al. |
| E. coli | ecFoID | 200 | 33 | D'Ari et al. |
| E. coli | ecFoID | 31.2 | 6.12 | Dev et al. |
| E. coli | ecFoID | 19 | 39 | Sah et al. |
| Peptostreptococcus productus | ppFoID | 627 | ND | Wohlfarth et al. |
| Clostridium formicoaceticum | cfFoID | ND | 469 | Clark et al. |

TABLE 6

IC50 values for inhibition of cancer cell proliferation by Carolacton. Carolacton was tested between 0.005 pM and 100 pM, doxorubicin served as internal control. C Carolacton.

| | Cell line | $IC_{50}$ (M) | Hillslope | Top | Bottom | Comments |
|---|---|---|---|---|---|---|
| malignant lymphoma | NK-92 | 3.99E−08 | 1.97 | 91.08 | −9.96 | natural C, methanol |
| | NK-92 | >0.0001 | | | | synthetic C, DMSO |
| | NK-92 | 3.67E−08 | 2.261 | 91.05 | 1.208 | synthetic C, methanal |
| Lymphoma | U-937 | 1.07E−08 | 2.648 | 67.6 | =0.0 | natural C, methanol |
| | U-937 | 4.47E−08 | 2.002 | 61.59 | 1.808 | synthetic C, DMSO |
| | U-937 | 6.84E−09 | 5.528 | 60.9 | 0 | synthetic C, methanol |
| Leukemia | THP-1 | 8.82E−06 | 6.64 | 75.92 | 2.537 | natural C, methanol |
| | THP-1 | 1.03E−04 | 9.48E−05 | =100.0 | −4.341 | synthetic C, DMSO |
| | THP 1 | 4.96E−05 | =3.500 | 67.53 | 14.83 | synthetic C, methanol |
| Colon Cancer | HCT 116 | 5.30E−07 | =3.500 | 43.89 | −1.927 | natural C, methanol |
| | HCT 116 | 2.86E−07 | =3.500 | 63.98 | −1.609 | synthetic C, DMSO |
| | HCT 116 | 5.206E−07 | =3.500 | 63.68 | −2.614 | synthetic C, methanol |
| Ovary Cancer | SW626 | 3.65E−07 | =3.500 | 42.81 | 1.167 | natural C, methanol |
| | SW626 | 9.08E−07 | =3.500 | 43.17 | 5.588 | synthetic C, DMSO |
| | SW626 | 9.921E−07 | =3.500 | 47.2 | 3.62 | synthetic C, methanol |
| Gastric Cancer | NCI-N87 | 2.25E−07 | 2.62 | 41.34 | 11.93 | natural C, methanol |
| | NCI-N87 | >0.0001 | | | | synthetic C, DMSO |
| | NCI-N87 | 3.523E−07 | =3.500 | 23.87 | 6.683 | synthetic C, methanol |
| HUVEC (primary) | HUVEC | 4.83E−05 | 0.45 | =100.0 | −4.548 | natural C, methanol |
| | HUVEC | 1.03E−04 | 0.3523 | =100.0 | −7.188 | synthetic C, DMSO |
| | HUVEC | 4.64E−05 | 0.2985 | =100.0 | −3.312 | synthetic C, methanol |

REFERENCES

Adams, P. D. et al. PHENIX: a comprehensive Python-based system for macromolecular structure solution. *Acta crystallographica. Section D, Biological crystallography* 66, 213-221 (2010).

Altmann K. H. Diversity through semisynthesis: The chemistry and biological activity of semisynthetic epothilone derivatives, *Molecular Diversity* 15:383-399 (2011).

Ammermann J., Schmidt T., Donner J., Reck M., Wagner-Döbler I., Kirschning A., The lactam strategy in question: Synthesis and biological evaluation of "carolactam" *Org. Biomol Chem*, 2017, 15, 8553-8558.

Appling, D. R. Compartmentation of folate-mediated one-carbon metabolism in eukaryotes. *FASEB journal: official publication of the Federation of American Societies for Experimental Biology* 5, 2645-2651 (1991).

Blakley, R. L., Benkovic, S. J. & Whitehead, V. M. *Folates and pterins* (Wiley, N.Y., Chichester, 1984).

Christensen, K. E. & MacKenzie, R. E. in *Folic Acid and Folates*, edited by Gerald Litwack pp. 393-410 Academic Press2008.

Christensen, K. E. & MacKenzie, R. E. Mitochondrial one-carbon metabolism is adapted to the specific needs of yeast, plants and mammals. *BioEssays: news and reviews in molecular, cellular and developmental biology* 28, 595-605 (2006).

Clark, J. E. & Ljungdahl, L. G. Purification and properties of 5,10-methenyltetrahydrofolate cyclohydrolase from *Clostridium formicoaceticum*. *The Journal of biological chemistry* 257, 3833-3836 (1982).

Crowley, P. J., Gutierrez, J. A., Hillman, J. D. & Bleiweis, A. S. Genetic and physiologic analysis of a formyl-tetrahydrofolate synthetase mutant of *Streptococcus mutans*. *J. Bacteriol.* 179, 1563-1572 (1997).

D'Ari, L. & Rabinowitz, J. C. Purification, characterization, cloning, and amino acid sequence of the bifunctional enzyme 5,10-methylenetetrahydrofolate dehydrogenase/5,10-methenyltetrahydrofolate cyclohydrolase from *Escherichia coli*. *The Journal of biological chemistry* 266, 23953-23958 (1991).

Dev, I. K. & Harvey, R. J. A complex of N5,N10-methylenetetrahydrofolate dehydrogenase and N5,N10-methenyltetrahydrofolate cyclohydrolase in *Escherichia coli*. Purification, subunit structure, and allosteric inhibition by N10-formyltetrahydrofolate. *The Journal of biological chemistry* 253, 4245-4253 (1978).

Donner, J. et al. The biofilm inhibitor Carolacton inhibits planktonic growth of virulent pneumococci via a conserved target. *Scientific reports* 6, 29677 (2016).

Ducker, G. S. & Rabinowitz, J. D. One-Carbon Metabolism in Health and Disease. *Cell metabolism* 25, 27-42 (2017).

Eadsforth T C, Cameron S, Hunter W N: The crystal structure of Leishmania major N(5),N(10)-methylenetetrahydrofolate dehydrogenase/cyclohydrolase and assessment of a potential drug target. *Mol Biochem Parasitol* 181: 178-185 (2012c).

Eadsforth, T. C. et al. Assessment of Pseudomonas aeruginosa N5,N10-methylenetetrahydrofolate dehydrogenase-cyclohydrolase as a potential antibacterial drug target. *PloS one* 7, e35973 (2012a).

Eadsforth, T. C. et al. Characterization of 2,4-Diamino-6-oxo-1,6-dihydropyrimidin-5-yl Ureido Based Inhibitors of Trypanosoma brucei FoID and Testing for Antiparasitic Activity. *Journal of medicinal chemistry* 58, 7938-7948 (2015).

Eadsforth, T. C., Maluf, F. V. & Hunter, W. N. Acinetobacter baumannii FoID ligand complexes—potent inhibitors of folate metabolism and a re-evaluation of the structure of LY374571. *The FEBS journal* 279, 4350-4360 (2012b).

Eberhardt, A., Wu, L.J., Errington, J., Vollmer, W. & Veening, J.-W. Cellular localization of choline-utilization proteins in *Streptococcus pneumoniae* using novel fluorescent reporter systems. *Molecular microbiology* 74, 395-408 (2009).

Emsley, P., Lohkamp, B., Scott, W. G. & Cowtan, K. Features and development of Coot. *Acta crystallographica. Section D, Biological crystallography* 66, 486-501 (2010).

Green, J. M. & Matthews, R. G. Folate Biosynthesis, Reduction, and Polyglutamylation and the Interconversion of Folate Derivatives. *EcoSal Plus* 2 (2007).

Gustafsson, R. et al. Crystal Structure of the Emerging Cancer Target MTHFD2 in Complex with a Substrate-Based Inhibitor. *Cancer research* 77, 937-948 (2017).

Jain M., Nilsson R, Sharma S, Madhusudhan N, Kitami T, Souza A L, Kafri R, Kirschner M W, Clish C B, Mootha V K, Metabolite profiling identifies a key role for glycine in rapid cancer cell proliferation. *Science* 336 (6084): 1040-4 (2012).

Jansen, R. et al. Carolacton—A Macrolide Ketocarbonic Acid that Reduces Biofilm Formation by the Caries- ad Endocarditis-Associated Bacterium Streptococcus mutans. *Eur. J. Org. Chem.* 2010, 1284-1289 (2010).

Kabsch, W. XDS. *Acta crystallographica. Section D, Biological crystallography* 66, 125-132 (2010).

Kunze, B. et al. Damage of *Streptococcus mutans* biofilms by carolacton, a secondary metabolite from the myxobacterium Sorangium cellulosum. *BMC microbiology* 10, 199 (2010).

Laskowski, R. A. & Swindells, M. B. LigPlot+: multiple ligand-protein interaction diagrams for drug discovery. *Journal of chemical information and modeling* 51, 2778-2786 (2011).

Lau, P. C., Sung, C. K., Lee, J. H., Morrison, D. A. & Cvitkovitch, D. G. PCR ligation mutagenesis in transformable streptococci. Application and efficiency. *Journal of Microbiological Methods* 49, 193-205 (2002).

Liu, H. & Naismith, J. H. A simple and efficient expression and purification system using two newly constructed vectors. *Protein expression and purification* 63, 102-111 (2009).

Maden B E, Tetrahydrofolate and tetrahydromethanopterin compared. Functionally distinct carriers in C1 metabolism. *Biochem. J.* 350, 609-629 (2000).

Marcrina, F. L. et al. Novel shuttle plasmid vehicles for *Escherichia-Streptococcus* transgeneric cloning. *Gene* 25, 145-150 (1983).

McCoy, A. J. et al. Phaser crystallographic software. *Journal of applied crystallography* 40, 658-674 (2007).

McDonald, A. C. et al. A phase I and pharmacokinetic study of LY231514, the multitargeted antifolate. *Clinical cancer research: an official journal of the American Association for Cancer Research* 4, 605-610 (1998).

Mejia N R, MacKenzie R E, NAD-dependent methylenetetrahydrofolate dehydrogenase is expressed by immortal cells. *The Journal of biological chemistry* 260, 14616-14620 (1985).

Mosman T. Rapid colorimetric assay for cellular growth and survival: application to proliferation and cytotoxic assays. *J Immunol Methods* 65, 55-63 (1983).

Murta S M, Vickers T J, Scott D A, Beverley S M: Methylene tetrahydrofolate dehydrogenase/cyclohydrolase and the synthesis of 10-CHO-THF are essential in Leishmania major. *Mol Microbiol* 71: 1386-1401 (2009).

Nilsson, R. et al. Metabolic enzyme expression highlights a key role for MTHFD2 and the mitochondrial folate pathway in cancer. *Nature communications* 5, 3128 (2014).

Rajagopalan, P. T. R. et al. Interaction of dihydrofolate reductase with methotrexate: ensemble and single-molecule kinetics. *Proceedings of the National Academy of Sciences of the United States of America* 99, 13481-13486 (2002).

Reck, M. et al. The biofilm inhibitor carolacton disturbs membrane integrity and cell division of *Streptococcus mutans* through the serine/threonine protein kinase PknB. *Journal of bacteriology* 193, 5692-5706 (2011).

Sah, S. & Varshney, U. Impact of Mutating the Key Residues of a Bifunctional 5,10-Methylenetetrahydrofolate Dehydrogenase-Cyclohydrolase from *Escherichia coli* on Its Activities. *Biochemistry* 54, 3504-3513 (2015a).

Sah, S., Aluri, S., Rex, K. & Varshney, U. One-carbon metabolic pathway rewiring in *Escherichia coli* reveals an evolutionary advantage of 10-formyltetrahydrofolate synthetase (Fhs) in survival under hypoxia. *Journal of bacteriology* 197, 717-726 (2015b).

Schmidt, A. et al. Structures of Three Inhibitor Complexes Provide Insight into the Reaction Mechanism of the Human Methylenetetrahydrofolate Dehydrogenase/Cyclohydrolase. *Biochemistry* 39, 6325-6335 (2000).

Schmidt, T. and A. Kirschning. Total synthesis of carolacton, a highly potent biofilm inhibitor. *Angew. Chem.* 124:1087-1091; *Angew. Chem. Int. Ed. Engl.* 51, 1063-1066 (2012).

Stumpp N. Premnath P., Schmidt T., Ammerman J., Dräger G., Reck M., Jansen R., Stiesch M., Wagner-Döbler I.

Kirschning A., Synthesis of new carolacton derivatives and their activity against biofilms of oral bacteria, Org Biomol Chem 13, 5765 (2015).

Shih, C. et al. LY231514, a pyrrolo2,3-dpyrimidine-based antifolate that inhibits multiple folate-requiring enzymes. *Cancer research* 57, 1116-1123 (1997).

Skubak, P., Murshudov, G. N. & Pannu, N. S. Direct incorporation of experimental phase information in model refinement. *Acta crystallographica. Section D, Biological crystallography* 60, 2196-2201 (2004).

Stuart K, Brun R, Croft S, Fairlamb A, Gurtler RE, McKerrow J et al.: Kinetoplastids: related protozoan pathogens, different diseases. J Clin Invest 2008, 118: 1301-1310.

Sudhakar, P. et al. Construction and verification of the transcriptional regulatory response network of *Streptococcus mutans* upon treatment with the biofilm inhibitor carolacton. *BMC genomics* 15, 362 (2014).

Tedeschi, P. M., Vazquez, A., Kerrigan, J. E. & Bertino, J. R. Mitochondrial Methylenetetrahydrofolate Dehydrogenase (MTHFD2) Overexpression Is Associated with Tumor Cell Proliferation and Is a Novel Target for Drug Development. *Molecular cancer research: MCR* 13, 1361-1366 (2015).

Tonkinson, J. L. et al. The antiproliferative and cell cycle effects of 5,6,7, 8-tetrahydro-N5,N10-carbonylfolic acid, an inhibitor of methylenetetrahydrofolate dehydrogenase, are potentiated by hypoxanthine. *The Journal of pharmacology and experimental therapeutics* 287, 315-321 (1998).

Winter, G. xia2. An expert system for macromolecular crystallography data reduction. *J Appl Crystallogr* 43, 186-190 (2010).

Wohlfarth, G., Geerligs, G. & Diekert, G. Purification and characterization of NADP(+)-dependent 5,10-methylenetetrahydrofolate dehydrogenase from Peptostreptococcus productus marburg. *J. Bacteriol.* 173, 1414-1419 (1991).

Zongru G., The modification of natural products for medical use. *Acta Pharmaceutica Sinica B* 7:119-136 (2017).

What is claimed is:

1. A method for the treatment of a disease associated with activity of a 5,10-methylenyltetrahydrofolate cyclohydrolase/5,10-methylene tetrahydrofolate dehydrogenase enzyme in pathological eukaryotic cells, selected from the group consisting of a liver neoplasm, a malignant lymphoma, a leukemia, a colon cancer, an ovary cancer, a gastric cancer or a parasitic disease,
   comprising administering to a subject a compound according to Formula I

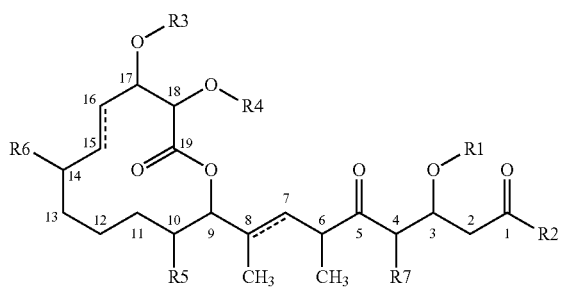

Formula I wherein
each of R1, R3 and R4 are independently selected from H, a C1-C12 alkyl or a C7-C12 linear, branched or cyclic, saturated, unsaturated or aromatic hydrocarbon radical;
R2 is selected from H, a C1-C12 alkyl group, or a C7-C12 linear, branched or cyclic, saturated, unsaturated or aromatic hydrocarbon radical, or OR8, wherein R8 is selected from H, a C1-C12 alkyl group, or a C7-C12 linear, branched or cyclic, saturated, unsaturated or aromatic hydrocarbon radical; and
each of R5, R6 and R7 are independently selected from H or a C1-C12 alkyl groups.

2. The method for according to claim 1, wherein the compound according to Formula I is such that the bond connecting C-15 and C-16 is hydrogenated to a single bond and C-15 and C-16 are saturated with hydrogen atoms and/or wherein the bond connecting C-7 and C-8 is hydrogenated to a single bond and C-7 and C-8 are saturated with hydrogen atoms.

3. The method for according to claim 1, wherein the compound according to Formula I is such that the bonds connecting C-15 and C-16 and C-7 and C-8 are double bonds, according to Formula II

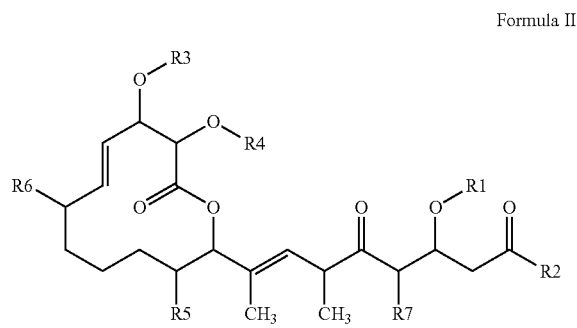

Formula II wherein R1-R7 are as for Formula I in claim 1.

4. The method according to claim 1, wherein the compound is according to Formula III

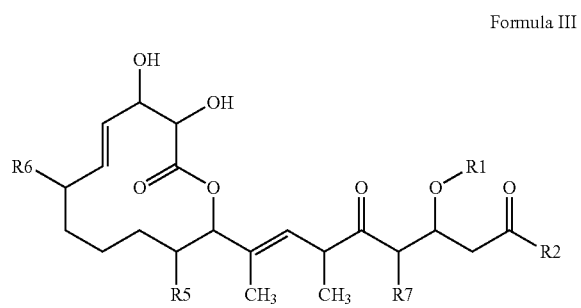

Formula III wherein
R1 is selected from H. a C1-C12 alkyl group, or a C7-C12 linear, branched or cyclic, saturated, unsaturated or aromatic hydrocarbon radical;
R2 is selected from H, a C1-C12 alkyl group, or a C7-C12 linear, branched or cyclic, saturated, unsaturated or aromatic hydrocarbon radical, or OR8, wherein R8 is selected from H, a C1-C12 alkyl group, or a C7-C12 linear, branched or cyclic, saturated, unsaturated or aromatic hydrocarbon radical; and
each of R5, R6 and R7 are independently selected from H or a C1-C12 alkyl group.

5. The method according to claim 1, wherein the compound is according to Formula IV Formula IV

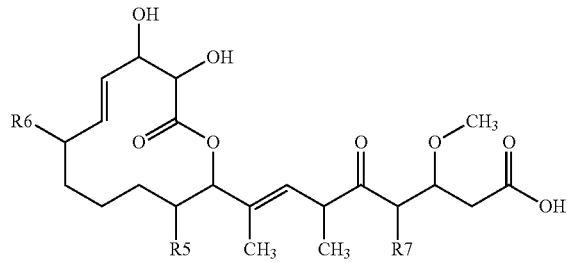

wherein
each of R5, R6 and R7 are independently selected from H or a C1-C12 alkyl group.

6. The method according to claim 1, according to Formula V (Carolacton)

Formula V

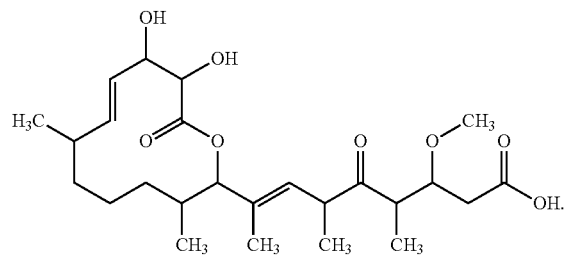

7. The method according to claim 1, wherein the compound is according to Formulae VI, VII, VIII, IX, X or XI Formula VI

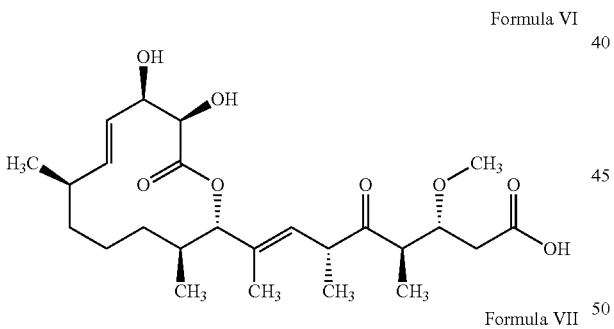

Formula VII

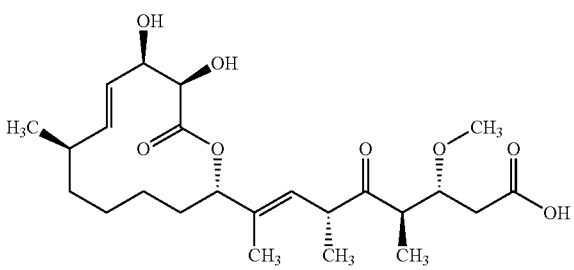

Formula VIII

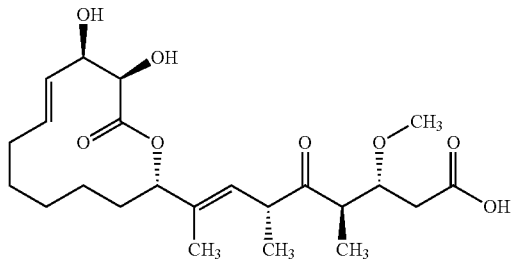

Formula IX

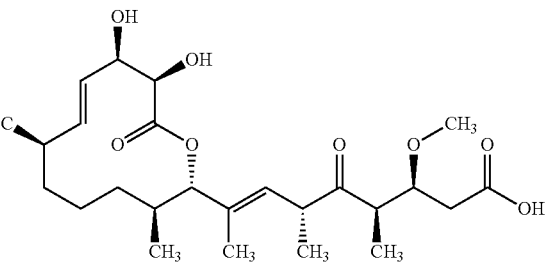

Formula X

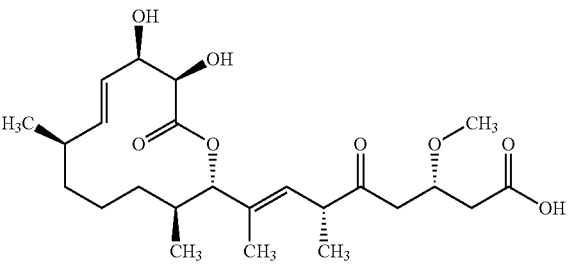

Formula XI

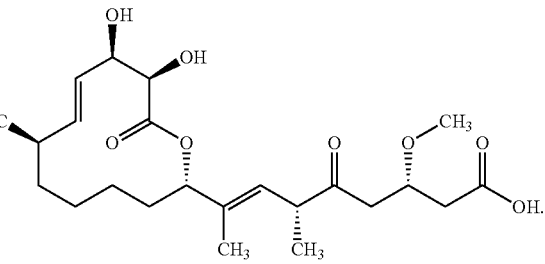

8. The method according to claim 1, wherein a pharmaceutical composition comprises one or more compounds according to claim 1 and a pharmaceutically acceptable carrier is administered to a subject.

9. The method according to claim 1, wherein the parasitic disease is selected from the group consisting of sleeping sickness, Leishmaniasis and Chagas disease.

* * * * *